US011026384B2

(12) United States Patent
Li et al.

(10) Patent No.: US 11,026,384 B2
(45) Date of Patent: Jun. 8, 2021

(54) BARLEY AND USES THEREOF

(71) Applicants: Zhongyi Li, Kaleen (AU); Matthew Kennedy Morell, Manila (PH)

(72) Inventors: Zhongyi Li, Kaleen (AU); Matthew Kennedy Morell, Manila (PH)

(73) Assignee: The Healthy Grain Pty Limited, Campbell (AU)

( * ) Notice: Subject to any disclaimer, the term of this patent is extended or adjusted under 35 U.S.C. 154(b) by 0 days.

(21) Appl. No.: 16/217,729

(22) Filed: Dec. 12, 2018

(65) Prior Publication Data
US 2019/0150385 A1  May 23, 2019

Related U.S. Application Data

(62) Division of application No. 13/387,973, filed as application No. PCT/AU2010/000968 on Jul. 30, 2010, now Pat. No. 10,154,632.

(51) Int. Cl.
| | |
|---|---|
| *A61K 31/718* | (2006.01) |
| *A01H 5/10* | (2018.01) |
| *C12N 15/82* | (2006.01) |
| *C12Q 1/25* | (2006.01) |

(52) U.S. Cl.
CPC ............ *A01H 5/10* (2013.01); *C12N 15/8245* (2013.01); *C12Q 1/25* (2013.01)

(58) Field of Classification Search
None
See application file for complete search history.

(56) References Cited

U.S. PATENT DOCUMENTS

| | | | |
|---|---|---|---|
| 3,690,896 A | 9/1972 | Maxwell et al. | |
| 4,770,710 A | 9/1988 | Friedman et al. | |
| 5,051,271 A | 9/1991 | Iyengar et al. | |
| 5,792,920 A | 8/1998 | Bridges et al. | |
| 6,013,861 A | 1/2000 | Bird et al. | |
| 6,083,547 A | 7/2000 | Katta et al. | |
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,730,825 B1 | 5/2004 | Goldsbrough et al. | |
| 6,734,339 B2 | 5/2004 | Block et al. | |
| 6,897,354 B1 | 5/2005 | Yamamori et al. | |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,521,593 B2* | 4/2009 | Regina .................... | C08B 30/00 435/320.1 |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,790,955 B2 | 9/2010 | Li et al. | |
| 7,812,221 B2 | 10/2010 | Regina et al. | |
| 7,888,499 B2* | 2/2011 | Morell .................... | A01H 5/00 536/102 |
| 7,919,132 B2 | 4/2011 | Regina et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 8,501,262 B2 | 8/2013 | Bird et al. | |
| 2003/0035857 A1 | 2/2003 | Sroka et al. | |
| 2004/0060083 A1 | 3/2004 | Regina et al. | |
| 2004/0204579 A1 | 10/2004 | Block et al. | |
| 2005/0164178 A1 | 7/2005 | Morell et al. | |
| 2006/0010517 A1 | 1/2006 | Li et al. | |
| 2007/0300319 A1 | 12/2007 | Li et al. | |
| 2011/0010807 A1 | 1/2011 | Morell et al. | |
| 2011/0045127 A1 | 2/2011 | Ral et al. | |
| 2011/0059225 A1 | 3/2011 | Li et al. | |
| 2011/0212916 A1 | 9/2011 | Bird et al. | |

(Continued)

FOREIGN PATENT DOCUMENTS

| | | |
|---|---|---|
| GB | 2 360 521 | 9/2001 |
| WO | WO 1997/22703 | 6/1997 |

(Continued)

OTHER PUBLICATIONS

Sestilli et al, 2010, BMC Plant Biology, 10:1-12.*
Bird et al, 2008, British Journal of Nutrition, 99:1032-1040.*
Topping et al, 2003, Starch, 55:539-545.*
Banks et al, 1971, Starch, 23:118-124.*
Keogh et al, 2007, European Journal of Clinical Nutrition, 61:597-604.*
U.S. Appl. No. 13/462,629, filed May 2, 2012, Li et al.
U.S. Appl. No. 13/466,772, filed May 8, 2012, Morell et al.
International Preliminary Report on Patentability, dated Jan. 31, 2012 in connection with PCT International Application No. AU2010/000968, of which the subject application is a national stage entry.
International Search Report, dated Sep. 15, 2010 in connection with PCT International Application No. AU2010/000968, of which the subject application is a national stage entry.

(Continued)

*Primary Examiner* — Jason Deveau Rosen
(74) *Attorney, Agent, or Firm* — John P. White

(57) ABSTRACT

The invention provides barley grain comprising a reduced level or activity of starch synthase IIa protein and a starch content of at least 41% (w/w) and methods of producing, identifying and using same. The grain may comprise an amylase content of at least 50%, a β-glucan content of 5-9% (w/w) or greater than 9% (w/w), and/or a fructan content of 3-11% (w/w). The fructan may comprise a degree of polymerization from about 3 to about 12. For example, the plant and grain comprises a sex6-292 allele and/or an amo1 mutation. A food or beverage product, and methods of producing a food or beverage product, comprising obtaining or producing the subject grain and processing the grain to produce the product. Also contemplated are methods of improving one or more indicators of health in a mammal comprising administering a composition comprising the subject barley grain or a product comprising same.

15 Claims, 2 Drawing Sheets
Specification includes a Sequence Listing.

(56) References Cited

U.S. PATENT DOCUMENTS

| | | |
|---|---|---|
| 2011/0281818 A1 | 11/2011 | Jenkins et al. |
| 2012/0074247 A1 | 3/2012 | Regina et al. |
| 2012/0114770 A1 | 5/2012 | Regina et al. |
| 2013/0115362 A1 | 5/2013 | Regina et al. |
| 2014/0044826 A1 | 2/2014 | Regina et al. |

FOREIGN PATENT DOCUMENTS

| | | |
|---|---|---|
| WO | WO 1999/014314 | 3/1999 |
| WO | WO 1999/066050 | 12/1999 |
| WO | WO 2000/015810 | 3/2000 |
| WO | WO 2000/66745 | 9/2000 |
| WO | WO 2001/32886 | 5/2001 |
| WO | WO 2002/037955 | 5/2002 |
| WO | WO 2002/101059 | 12/2002 |
| WO | WO 2003/023024 | 3/2003 |
| WO | WO 2003/094600 | 11/2003 |
| WO | WO 2005/001098 | 1/2005 |
| WO | WO 2005/040381 | 6/2005 |
| WO | WO 2006/069422 | 7/2006 |
| WO | WO 2010/006373 | 1/2010 |
| WO | WO 2011/011833 | 2/2011 |
| WO | WO 2012/058730 | 5/2012 |
| WO | WO 2012/103594 | 8/2012 |

OTHER PUBLICATIONS

Clarke et al., "Gene expression in a starch synthase IIa mutant of barley: changes in the level of gene transcription and grain composition." Functional Integrated Genomics (2008) 8:211-221 (Only the Abstract provided).
Morell et al., "Barley sex6 Mutants Lack Starch Synthase IIa Activity and Contain a Starch with Novel Properties," The Plant Journal (2003) 34:173-185.
File History of U.S. Pat. No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).
File History of U.S. Pat. No. 7,700,139, Bird et al., issued Apr. 20, 2010 (U.S. Appl. No. 11/324,063, filed Dec. 30, 2005).
File History of U.S. Patent Application Publication No. 2006-0286186, Bird et al., published Dec. 21, 2006 (U.S. Appl. No. 11/417,330, filed May 2, 2006).
File History of U.S. Patent Application Publication No. US 2011-0212916, Bird et al., published Sep. 1, 2011 (U.S. Appl. No. 12/799,013, filed Apr. 16, 2010).
File History of U.S. Pat. No. 7,790,955, Li et al., issued Sep. 7, 2010 (U.S. Appl. No. 10/577,564, filed Apr. 27, 2006).
File History of U.S. Patent Application Publication No. 2011-0059225, Li et al., published Mar. 10, 2011 (U.S. Appl. No. 12/806,167, filed Aug. 6, 2010).
File History of U.S. Pat. No. 7,888,499, Morell et al., issued Feb. 15, 2011 (U.S. Appl. No. 10/416,439, filed Dec. 5, 3003).
File History of U.S. Pat. No. 7,001,771, Morell et al., issued Feb. 21, 2006 (U.S. Appl. No. 10/018,418, filed May 9, 2002).
File History of U.S. Pat. No. 7,700,826, Morell et al., issued Apr. 20, 2010 (U.S. Appl. No. 11/231,599, filed Sep. 21, 2005).
File History of U.S. Pat. No. 7,521,593, Regina et al., issued Apr. 21, 2009 (U.S. Appl. No. 10/434,893, filed May 9, 2003).
File History of U.S. Pat. No. 7,919,132, Regina et al., issued Apr. 5, 2011 (U.S. Appl. No. 12/384,823, filed Apr. 9, 2009).
File History of U.S. Pat. No. 7,667,114, Morell et al., issued Feb. 23, 2010 (U.S. Appl. No. 10/204,347, filed Feb. 20, 2002).
File History of U.S. Patent Application Publication No. 2011-0010807, Morell et al., published Jan. 13, 2011 (U.S. Appl. No. 12/707,437, filed Feb. 17, 2010).
File History of U.S. Patent Application Publication No. 2010-0330253, Morell et al., published Dec. 20, 2010 (U.S. Appl. No. 12/800,143, filed May 10, 2010).
File History of U.S. Patent Application Publication No. 2012-0074247, Regina et al., published Mar. 29, 2012 (U.S. Appl. No. 13/243,220).
Abel et al., GenBank Accession #Y10416 (Jan. 1997) S. Tuberosum mRNA for Soluble Starch Synthase.
Abel, G.J.W. et al., "Cloning and functional analysis of a cDNA encoding a novel 139 kDa Starch Synthase from Potato (*Solanum tuberosum* L.)," Plant J. 10(6): 981-991 (1996).
Ainsworth, C. et al., "Expression, organization and structure of the genes encoding the waxy protein (granule-bound starch synthase) in wheat," Plant Mol. Biol. 22:67-82 (1993).
Baba, T. et al., "Identification, cDNA cloning and gene expression of soluble starch synthase in rice (*Oryza stativa* L.) Immature Seeds," Plant Physiol. 103:565-573 (1993).
Batey and Curtin, "Measurement of Amylose/Amylopectin Ratio by High-Performance Liquid Chromatography," Starch 48: 338-344 (1996).
Bhullar et al., GenBank Accession #CAB40374 (Apr. 1999) Starch synthase isoform SS III [Vigna unguiculata].
Blauth et al., "Identification of Mutator Insertional Mutants of Starch-Branching Enzyme 2a in Corn," Plant Physiology 125:1396-1405 (2001).
Block et al., GenBank Accession #U48227 (Jun. 1996) Triticum aestivum soluble starch synthase mRNA, partial cds.
Boyer and Preiss, "Evidence for Independent Genetic Control of the Multiple Forms of Maize Endosperm Branching Enzymes and Starch Synthases," Plant Physiology 67: 1141-1145 (1981).
Buleon et al., "Starch Granules: Structure and Biosynthesis," International Journal of Biological Macromolecules 23: 85-112 (1998).
Calvert et al., High Amylose Glacier Barley in Swine Diets. Nutritional Reports International, 1981, 23:29-36.
Craig et al., "Mutations in the Gene Encoding Starch Synthase II Profoundly Alter Amylopectin Structure in Pea Embryos," The Plant Cell 10:413-426 (1998).
Denyer, K. et al., "Identification of Multiple Isoforms of Soluble and Granule Bound Starch Synthase in Developing Wheat Endosperm," Planta 196: 256-265 (1995).
D'Hulst et al, GenBank Accession #AAC17969 (Nov. 2001) Granule-bound starch synthase I precursor [Chlamydomonas reinhardtii].
Dry, I. et al., "Characterization of cDNAs encoding two isoforms of granule-bound synthase which show differential expression in developing storage organs of pea and potato," Plant J. 2 (2) : 193-202 (1992).
Edwards et al., "Biochemical and Molecular Characterization of a Novel Starch Synthase from Potato Tubers," Plant J. 8 (2) : 283-294 (1995).
Flipse et al., "Introduction of Sense and Antisense cDNA for Branching Enzyme in the Amylose-Free Potato Mutant Leads to Physico-Chemical Changes in the Starch," Plant a 198: 340-347 (1996).
Fujita et al., "Grain and Starch Characteristics of the Double Recessive Lines for Amylose-free and High Amylose Gene in Barley," Breeding Science 49: 217-219 (1999).
Fujita et al., "Antisense Inhibition of Isoamylase Alters the Structure of Amylopectin and the Physiochemical Properties of Starch in Rice Endosperm," Plant Cell Physiol. 44(6):607-618 (2003).
Gao and Chibbar, "Isolation, Characterization, and Expression Analysis of Starch Synthase IIa cDNA from wheat (*Triticum aestivum* L. )," Genome 43:768-775 (2000).
Gao et al., GenBank Accession #AAC14014 (Apr. 1998) Starch synthase DULL 1 [*Zea mays*].
Gao et al., GenBank Accession #AAC14015 (Apr. 1998) Starch synthase DULL 1 [*Zea mays*].
Gao et al., "Characterization of dull I, a Maize Gene Coding for a Novel Starch Synthase," Plant Cell 10:399-412 (1998).
Gao et al., "Triticum aestivum mRNA for Starch Synthase IIa-2 (wSs2a-2)." EMBL Abstract Accession No. AJ269503, Jul. 6, 2000.
Gao et al., GenBank Accession #AJ26502 (Apr. 2002) Triticum aestivum mRNA for starch synthase Iia-1 (wSs2a-1 gene).
Gao et al., GenBank Accession #CAB86618 (Apr. 2002) Starch synthase Iia-1 [Triticum aestivum].
Gillespie, K. "Type 1 diabetes: pathogenesis and prevention," CMAJ, 2006, vol. 175, pp. 165-170.

(56) References Cited

OTHER PUBLICATIONS

Goering and DeHass, "A Comparison of the Properties of Large- and Small-Granule Starch Isolated from Several Isogenic Lines of Barley," Cereal Chemistry 51:573-578 (1974).
Harn et al., "Isolation and Characterization of the zSSIIA and zSSIIb Starch Synthase cDNA Clones from Maize Endosperm," Plant Mol. Biol. 37:639-649 (1998).
Holmes et al., Henderson's Dictionary of Biological Terms, 9th Ed., Van Nostrand Reinhold Co., New York, 1979, p. 218.
Jansson et al., "Cloning, Characterization and Modification of Genes Encoding Starch Branching Enzymers in Barley." Starch: Structure and Functionality. Royal Society of Chemistry, London, pp. 196-203 (1997).
Klosgen, et al., "Molecular Analysis of the Waxy Locus of Zea mays," Mol. Gen. Genet. 203: 237-244 (1986).
Knight, et al., "Molecular Cloning of Starch Synthase I from Maize (w64) Endosperm and Expression in Escherichia coli," Plant J. 14 (5) : 613-622 (1998).
Kull et al., "Genetic Engineering of Potato Starch Composition: Inhibition of Amylose Biosynthesis in Tubers from Transgenic Potato Lines by the Expression of Antisense Sequences of the Gene for Granule-bound Starch Synthase," J. Genet. Breed. 49: 69-76 (1995).
Li et al., "Cloning and Characterization of a Gene Encoding Wheat Starch Synthase I," Theor. AEEI. Genet. 98: 1208-1216 (1999).
Li et al., "The Localization and Expression of the Class II Starch Synthases of Wheat.". Plant Physiology 120:1147-1155 (1999).
Li et al., "Triticum aestivum Starch Synthase IIA mRNA, Complete cds," EMBL Abstract Accession No. AF155217, Sep. 7, 1999.
Liu et al., "Stable Inheritance of the Antisense Waxy Gene in Transgenic Rice with Reduced Amylose Level and Improved Quality," Transgenic Research, 12:71-82, (2003).
Mazzolini et al., "Assaying synthetic ribozymes in plants: high-level expression of a functional hammerhead structure fails to inhibit target gene activity in transiently transformed protoplasts," Plant Mol. Biol. 20: 715-731 (1992).
Miao, Hongmei et al., (2004) "Evaluation and Caracterization of an Endosperm-Specific sbella Promoter in Wheat II Chinese Science Bulletin," vol. 49, No. 6, pp. 579-585.
Mizuno et al., "Alteration of the Structural Properties of Starch Components by the Lack of an Isoform of Starch Branching Enzyme in Rice Seeds," J. Biol. Chern. 268 (25): 19084-19091 (1993).
Morell et al., "The Biochemistry and Molecular Biology of Starch Synthesis in Cereals," Aust. J. Plant. Physiol. 22: 647-660 (1995).
Myers et al., "Recent Progress toward Understanding Biosynthesis of the Amylopection Crystal," Plant Physiology 122: 989-997 (2000).
Nakamura Y., "Towards a Better Understanding of the Metabolic System for Amylopectin Biosynthesis in Plants: Rice Endosperm as s Model Tissue." Plant Cell Physiology 43 (7): 718-725 (2002).
Nishi et al., "Biochemical and Genetic Analysis of the Effects of Amylose-Extender Mutation in Rice Endosperm." Plant Physiology 127:459-472 (2001).
Okagaki R. J., "Nucleotide Sequence of a Long cDNA from the Rice Waxy Gene," Plant Molecular Biology 19: 513-516' (1992).
Puchta, "Gene Replacement by Homologous Recombination in Plants," Plant Mol. Biol. 48: 173-182 (2002).
Rahman et al., GenBank Accession #AF076680 (May 1999) Aegilops tauschii starch branching enzyme-I (SBE-1) gene, complete cds.
Rahman, S. et al., (1995) "The Major Proteins of Wheat Endosperm Starch Granules," Aust. J. Plant Physiol. 22:793-803.
Rahman, S. et al., (1997) A Complex Arrangement of Genes at a Starch Branching Enzyme I Locus in the D-genome Donor of wheat,: Genome 40: 465-474.
Rahman, S. et al., (1999) "Characterisation of a Gene Encoding Wheat Endosperm Starch Branching Enzyme-I," Theor. Appl. Genet. 98: 156-163.
Rahman, S. et al., (2001) "Comparison of Starch-Branching Enzyme Genes Reveals Evolutionary Relationships Among Isoforms." Characterization of a Gene for StarchBranching Enzyme IIa from the Wheat D Genome Donor Aegilops tauschii II Plant Physiology, vol. 125, pp. 1314-1324.
Regina A., (2006) "High-amylose wheat generated by RNA interference improves indices of large-bowel health in rats," PNAS, vol. 103, pp. 3546-3551.
Safford, et. al., "Consequences of Antisense RNA Inhibition of Starch Branching Enzyme Activity on Properties of Potato Starch," Carbohydrate Polymers 35: 155-168 (1998).
Sathish et al. "Cloning and Anti-Sense RNA Constructs of a Startch Branching Enzyme Gene From Barley Endosperm," Photosynthesis: from Light to Biosphere vol. V. P. Mathis (ed.) pp. 313-316 (1995).
Schondelmaier et al., "Genetical Studies in the Mode of Inheritance and Localization of the amol (High Amylose) Gene in Barley," Plant Breeding 109: 274-280 (1992).
Schulman et al., Structural analysis of starch from normal and shx (shrunken endosperm) barley (Hordeum vulgare L.). Carbohydrate Research, 1995, 275:361-369.
Schulman and Kammiovirta, Purification of Barley Starch by Protein Extraction. Starch, 1991, 43(10):387-389.
Schwall, et al., "Production of Very-High-Amylose Potato Starch by Inhibition of SBE A and B," Nature Biotechnology 18: 551-554 (2000).
Shannon and Garwood, "In Starch: Chemistry and Technology," Whistler et al., eds, Academic Press, Orlando, FL, 25-86 (1984).
Sidebottom, et al., "Characterization of the Difference of Starch Branching Enzyme Activities in Normal and Low-Amylopectin Maize during Kernel Development," Journal of Cereal Science 27: 279-287.
Slade et al., "Development of High Amylose Wheat Through Tilling," BMC Plant Biology, 12:69-100, 2012.
Sun et al., "Identification of Four Starch-Branching Enzymes in Barley Endosperm: Partial Purification of forms I, IIa and IIb," New Phytol. 137:215-222 (1997).
Sun et al., "The Two Genes Encoding Starch-Branching Enzymes IIa and IIb Are Differentially Expressed in Barley," Plant Physiology 118:37-49 (1998).
Sundberg et al., "Glycaemic Responses and Hyopcholesterolaemic Effects of High-Amylose Barley Diets on Broiler Chicks," J. Sci. Food Agric. 76:457-463 (1998).
Takaoka, M. et al., "Structural characterization of high molecular weight starch granule-bound proteins in wheat (Triticum aestivum L.)," J. Agric. Food Chem. 45: 2929-2934 (1997).
Terada at al., "Efficient Gene Targeting by Homologous Recombination in Rice," Nature Biotech. 20: 1030-1034 (1997).
Tester, R.F. "The effects of ambient temperature during the Grain-filling period on the composition and properties of starch and four barley genotypes." (1991) Journal of Cereal Science 13:113-127.
Tester, T.F. "Influence of growth conditions on barley starch properties." (1997) Biological Macromolecules 21:37-45.
Tetlow et al. (2004) "Recent developments in understanding the regulation of starch metabolism in higher plants." Journal of Experimental Botany 55(406):2131-2145.
Thomas, et al., "Size Constraints for Targeting Post-Transcriptional Gene Silencing and for RNA-directed Methylation in Nicotiana benthamiana Using a Potato Virus X Vector," Plant J. 25 : 417-425 (2001).
USDA, ARS, National Genetic Resources Program. Germplasm Resources Information Network (GRIN) [Online Database] National Germplasm Resources Laboratory, Beltsville, Maryland (http://www.ars-grin.gov/npgs/), GRIN System [Accession No. GSHO 2476, Jun. 23, 1997).
Van der Leij et al., "Sequence of the Structural Gene for Granule-Bound Starch Synthase of Potato (Solanum tuberosum L.) and Evidence for a Single Point Deletion in the amf allele," Mol. Gen. Genet. 228: 240-248 (1991).
Vrihten and Nakamura, "Wheat Granule-Bound Starch Synthase I and II Are Encoded by Separate Genes That Are Expressed in Different Tissues," Plant Physiology 122:255-263 (2000).
Walker and Meritt, "Genetic Control of Abnormal Starch Granules and High Amylose Content in a Mutant of Glacier Barley," Nature 221:482-484 (1969).

(56) References Cited

OTHER PUBLICATIONS

Walter et al., GenBank Accession #AAB17085 (Oct. 1996) Starch Synthase.
Walter et al., GenBank Accession #U66377 (Oct. 1996) Triticum aestivum soluble starch synthase mRNA; partial cds.
Wasserman et al. (2004) "Microstructure, Thermal properties and susceptibility of the high amylose wheat starch to enzymatic hydrolysis: A new material for resistant starch (SRIII) production," Polish Journal of Food and Nutrition Sciences vol. 13-54, No. 2, pp. 151-156.
Wei et al. "C-Type Starch from High-Amylose Rice Resistant Starch Granules Modified by Antisense RNA Inhibition of Starch Branching Enzyme," Journal of Agricultural and Food Chemistry, 58: 7383-7388, 2010.
Yamamori and Endo, "Variation of Starch Granule Proteins and Chromosome Mapping of Their Coding Genes in Common Wheat," Theor. Appl. Genet. 93: 275-181 (1996).
Yamamori et al., "Genetic Elimination of a Starch Granule Protein, SGP-1, of Wheat Generates an Altered Starch with Apparent High Amylose," TAG Theoretical and Applied Genetics 101: 21-29 (2000).
Yamamori, "Selection of a Wheat Lacking a Putative Enzyme for Starch Synthesis, SGP-1," Proc. 9th In Wheat Gen. Symp. 4:300-302 (1998).
Yoshimoto et al., Molecular Structure and Some Physiochemical Properties of High-Amylose Barley Starches. Cereal Chem, 2000, 77(3):279-285.
Zobel et al., Starch Gelatinization: An X-ray Diffraction Study. Cereal Chem, 1988, 65(6):443-446.
Zobel, B.F., Starch Crystal Transformations and Their Industrial Importance. Starch, 1988, 40(1): 1-7.
Zwar and Chandler, α-Amylose production and leave protein synthesis in a gibberellin-responsive dwarf mutant of 'Himalaya' barley (*Hordeum vulgare* L.). Planta, 1995, 197:39-48.
Andersson et al. (1999) Chemical Composition and Microstructure of Two Naked Waxy Barleys. Journal of Cereal Science, 30, 183-191.
Ball and Morell (2003) From Bacterial Glycogen to Starch: Understanding the Biogenesis of the Plant Starch Granule. Annu. Rev. Plant Biol. 54:207-33.
Ball et al. (1996) From Glycogen to Amylopectin: A Model for the Biogenesis of the Plant Starch Granule. Cell, vol. 86, 349-352.
Bird et al. (2004) A Novel Barley Cultivar (Himalaya 292) with a Specific Gene Mutation in Starch Synthase IIa Raises Large Bowel Starch and Short-Chain Fatty Acids in Rats. The Journal of Nutrition. 134:831-835.
Bird et al. (2004) A novel high-amylose barley cultivar (*Hordeum vulgare* var. Himalaya 292) lowers plasma cholesterol and alters indices of large-bowel fermentation in pigs. British Journal of Nutrition, 92, 607-615.
Boyer and Preiss (1978) Multiple Forms of (1 → 4)-α-D-Glucan, (1 → 4)-α-D-glucan-6-Glycosyl Transferase From Developing *Zea mays* L. Kernels. Carbohydrate Research, 61:321-334.
Cao et al. (1999) Identification of the Soluble Starch Synthase Activities of Maize Endosperm. Plant Physiology, vol. 120, pp. 205-215.
Cao et al. (2000) Purification and Characterization of Soluble Starch Synthases from Maize Endosperm. Archives of Biochemistry and Biophysics, vol. 373, No. 1, pp. 135-146.
Devalle et al. (2005) Soluble starch synthase I: a major determinant for the synthesis of amylopectin in *Arabidopsis thaliana* leaves. The Plant Journal, 43, 398-412.
Denyer et al. (1996) The Major Form of ADP-Glucose Pyrophosphorylase in Maize Endosperm Is Extra-Plastidial. Plant Physiol. 112: 779-785.
Fujita et al. (1999) Grain and Starch Characteristics of the Double Recessive Lines for Amylose-free and High Amylose Gene in Barley. Breeding Science 49: 217-219.
Fujita et al. (2006) Function and Characterization of Starch Synthase 1 Using Mutants in Rice. Plant Physiology, vol. 140, pp. 1070-1084.

Fujita et al. (2007) Characterization of SSIIIa-Deficient Mutants of Rice: The Function of SSIIIa and Pleiotropic Effects by SSIIIa Deficiency in the Rice Endosperm. Plant Physiology, 144: 2009-2023.
Hedman and Royer (1982) Gene Dosage at the amylose-extender Locus of Maize: Effects on the Levels of Starch Branching Enzymes. Biochemical Genetics, 20: 483-492.
Hirose and Terao (2004) A comprehensive expression analysis of the starch synthase gene family in rice (*Oryza sativa* L.). Planta, 220: 9-16.
James et al. (2003) Starch synthesis in the cereal endosperm. Current Opinion in Plant Biology, 6:215-222.
Jane et al. (1999) Effects of Amylopectin Branch Chain Length and Amylose Content on the Gelatinization and Pasting Properties of Starch. Cereal Chem. 76(5):629-637.
Kim et al. (2003) Physicochemical Properties and End-use Quality of Wheat Starch as a Function of Waxy Protein Alleles. Journal of Cereal Science, 37: 195-204.
Kossman and Lloyd (2010) Understanding and Influencing Starch Biochemistry. Critical Reviews in Plant Sciences, 19:3, 171-226.
Li et al. (2000) The Structure and Expression of the Wheat Starch Synthase III Gene. Motifs in the Expressed Gene Define the Lineage of the Starch Synthase III Gene Family. Plant Physiology, 123: 613-624.
Li et al. (2003) The structural organisation of the gene encoding class II starch synthase of wheat and barley and the evolution of the genes encoding starch synthases in plants. Funct Integr Genomics, 3:76-85.
Li et al. (2011) The barley amo1 locus is tightly linked to the starch synthase IIIa gene and negatively regulates expression of granule-bound starch synthetic genes. Journal of Experimental Botany, 62: 5217-5231.
Maddelein et al. (1994) Toward an Understanding of the Biogenesis the Starch Granule. The Journal of Biological Chemistry, vol. 269, No. 40, pp. 25150-25157.
Mizuno et al. (1992) Starch Branching Enzymes from Immature Rice Seeds. J. Biochem. 112, 643-65.
Morell et al. (2001) Wheat starch biosynthesis. Euphytica, 119: 55-58.
Morell et al. (2003) Advances in the Understanding of Starch Synthesis in Wheat and Barley. J. Appl. Glycosci., 50, 217-224.
Morell et al. (2006) Control of starch biosynthesis in vascular plants and algae. In: Plaxton WC, McManus MT (eds) Control of. primary metabolism in plants. Annual Plant Reviews, vol. 22, Blackwell, Oxford, pp. 258-289.
Newman et al. (1978) Comparative Nutritive Value of Glacier and High Amyliose Glacier Barleys. Journal of Animal Science, 47:448-456.
Ohdan et al. (2005) Expression profiling of genes involved in starch synthesis in sink and source organs of rice. Journal of Experimental Botany, vol. 56, No. 422, pp. 3229-3244.
Rahman et al. (2000) Genetic Alteration of Starch Functionality in Wheat. Journal of Cereal Science, 31: 91-110.
Sestili et al. (2010) Increasing the amylose content of durum wheat through silencing of the SBEIIa genes. BMC Plant Biol. 10:144, pp. 1-12.
Topping et al. (2003) Resistant Starch and Health—*Himalaya 292*, a Novel Barley Cultivar to Deliver Benefits to Consumers. Starch/Stärke, 55:539-545.
Yamamori and Quynh (2000) Differential effects of Wx-Al, -Bl and-D1 protein deficiencies on apparent amylose content and starch pasting properties in common wheat. Theor Appl Genet, 100:32-38.
Yasui et al. (1996) Amylose and Lipid Contents, Amylopectin Stricture, and Gelatinisation Properties of Waxy Wheat (*Triticum aestivum*) Starch. Journal of Cereal Science 24: 131-137.
Zhang et al. (2005) Mutations Affecting Starch Synthase III in *Arabidopsis* Alter Leaf Starch Structure and Increase the Rate of Starch Synthesis. Plant Physiology, vol. 138, pp. 663-674.
Zhang et al. (2008) Overlapping functions of the starch synthases SSII and SSIII in amylopectin biosynthesis in *Arabidopsis*. BMC Plant Biology 8:96, pp. 1-18.
File History of U.S. Patent Application Publication No. 2013-0156924, Morell et al., published Jun. 20, 2013.

(56) References Cited

OTHER PUBLICATIONS

Mar. 1, 2013 European Search Report and Opinion, issued in connection with European Patent Application No. 10803742.5.

Sep. 27, 2013 Response, filed in connection with European Patent Application No. 10803742.5.

Arnold CN. (2005) Molecular pathogenesis of colorectal cancer, 2005, Cancer, vol. 104, pp. 2035-2047.

Banks et al. (1974) Studies on Starches of High Amylose Content, Starch 26: 289-300.

Boren et al. (2008) Molecular and physicochemical characterization of the high-amylose barley mutant Amo1. Journal of Cereal Science, 47(1): 79-89.

Green et al. (1997) Grain Development Mutants of Barley, α-Amylase Production during Grain Maturation and Its Relation to Endogenous Gibberellic Acid Content. Plant Physiol. 114:203-212.

Kucharska et al. (1998) Estimation of induced mutation rates of four esterase genes in barley (*Hordeum vulgare* L.). J. Appl. Genet. 39(2): 141-145.

Rasmussen et al. (1998) Identification of two low-phytate barley (*Hordeum vulgare* L.) grain mutants by TLC and genetic analysis. Hereditas, 129: 107-112.

Regina et al. (2012) Differential effects of genetically distinct mechanisms of elevating amylose on barley starch characteristics. Carbohydrate Polymers, 89(3):979-991.

File History of U.S. Patent Application Publication No. 2011-0281818, Jenkins et al., published Nov. 17, 2011.

File History of U.S. Patent Application Publication No. 2011-0045127, Ral et al., published Feb. 24, 2011.

Mar. 30, 2020 Written Submissions filed in connection with Indian patent application No. 1144/DELNP/2012.

Nov. 13, 2019 Response to Examiner's Report filed in connection with Canadian patent application No. 2769311.

Sep. 7, 2019 Intention to stay proceedings due to a referral to the Enlarged Board of Appeal issued in connection with European patent application No. 10803742.5.

Behall, K. M., et al. (2006). Consumption of both resistant starch and β-glucan improves postprandial plasma glucose and insulin in women. Diabetes care, 29(5), 976-981.

* cited by examiner

SEQUENCE LISTING

<160> NUMBER OF SEQ ID NOS: 11

<210> SEQ ID NO 1
<211> LENGTH: 2972
<212> TYPE: DNA

<213> ORGANISM: Hordeum vulgare

<400> SEQUENCE: 1

| | | | | | |
|---|---|---|---|---|---|
| cctcgaggtg | cgtttacccc | acacagagta | cactccaact | ccagtccaat | ccagcccact | 60 |
| gccgcttctg | cccgcccatc | gtaccgtcgc | ccgccccgat | cccggccgcc | gccatgtcgt | 120 |
| cggcggtcgc | gtccccgcg | tccttcctcg | cgctcgcgtc | cgcctcgccc | gggagatcat | 180 |
| cacggaggag | ggcgagggtg | ggcgcgtcgc | caacccgcgc | tggggccggc | aggctgcaat | 240 |
| ggcggccgtc | gccgctgcag | cgcacggctc | gcgacggagc | ggtggccgcg | cgcgccgccg | 300 |
| ggatcgacga | cgccgcgccc | ggtaggcagc | cccgcgctcg | ccgctatggc | gccgccacca | 360 |
| aggtcgcgga | tcccgtcaag | acgctcgatc | gcgacgccgc | ggaaggtggt | gggccgtccc | 420 |
| cgccggcacc | gaggcaggac | gccgcccgtc | tgccgagtaa | gaacggcacg | ctgatcaacg | 480 |
| gtgagaacaa | acctaccggc | ggcggtggcg | cgactaaaga | cagcgggctg | cccacacccg | 540 |
| cacgcgcgcc | ccatctgtca | atccagaaca | gagtaccggt | gaacggtgaa | aacaaacata | 600 |
| aggtcgcctc | gccgccgacc | agcatagtgg | atgtcgcgtc | tccgggttcc | gcagctaaca | 660 |
| tttccatcag | taacaaggtg | ccgccgtccg | ttgtcccagc | caagaagacg | ccgccgtcgt | 720 |
| ccgttttccc | ggccaagaag | acgctgccgt | cgtccggctc | aaattttgtg | tcctcggcct | 780 |
| ctgctcccag | gctggacact | gtcagcgatg | tggaacttgc | acagaagaag | gatgcgctga | 840 |
| ttgtcaaaga | agctccaaaa | ccaaaggctc | tttcggcccc | tgcagccccc | gctgtacaag | 900 |
| aagacctttg | ggatttcaag | aaatacattg | gtttcgagga | gcccgtggag | gccaaggatg | 960 |
| atggctcggc | tgttgcagat | gatgcgggtt | cctttgaaca | tcaccagaat | catgattccg | 1020 |
| gacctttggc | aggggagaac | gtcatgaacg | tggtcgtcgt | tgctgctgaa | tgttctccct | 1080 |
| ggtgcaaaac | aggtggtctt | ggagatgttg | cgggtgcttt | gcccaaggct | ttggctaaga | 1140 |
| gaggacatcg | tgttatggtt | gtggtaccaa | ggtatgggga | ctatgaggaa | gcctacgatg | 1200 |
| tcggagtccg | aaaatactac | aaggctgctg | gacaggatat | ggaagtgaat | tatttccatg | 1260 |
| cttatatcga | tggagtggat | tttgtgttca | ttgacgctcc | tctcttccga | caccgtcagc | 1320 |
| aagacattta | tgggggcagc | agacaggaaa | ttatgaagcg | catgattttg | ttctgcaagg | 1380 |
| ccgctgtcga | ggttccttgg | cacgttccat | gcggcggtgt | cccttacggg | gatggaaatc | 1440 |
| tggtcttcat | tgcaaatgat | tggcacacgg | cactcctgcc | tgtctatctg | aaagcatatt | 1500 |
| acagggacca | tggtttgatg | caatacagtc | gctccgttat | ggtgatacat | aacatcgctc | 1560 |
| accagggccg | tggccctgta | gatgaattcc | cgttcaccga | gttgcctgag | cactacctgg | 1620 |
| aacacttcag | actgtacgac | cccgtcggcg | gtgagcacgc | caactacttc | gccgccggcc | 1680 |
| tgaagatggc | ggaccaggtt | gtcgtcgtga | gccccgggta | cctgtgggag | ctgaagacgg | 1740 |
| tggagggcgg | ctgggggctt | cacgacatca | tacggcagaa | cgactggaag | acccgcggca | 1800 |
| tcgtgaacgg | catcgacaac | atggagtgga | accctgaggt | ggacgtccac | ctgaagtcgg | 1860 |
| acggctacac | caacttctcc | ctgaagacgc | tggactccgg | caagcggcag | tgcaaggagg | 1920 |
| ccctgcagcg | cgagctgggg | ctgcaggtcc | gcggcgacgt | gccgctgctc | gggttcatcg | 1980 |
| gcggctgga | cgggcagaag | ggcgtggaga | tcatcgcgga | cgcgatgccc | tggatcgtga | 2040 |
| gccaggacgt | gcagctggtg | atgctgggca | cggggcgcca | cgacctggag | agcatgctgc | 2100 |
| agcacttcga | gcgggagcac | cacgacaagg | tgcgcgggtg | ggtgggggttc | tccgtgcgcc | 2160 |
| tggcgcaccg | gatcacggcg | ggcgccgacg | cgctcctcat | gccctcccgg | ttcgagccgt | 2220 |
| gcgggctgaa | ccagctctac | gcgatggcct | acggcaccat | ccctgtcgtg | cacgccgtcg | 2280 |

```
gcggcttgag ggataccgtg ccgccgttcg acccccttcaa ccactccggg ctcgggtgga   2340
cgttcgaccg cgccgaggcg cacaagctga tcgaggcgct cgggcactgc ctccgcacct   2400
accgggacca aaggagagc tggaggggcc tccaggagcg cggcatgtcg caggacttca   2460
```
```
gcggcttgag ggataccgtg ccgccgttcg acccccttcaa ccactccggg ctcgggtgga   2340
cgttcgaccg cgccgaggcg cacaagctga tcgaggcgct cgggcactgc ctccgcacct   2400
accgggacca aaggagagc tggaggggcc tccaggagcg cggcatgtcg caggacttca   2460
gctgggaaca tgccgccaag ctctacgagg acgtcctcgt ccaggccaag taccagtggt   2520
gaacgctgct acccggtcca gccccgcatg cgtgcatgag aggatggaaa tgcgcattgc   2580
gcacttgcag atttggcgca cgcaggaacg tgccgtcctt cttgatgaga acgccggcat   2640
ccgcgaggtt gagacgctga ttccgatctg gtccgtcgca gagtagagtg aaacgctcct   2700
tgttgcaggt atatgggaat gtttttttttc cttttttttt gcgagggagg tatatgggaa   2760
tgttaacttg gtattgtaat gtggtatgct gtgtgcatta ttacatcggt tgttgttgct   2820
tattcttgct agctaagtcg gaggccaaga gcgaaagcta gctcacatgt ctgatgtatg   2880
caagtgacat ggttggtttg gttgtgcagt gcaaacggca ggaatgggaa gtgaattcct   2940
ccctgcttaa attaaaaaaa aaaaaaaaaa aa   2972
```

<210> SEQ ID NO 2
<211> LENGTH: 802
<212> TYPE: PRT
<213> ORGANISM: Hordeum vulgare

<400> SEQUENCE: 2

```
Met Ser Ser Ala Val Ala Ser Pro Ala Ser Phe Leu Ala Leu Ala Ser
1               5                   10                  15

Ala Ser Pro Gly Arg Ser Arg Arg Ala Arg Val Gly Ala Ser
        20                  25                  30

Pro Thr Arg Ala Gly Ala Gly Arg Leu Gln Trp Arg Pro Ser Pro Leu
        35                  40                  45

Gln Arg Thr Ala Arg Asp Gly Val Ala Ala Arg Ala Ala Gly Ile
    50                  55                  60

Asp Asp Ala Ala Pro Gly Arg Gln Pro Arg Ala Arg Arg Tyr Gly Ala
65                  70                  75                  80

Ala Thr Lys Val Ala Asp Pro Val Lys Thr Leu Asp Arg Asp Ala Ala
                85                  90                  95

Glu Gly Gly Gly Pro Ser Pro Ala Pro Arg Gln Asp Ala Ala Arg
                100                 105                 110

Leu Pro Ser Lys Asn Gly Thr Leu Ile Asn Gly Glu Asn Lys Pro Thr
        115                 120                 125

Gly Gly Gly Gly Ala Thr Lys Asp Ser Gly Leu Pro Thr Pro Ala Arg
    130                 135                 140

Ala Pro His Leu Ser Ile Gln Asn Arg Val Pro Val Asn Gly Glu Asn
145                 150                 155                 160

Lys His Lys Val Ala Ser Pro Pro Thr Ser Ile Val Asp Val Ala Ser
                165                 170                 175

Pro Gly Ser Ala Ala Asn Ile Ser Ile Ser Asn Lys Val Pro Pro Ser
        180                 185                 190

Val Val Pro Ala Lys Lys Thr Pro Ser Ser Val Phe Pro Ala Lys
        195                 200                 205

Lys Thr Leu Pro Ser Ser Gly Ser Asn Phe Val Ser Ser Ala Ser Ala
    210                 215                 220

Pro Arg Leu Asp Thr Val Ser Asp Val Glu Leu Ala Gln Lys Lys Asp
225                 230                 235                 240

Ala Leu Ile Val Lys Glu Ala Pro Lys Pro Lys Ala Leu Ser Ala Pro
```

-continued

```
                245                 250                 255
Ala Ala Pro Ala Val Gln Glu Asp Leu Trp Asp Phe Lys Lys Tyr Ile
            260                 265                 270
Gly Phe Glu Glu Pro Val Glu Ala Lys Asp Asp Gly Ser Ala Val Ala
            275                 280                 285
Asp Asp Ala Gly Ser Phe Glu His His Gln Asn His Asp Ser Gly Pro
            290                 295                 300
Leu Ala Gly Glu Asn Val Met Asn Val Val Val Ala Ala Glu Cys
305                 310                 315                 320
Ser Pro Trp Cys Lys Thr Gly Gly Leu Gly Asp Val Ala Gly Ala Leu
                325                 330                 335
Pro Lys Ala Leu Ala Lys Arg Gly His Arg Val Met Val Val Val Pro
                340                 345                 350
Arg Tyr Gly Asp Tyr Glu Glu Ala Tyr Asp Val Gly Val Arg Lys Tyr
                355                 360                 365
Tyr Lys Ala Ala Gly Gln Asp Met Glu Val Asn Tyr Phe His Ala Tyr
            370                 375                 380
Ile Asp Gly Val Asp Phe Val Phe Ile Asp Ala Pro Leu Phe Arg His
385                 390                 395                 400
Arg Gln Gln Asp Ile Tyr Gly Gly Ser Arg Gln Glu Ile Met Lys Arg
                405                 410                 415
Met Ile Leu Phe Cys Lys Ala Ala Val Glu Val Pro Trp His Val Pro
                420                 425                 430
Cys Gly Gly Val Pro Tyr Gly Asp Gly Asn Leu Val Phe Ile Ala Asn
                435                 440                 445
Asp Trp His Thr Ala Leu Leu Pro Val Tyr Leu Lys Ala Tyr Tyr Arg
            450                 455                 460
Asp His Gly Leu Met Gln Tyr Ser Arg Ser Val Met Val Ile His Asn
465                 470                 475                 480
Ile Ala His Gln Gly Arg Gly Pro Val Asp Glu Phe Pro Phe Thr Glu
                485                 490                 495
Leu Pro Glu His Tyr Leu Glu His Phe Arg Leu Tyr Asp Pro Val Gly
                500                 505                 510
Gly Glu His Ala Asn Tyr Phe Ala Ala Gly Leu Lys Met Ala Asp Gln
                515                 520                 525
Val Val Val Ser Pro Gly Tyr Leu Trp Glu Leu Lys Thr Val Glu
                530                 535                 540
Gly Gly Trp Gly Leu His Asp Ile Ile Arg Gln Asn Asp Trp Lys Thr
545                 550                 555                 560
Arg Gly Ile Val Asn Gly Ile Asp Asn Met Glu Trp Asn Pro Glu Val
                565                 570                 575
Asp Val His Leu Lys Ser Asp Gly Tyr Thr Asn Phe Ser Leu Lys Thr
            580                 585                 590
Leu Asp Ser Gly Lys Arg Gln Cys Lys Glu Ala Leu Gln Arg Glu Leu
            595                 600                 605
Gly Leu Gln Val Arg Gly Asp Val Pro Leu Leu Gly Phe Ile Gly Arg
            610                 615                 620
Leu Asp Gly Gln Lys Gly Val Glu Ile Ile Ala Asp Ala Met Pro Trp
625                 630                 635                 640
Ile Val Ser Gln Asp Val Gln Leu Val Met Leu Gly Thr Gly Arg His
                645                 650                 655
Asp Leu Glu Ser Met Leu Gln His Phe Glu Arg Glu His His Asp Lys
            660                 665                 670
```

Val Arg Gly Trp Val Gly Phe Ser Val Arg Leu Ala His Arg Ile Thr
            675                 680                 685

Ala Gly Ala Asp Ala Leu Leu Met Pro Ser Arg Phe Glu Pro Cys Gly
        690                 695                 700

Leu Asn Gln Leu Tyr Ala Met Ala Tyr Gly Thr Ile Pro Val Val His
705                 710                 715                 720

Ala Val Gly Gly Leu Arg Asp Thr Val Pro Pro Phe Asp Pro Phe Asn
                725                 730                 735

His Ser Gly Leu Gly Trp Thr Phe Asp Arg Ala Glu Ala His Lys Leu
            740                 745                 750

Ile Glu Ala Leu Gly His Cys Leu Arg Thr Tyr Arg Asp His Lys Glu
        755                 760                 765

Ser Trp Arg Gly Leu Gln Glu Arg Gly Met Ser Gln Asp Phe Ser Trp
    770                 775                 780

Glu His Ala Ala Lys Leu Tyr Glu Asp Val Leu Val Gln Ala Lys Tyr
785                 790                 795                 800

Gln Trp

<210> SEQ ID NO 3
<211> LENGTH: 23
<212> TYPE: DNA
<213> ORGANISM: Hordeum vulgare

<400> SEQUENCE: 3
cctggaacac ttcagactgt acg                                              23

<210> SEQ ID NO 4
<211> LENGTH: 22
<212> TYPE: DNA
<213> ORGANISM: Hordeum vulgare

<400> SEQUENCE: 4
agcatcacca gctgcacgtc ct                                               22

<210> SEQ ID NO 5
<211> LENGTH: 38
<212> TYPE: DNA
<213> ORGANISM: Hordeum vulgare

<400> SEQUENCE: 5
cacgacgttg taaaacgaca cttaagtgcc atgcaaag                              38

<210> SEQ ID NO 6
<211> LENGTH: 19
<212> TYPE: DNA
<213> ORGANISM: Hordeum vulgare

<400> SEQUENCE: 6
agggacaaaa atggctaag                                                   19

<210> SEQ ID NO 7
<211> LENGTH: 17
<212> TYPE: DNA
<213> ORGANISM: Triticum aestivum

<400> SEQUENCE: 7
ggaggtctcg gggatgt                                                     17

<210> SEQ ID NO 8

```
<211> LENGTH: 23
<212> TYPE: DNA
<213> ORGANISM: Triticum aestivum

<400> SEQUENCE: 8
gctccaggaa gtaaacggtc agg                                              23

<210> SEQ ID NO 9
<211> LENGTH: 2946
<212> TYPE: DNA
<213> ORGANISM: Hordeum vulgare

<400> SEQUENCE: 9
gtgcgtttac cccacacaga gtacactcca actccagtcc agtccagccc actgccgctt      60
ctgcccgccc atcgtaccgt cgcccgcccc gatcccggcc gccgccatgt cgtcggcggt     120
cgcgtccccc gcgtccttcc tcgcgctcgc gtccgcctcg cccgggagat catcacggag     180
gagggcgagg gtgggcgcgt cgccaacccg cgctggggcc ggcaggctgc aatggcggcc     240
gtcgccgctg cagcgcacgg ctcgcgacgg agcggtggcc gcgcgcgccg ccgggatcga     300
cgacgccgcg cccggtaggc agccccgcgc tcgccgctat ggcgccgcca ccaaggtcgc     360
ggatcccgtc aagacgctcg atcgcgacgc gcggaaggt ggtgggccgt ccccgccggc      420
accgaggcag gacgccgccc gtctgccgag taagaacggc acgctgatca acggtgagaa     480
caaacctacc ggcggcggtg gcgcgactaa agacagcggg ctgcccacac ccgcacgcgc     540
gccccatctg tcaatccaga acagagtacc ggtgaacggt gaaaacaaac ataaggtcgc     600
ctcgccgccg accagcatag tggatgtcgc gtctccgggt tccgcagcca acatttccat     660
cagtaacaag gtgccgccgt ccgttgtccc agccaagaag acgccgccgt cgtccgtttt     720
cccggccaag aaggcgccgc cgtcgtccgt tgtcccggcc aagaagacgc tgccgtcgtc     780
cggctcaaat tttgtgtcct cggcctctgc tcccaggctg gacactgtca gcgatgtgga     840
acttgcacag aagaaggatg cgctgattgt caaagaagct ccaaaaccaa aggctctttc     900 ggccctgca gccccgctg tacaagaaga cctttgggat ttcaagaaat acattggttt       960
cgaggagccc gtggaggcca aggatgatgg ctcggctgtt gcagatgatg cgggttcctt    1020
tgaacatcac cagaatcatg attccggacc tttggcaggg gagaacgtca tgaacgtggt    1080
cgtcgttgct gctgaatgtt ctccctggtg caaaacaggt ggtcttggag atgttgcggg    1140
tgctttgccc aaggctttgg ctaagagagg acatcgtgtt atggttgtgg taccaaggta    1200
tggggactat gaggaagcct acgatgtcgg agtccgaaaa tactacaagg ctgctggaca    1260
ggatatggaa gtgaattatt ccatgcttta tatcgatgga gtggattttg tgttcattga    1320
cgctcctctc ttccgacacc gtcagcaaga catttatggg ggcagcagac aggaaaattat   1380 gaagcgcatg attttgttct gcaaggccgc tgtcgaggtt ccttggcacg ttccatgcgg    1440
cggtgtccct tacggggatg gaaatctggt cttcattgca aatgattggc acacggcact    1500
cctgcctgtc tatctgaaag catattacag ggaccatggt tgatgcaat acagtcgctc     1560 cgttatggtg atacataaca tcgctcacca gggccgtggc cctgtagatg aattcccgtt    1620
caccgagttg cctgagcact acctggaaca cttcagactg tacgaccccg tcggcggtga    1680
gcacgccaac tacttcgccg ccggcctgaa gatggcggac caggttgtcg tcgtgagccc    1740
cgggtacctg tgggagctga gacggtgga gggcggctgg gggcttcacg acatcatacg     1800
gcagaacgac tggaagaccc gcggcatcgt gaacggcatc gacaacatgg agtgaaaccc    1860
tgaggtggac gtccacctga agtcggacgg ctacaccaac ttctccctga agacgctgga    1920
```

```
ctccggcaag cggcagtgca aggaggccct gcagcgcgag ctggggctgc aggtccgcgg   1980
cgacgtgccg ctgctcgggt tcatcgggcg gctggacggg cagaagggcg tggagatcat   2040
cgcggacgcg atgccctgga tcgtgagcca ggacgtgcag ctggtgatgc tgggcacggg   2100
gcgccacgac ctggagagca tgctgcagca cttcgagcgg gagcaccacg acaaggtgcg   2160
cgggtgggtg gggttctccg tgcgcctggc gcaccggatc acggcgggcg ccgacgcgct   2220
cctcatgccc tcccggttcg agccgtgcgg gctgaaccag ctctacgcga tggcctacgg   2280
caccatccct gtcgtgcacg ccgtcggcgg cctgagggat accgtgccgc cgttcgaccc   2340
cttcaaccac tccgggctcg ggtggacgtt cgaccgcgcc gaggcgcaca gctgatcga   2400 ggcgctcggg cactgcctcc gcacctaccg ggaccacaag gagagctgga ggggcctcca   2460
ggagcgcggc atgtcgcagg acttcagctg gaacatgcc gccaagctct acgaggacgt   2520
cctcgtccag gccaagtacc agtggtgaac gctgctaccc ggtccagccc cgcatgcgtg   2580
catgagagga tggaaatgcg cattgcgcac ttgcagattt ggcgcacgca ggaacgtgcc   2640
gtccttcttg atgagaacgc cggcatccgc gaggttgaga cgctgattcc gatctggtcc   2700
gtcgcagagt agagtgaaac gctccttgtt gcaggtatat gggaatgttt ttttccttt   2760 tttttgcga gggaggtata tgggaatgtt aacttggtat tgtaatgtgg tatgctgtgt   2820
gcattattac atcggttgtt gttgcttatt cttgctagct aagtcggagg ccaagagcga   2880
aagctagctc acatgtctga tgtatgcaag tgacatggtt ggtttggttg tgcagtgcaa   2940
acggca                                                              2946
```

<210> SEQ ID NO 10
<211> LENGTH: 571
<212> TYPE: PRT
<213> ORGANISM: Hordeum vulgare

<400> SEQUENCE: 10

```
Met Ser Ser Ala Val Ala Ser Pro Ala Ser Phe Leu Ala Leu Ala Ser
1               5                   10                  15

Ala Ser Pro Gly Arg Ser Ser Arg Arg Ala Arg Val Gly Ala Ser
            20                  25                  30

Pro Thr Arg Ala Gly Ala Gly Arg Leu Gln Trp Arg Pro Ser Pro Leu
        35                  40                  45

Gln Arg Thr Ala Arg Asp Gly Ala Val Ala Ala Ala Ala Gly Ile
    50                  55                  60

Asp Asp Ala Ala Pro Gly Arg Gln Pro Arg Ala Arg Arg Tyr Gly Ala
65                  70                  75                  80

Ala Thr Lys Val Ala Asp Pro Val Lys Thr Leu Asp Arg Asp Ala Ala
                85                  90                  95

Glu Gly Gly Gly Pro Ser Pro Ala Pro Arg Gln Asp Ala Ala Arg
            100                 105                 110

Leu Pro Ser Lys Asn Gly Thr Leu Ile Asn Gly Glu Asn Lys Pro Thr
        115                 120                 125

Gly Gly Gly Gly Ala Thr Lys Asp Ser Gly Leu Pro Thr Pro Ala Arg
    130                 135                 140

Ala Pro His Leu Ser Ile Gln Asn Arg Val Pro Val Asn Gly Glu Asn
145                 150                 155                 160

Lys His Lys Val Ala Ser Pro Thr Ser Ile Val Asp Val Ala Ser
                165                 170                 175

Pro Gly Ser Ala Ala Asn Ile Ser Ile Ser Asn Lys Val Pro Pro Ser
```

```
                180             185             190
Val Val Pro Ala Lys Lys Thr Pro Pro Ser Ser Val Phe Pro Ala Lys
            195             200             205
Lys Thr Leu Pro Ser Ser Gly Ser Asn Phe Val Ser Ser Ala Ser Ala
            210             215             220
Pro Arg Leu Asp Thr Val Ser Asp Val Glu Leu Ala Gln Lys Lys Asp
225             230             235             240
Ala Leu Ile Val Lys Glu Ala Pro Lys Pro Lys Ala Leu Ser Ala Pro
            245             250             255
Ala Ala Pro Ala Val Gln Glu Asp Leu Trp Asp Phe Lys Lys Tyr Ile
            260             265             270
Gly Phe Glu Glu Pro Val Glu Ala Lys Asp Asp Gly Ser Ala Val Ala
            275             280             285
Asp Asp Ala Gly Ser Phe Glu His His Gln Asn His Asp Ser Gly Pro
            290             295             300
Leu Ala Gly Glu Asn Val Met Asn Val Val Val Ala Ala Glu Cys
305             310             315             320
Ser Pro Trp Cys Lys Thr Gly Gly Leu Gly Asp Val Ala Gly Ala Leu
            325             330             335
Pro Lys Ala Leu Ala Lys Arg Gly His Arg Val Met Val Val Val Pro
            340             345             350
Arg Tyr Gly Asp Tyr Glu Glu Ala Tyr Asp Val Gly Val Arg Lys Tyr
            355             360             365
Tyr Lys Ala Ala Gly Gln Asp Met Glu Val Asn Tyr Phe His Ala Tyr
            370             375             380
Ile Asp Gly Val Asp Phe Val Phe Ile Asp Ala Pro Leu Phe Arg His
385             390             395             400
Arg Gln Gln Asp Ile Tyr Gly Gly Ser Arg Gln Glu Ile Met Lys Arg
            405             410             415
Met Ile Leu Phe Cys Lys Ala Ala Val Glu Val Pro Trp His Val Pro
            420             425             430
Cys Gly Gly Val Pro Tyr Gly Asp Gly Asn Leu Val Phe Ile Ala Asn
            435             440             445
Asp Trp His Thr Ala Leu Leu Pro Val Tyr Leu Lys Ala Tyr Tyr Arg
            450             455             460
Asp His Gly Leu Met Gln Tyr Ser Arg Ser Val Met Val Ile His Asn
465             470             475             480
Ile Ala His Gln Gly Arg Gly Pro Val Asp Glu Phe Pro Phe Thr Glu
            485             490             495
Leu Pro Glu His Tyr Leu Glu His Phe Arg Leu Tyr Asp Pro Val Gly
            500             505             510
Gly Glu His Ala Asn Tyr Phe Ala Ala Gly Leu Lys Met Ala Asp Gln
            515             520             525
Val Val Val Ser Pro Gly Tyr Leu Trp Glu Leu Lys Thr Val Glu
            530             535             540
Gly Gly Trp Gly Leu His Asp Ile Ile Arg Gln Asn Asp Trp Lys Thr
545             550             555             560
Arg Gly Ile Val Asn Gly Ile Asp Asn Met Glu
            565             570

<210> SEQ ID NO 11
<211> LENGTH: 230
<212> TYPE: PRT
<213> ORGANISM: Hordeum vulgare
```

```
<400> SEQUENCE: 11

Asn Pro Glu Val Asp Val His Leu Lys Ser Asp Gly Tyr Thr Asn Phe
1               5                   10                  15

Ser Leu Lys Thr Leu Asp Ser Gly Lys Arg Gln Cys Lys Glu Ala Leu
            20                  25                  30

Gln Arg Glu Leu Gly Leu Gln Val Arg Gly Asp Val Pro Leu Leu Gly
        35                  40                  45

Phe Ile Gly Arg Leu Asp Gly Gln Lys Gly Val Glu Ile Ile Ala Asp
    50                  55                  60

Ala Met Pro Trp Ile Val Ser Gln Asp Val Gln Leu Val Met Leu Gly
65                  70                  75                  80

Thr Gly Arg His Asp Leu Glu Ser Met Leu Gln His Phe Glu Arg Glu
                85                  90                  95

His His Asp Lys Val Arg Gly Trp Val Gly Phe Ser Val Arg Leu Ala
                100                 105                 110

His Arg Ile Thr Ala Gly Ala Asp Ala Leu Leu Met Pro Ser Arg Phe
            115                 120                 125

Glu Pro Cys Gly Leu Asn Gln Leu Tyr Ala Met Ala Tyr Gly Thr Ile
    130                 135                 140

Pro Val Val His Ala Val Gly Gly Leu Arg Asp Thr Val Pro Pro Phe
145                 150                 155                 160

Asp Pro Phe Asn His Ser Gly Leu Gly Trp Thr Phe Asp Arg Ala Glu
                165                 170                 175

Ala His Lys Leu Ile Glu Ala Leu Gly His Cys Leu Arg Thr Tyr Arg
            180                 185                 190

Asp His Lys Glu Ser Trp Arg Gly Leu Gln Glu Arg Gly Met Ser Gln
            195                 200                 205

Asp Phe Ser Trp Glu His Ala Ala Lys Leu Tyr Glu Asp Val Leu Val
    210                 215                 220

Gln Ala Lys Tyr Gln Trp
225                 230
```

BARLEY AND USES THEREOF

CROSS-REFERENCE TO RELATED APPLICATIONS

This application is a divisional of U.S. application Ser. No. 13/387,973, filed Feb. 7, 2012, a § 371 national stage of PCT International Application No. PCT/AU2010/000968, filed Jul. 30, 2010, claiming priority of Australian Patent Application No. 2009903563, filed Jul. 30, 2009, the contents of each of which are hereby incorporated by reference in their entirety.

REFERENCE TO A SEQUENCE LISTING

This application incorporates-by-reference nucleotide and/or amino acid sequences which are present in the file named "181212_83759-Z_Substitute_Sequence_ Listing_CAS.txt", which is 22.4 kilobytes in size, and which was created Dec. 12, 2018 in the IBM-PC machine format, having an operating system compatibility with MS-Windows, which is contained in the text file filed Dec. 12, 2018 as part of this application.

FIELD

The present specification describes variant barley plants and grain therefrom comprising a reduced level or activity of SSIIa protein and exhibiting desirable starch and non-starch components in relatively high yield.

BACKGROUND

Wildtype barley seed contains approximately 50 to 60% of starch, contained in its endosperm, that has approximately 25% amylose and 75% amylopectin. Amylose is a mostly linear α-(1-4) linked glucosyl chain with a few α-(1-6) linked glucan chains and has a molecular weight of $10^4$ to $10^5$. Amylopectin is a highly branched glucan in which α-(1-4) linked glucosyl chains with mostly 3 to 60 glucosyl units are connected by α-(1,6)-linkages, so that approximately 5-6% of the glucosyl linkages are α-(1,6)-linkages, and has a molecular weight of $10^5$ to $10^6$.

A suite of enzymes are involved in cereal starch biosynthesis including ADP-glucose pyrophosphorylases (EC 2.7.7.27), starch synthases (EC 2.4.1.21), starch branching enzymes (EC 2.4.1.18) and starch debranching enzymes (EC 3.2.1.41 and 3.2.1.68). The first committed step of starch synthesis is synthesis of ADP-glucose from Glucose-1-P and ATP, catalysed by the enzyme ADP-glucose pyrophosphorylase. The ADP-glucose is then used as substrate for the synthesis of starch by starch synthases which transfer glucose to the non-reducing end of pre-existing α-(1-4) linked glucosyl chain of starch. The branched glucan chains of starch, linked with α-(1-6) linkages, are formed by starch branching enzymes through the cleavage of a region of the α-(1-4) linkage glucan and subsequent transfer of the short glucan to a position on the α-(1-4) linkage glucan of starch. Excess α-(1-6) linked glucan chains are removed by debranching enzymes to maintain starch in a defined structure (See reviews from Kossmann and Lloyd, *Crit Rev Plant Sci*, 19: 171-226, 2000; Rahman et al., *J Cereal Sci*, 31: 91-110, 2000; Smith, *Biomacromolecules*, 2: 335-341, 2001; Morell et al., *Euphytica*, 119: 55-58, 2001; Morell et al., *J Appl Glycosci*, 50: 217-224, 2003a; Morell et al., Control of starch biosynthesis in vascular plants and algae. In: Plaxton W C, McManus M T (eds) *Control of primary metabolism in plants. Annual plant reviews*, vol 22, Blackwell, Oxford, pp 258-289, 2006; Ball and Morell, *Annu Rev Plant Biol*, 54: 207-233, 2003; James et al., *Curr Opin Plant Biol*, 6: 215-222, 2003; Tetlow et al., *J Exp Bot*, 55: 2131-2145, 2004).

Ten starch synthase genes have been identified in the rice genome (Hirose and Terao, *Planta*, 220: 9-16, 2004) and are grouped into five distinct classes: granule-bound starch synthase (GBSS), starch synthase I (SSI), starch synthase II (SSII), starch synthase III (SSIII) and starch synthase IV (SSIV) (Li et al., *Funct Integr Genomics*, 3: 76-85, 2003). There are two GBSS isoforms (GBSSI and GBSSII), one SSI isoform, three SSII isoforms (SSIIa [SSII-3], SSIIb [SSII-2], and SSIIc [SSII-1]), two SSIII isoforms (SSIIIa [SSIII-2] and SSIIIb [SSIII-1]), and two SSIV isoforms (SSIVa [SSIV-1] and SSIVb [SSIV-2]) in rice (Hirose and Terao, 2004 (supra); Fujita et al., *Plant Physiol*, 144: 2009-2023, 2007). Proteins corresponding to SSI, SSIIa and GBSSI have been detected within starch granules, whereas SSIIIa protein has been only detected in the soluble phase of amyloplastids (Li et al., *Plant Physiology*, 123: 613-624, 2000). The precise role of these starch synthases individually and cooperatively in determining the final structure of the starch granule largely remains undefined although the potential roles of some starch synthases have been characterised in different organs and different species.

Mutants in starch synthases have been useful in determining the roles in some cereal species. GBSSI plays a crucial role in the biosynthesis of amylose (Ball et al., *Cell* 86(3): 349-52, 1996), but it may also contribute to the synthesis of the long chains of amylopectin (Maddelein et al., *J Biol Chem*. 269(40): 25150-7, 1994; Denyer et al., *Plant Physiol*. 112(2):779-85, 1996). The effect on starch properties has been examined for GBSSI null mutants in barley and wheat (Andersson et al., *J. Cereal Sci* 30: 183-191, 1999; Yamamori and Quynh, *Theor Appl Genet*, 100: 32-38, 2000). The GBSSI null mutant barley had less than 5% of the amylose content compared to wild type (Andersson et al., 1999 (supra)). A GBSSI null mutant of wheat also had low amylose content (Kim et al., *J Cereal Sci*, 37: 195-204, 2003; Miura et al., *Euphytica*, 108: 91-95, 1999; Miura et al., *Euphytica*, 123: 353-359, 2002). The GBSSI null mutant wheat also had higher peak gelatinization temperature and enthalpy than that from wildtype as determined by Differential Scanning Calorimetry (DSC) (Yasui et al., *J Cereal Sci*, 24:131-137, 1996).

SSI, SSIIa and SSIII are thought to be primarily involved in amylopectin synthesis involved in the extension of specific subsets of available non-reducing ends within the starch molecule. Studies on *Arabidopsis* and rice SSI null mutants showed that SSI is involved in biosynthesis of the small outer chains of the amylopectin cluster (8-12 dp) in leaf starch of *Arabidopsis* (Delvalle et al., *Plant J*. 43(3): 398-412, 2005) and in the endosperm starch of rice (Fujita et al., *Plant Physiol*. 140: 1070-1084, 2006). Starch from barley and wheat SSIIa mutants had an increase in chains of DP3-8, indicating that the SSIIa enzyme played a role in extending shorter glucan chains of DP3-8 to longer glucan chains of DPl2-35 (Morell et al., *Plant J*. 34: 173-185, 2003b; Yamamori et al., *Theor Appl Genet*, 101: 21-29, 2000; Konik-Rose et al., *Theor Appl Genet*, 115: 1053-1065, 2007). Loss of SSIIIa in maize and rice conferred an increased amylose phenotype, with a reduction in the proportion of very long chains (DP>50 in maize or DP>30 in rice), and slightly reduced gelatinisation temperature (Jane et al., *Cereal Chem*. 76: 629-637, 1999; Fujita et al., 2007 (supra)). *Arabidopsis* mutants, defective for SSIV, appear to have fewer, larger starch granules within the plastid and a role in priming starch granule formation has been postulated for the SSIV protein (Roldan et al., *Plant J.* 49: 492-504, 2007).

A barley SSIIa mutant has been shown to have a high amylose phenotype with reduced starch content and reduced seed weight due to the reduction of starch biosynthesis. The mutant barley lines M292 and M342 which were homozygous for a null mutation in the gene encoding SSIIa were obtained following mutagenesis of grains of the barley variety 'Himalaya' with sodium azide. Mutant seeds were initially selected from progeny grain of the mutagenised population on the basis of a shrunken grain phenotype. The mutant lines were further characterised by their altered starch properties, reduced SSIIa protein level and activity, and genetically by the presence of a premature stop codon in the protein coding region of the gene encoding SSIIa (Morell et al., 2003b (supra) incorporated herein in its entirety by reference). This caused loss of the SSIIa enzyme in the endosperm. However, the SSIIa mutant grain also had substantially reduced starch content and this was associated with a moderate reduction in yield when the barley plants were grown in the field. It was not known if the yield could be improved, or how, while still maintaining the high amylose phenotype.

There is therefore a need for high amylose barley with improved agronomic performance.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a mutation" includes a single mutation, as well as two or more mutations; reference to "an agent" includes one agent, as well as two or more agents; and so forth.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 8. A sequence listing is provided after the claims.

Genes and other genetic material (e.g. mRNA, nucleic acid constructs etc) are represented herein in italics while their proteinaceous expression products are represented in non-italicised form. Thus, for example starch synthase II (SSII) polypeptide is the expression product of SSII nucleic acid sequences.

Representative examples of the nucleic acid and amino acid sequences of SSIIa molecules are provided in the sequence listing further described in Table 8.

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Each embodiments described herein is to be applied mutatis mutandis to each any every embodiment unless specifically stated otherwise.

In one embodiment, the present invention provides barley grain comprising a reduced level or activity of SSIIa protein and a starch content of at least 41% (w/w). The grain, products therefrom and methods of obtaining, identifying or using the grain are characterized by at least these two features. In particular, the "starch content" is the starch content of the wholegrain since the "starch content" of, for example polished grain, will be higher. In some embodiments, the barley grain comprises a starch content of at least 43% (w/w), at least 45% (w/w), at least 47% (w/w), at least 50% (w/w), or comprises a starch content of 41-65% (w/w).

In a related embodiment, the grain comprises an amylose content of at least 50% or at least 60% as a proportion of the total starch in the grain. Further, in some embodiments, the grain comprises a β-glucan content of 5-9% (w/w), or greater than 9% (w/w).

In another embodiment, the grain comprises a fructan content of 3-11% (w/w), or 4-11%. Conveniently, the fructan comprises a degree of polymerization from about 3 to about 12.

In a further related embodiment, the grain comprises a mutation in an endogenous gene encoding a polypeptide with SSIIa activity wherein the mutation reduces the expression of the gene encoding SSIIa in a barley plant or leads to the expression of SSIIa with reduced level or activity. In an illustrative embodiment, a plant or grain that is homozygous for the sex6-292 allele is provided. In some embodiments, the level of SSIIa is reduced by an exogenous nucleic acid molecule which down-regulates the expression of a gene encoding SSIIa in a barley plant. Here, in some embodiments, the exogenous nucleic acid molecule comprises a gene-silencing chimeric gene, an antisense, ribozyme, co-suppression, dsRNA molecule, hairpin RNA molecule or microRNA that down-regulates endogenous SSII expression.

In a preferred embodiment, the present invention provides barley grain further comprises a genetic variation which reduces the activity of an amo1 gene. Conveniently, as described further herein the activity of the amo1 gene is reduced relative to an unmodified control, such as reduction relative to barley grain of the variety Himalaya. In an illustrative embodiment, the genetic variation comprises a mutation in an amo1 gene. In a further example, the plant or grain therefrom is homozygous for the amo1-AC38 allele (Schondelmaier et al., *Plant Breeding*, 109: 274-281, 1992, incorporated herein by reference in its entirety). In an embodiment, the barley grain comprises a mutation in an amo1 gene and a reduced activity of a starch synthase other than SSIIa, preferably a reduced level of GBSS, more preferably a reduced level of GBSSI. The grain may also comprise an increased level of lysine (>4 g per 100 g of protein). Such grain may be obtained by crossing the barley variety Prowashonupana and a barley containing an amo1 mutant locus such as High Amylose Glacier.

The grain may be of any useful form such as, without limitation, wholegrain or cracked, ground, polished, milled, kibbled, rolled or pearled grain.

The present invention extends to a barley plant capable of producing the herein described grains and also to barley wholemeal or flour produced from the grain.

In some embodiments, the present invention provides barley grain comprising a starch content of at least 41% (w/w) wherein the grain comprises a mutant SSIIa and a mutant amo1 gene. In some embodiments, the SSIIa mutation is the sex6-292 allele. In some embodiments, grain comprising a loss of function SSIIa mutation such as the sex6-292 mutation, and an amo1 mutation are obtained or produced and processed to produce a food or beverage product.

In another aspect, the present invention provides a method of producing a food or beverage product, wherein the method comprises: (i) obtaining or producing barley grain as described herein; and (ii) processing the grain to produce the product. The product may conveniently be selected from the group consisting of wholemeal, flour, starch, bran, β-glucan, fructan, a non-starch polysaccharide, and cracked, ground, polished, milled, kibbled, rolled or pearled grain. The processed barley grain may be employed directly, or in another embodiment, the processed grain is mixed with one or more other ingredients to make the food or beverage product. In some embodiment, the methods further comprises (iii) assessing the level or type of starch, starch content, amylose, amylopectin, β-glucan, fructan, non-starch polysaccharides, dietary fibre, or resistant starch in the barley grain or the product therefrom.

In some embodiments, the food or beverage product is a grain, flour, breakfast cereal, biscuit, muffin, muesli bar, noodle, a sweetening agent, a low calorie additive, a bulking agent, a dietary fibre, a texturizing agent, a preservative, a probiotic agent or the like or any combination of these. The food product may be an extruded food product such as extruded breakfast cereals or snacks, or a flaked or rolled product. The food product may be a food ingredient such as a baking ingredient or baking mixes.

In another embodiment, the present invention provides a method of producing a barley plant or capable of producing grain which has a reduced level or activity of SSIIa protein and a starch content of at least 41%, wherein the method comprises: (i) introducing into said plant an agent which down-regulates the level or activity of endogenous starch synthase II (SSII) in the plant relative to a control plant, or a mutation in an endogenous gene encoding SSII in the plant, and (ii) selecting the barley plant which produces the grain. In some embodiments, the methods further comprise introducing into the plant a genetic variation which reduces the activity of an amo1 gene. Agents conveniently comprises a nucleic acid molecule which down-regulates endogenous SSII gene expression, such as a gene-silencing chimeric gene, an antisense, ribozyme, co-suppression, dsRNA molecule, hairpin RNA or other exogenous nucleic acid molecule that down-regulates endogenous SSII expression.

In some embodiments, the methods further comprise assessing the level, activity and/or type of starch, starch content, amylose, amylopectin, β-glucan, fructan, non-starch polysaccharide, dietary fibre or resistant starch in the barley grain or a product therefrom. In some embodiments, the methods comprise analyzing the plant with one or more genetic markers. In some embodiment, the reduced level or activity of SSIIa protein is less than 25%, less than 10%, less than 5%, or essentially lacking relative to that of a control plant or the plant prior to the introduction of the agent or mutation.

In some embodiments, the invention provides a method of producing barley grain as described comprising the steps of growing a barley plant and harvesting the grain. In another embodiment, the present invention provides the herein disclosed plant or grain or wholemeal or flour of when used, or for use, in the production of a product to increase the level of resistant starch, dietary fibre, water soluble carbohydrate, β-glucan, fructan or non-starch carbohydrate in said product or to decrease the glycemic index (GI) of said product.

Fructan, starch or β-glucan isolated from a plant, grain or wholemeal flour of the subject invention is used, for example, in a food as a sweetening agent, a low calorie additive, a bulking agent, a dietary fibre, a texturizing agent, a preservative, a probiotic agent or the like or any combination of these. Thus, in some embodiments, grain, flour, wholemeal, starch, β-glucan or fructan isolated from a plant, grain, wholemeal or flour of the present invention is used in the production of a food product to increase the level of resistant starch, dietary fibre, water soluble carbohydrate, β-glucan, fructan in said food product or to decrease the glycemic index (GI) of said food product. In some embodiments, the levels of amylose, β-glucan and fructan, and preferably resistant starch, are increased. Accordingly, the present invention contemplates a food product comprising a food ingredient at a level of at least 10% on a dry weight basis, wherein the food ingredient is said barley grain as described herein comprising at least 41% starch (w/w) or wholemeal or flour obtained therefrom wherein the wholemeal or flour comprises a reduced level or activity of SSIIa and a starch construct of at least 41% (w/w). In some embodiments, the wholemeal or flour comprises 3-11% fructan (w/w) or 4-11% (w/w) fructan on a weight basis.

In some other embodiments, the wholemeal or flour comprises a β-glucan content of 5-9% (w/w), or greater than 9% (w/w). In other embodiments, the wholemeal or flour comprises 50% or 60% amylose as a proportion of total starch in the wholemeal or flour.

In an illustrative embodiment, the barley comprises the sex6-292 allele.

In another illustrative embodiment, the product is selected from the group consisting of bread, buns, breakfast cereal, cake, biscuit, pastry, crackers, muffins, pizza, croissants, bagels, pretzels, pasta, noodles, baking ingredients, baking mixes, soup, sauce, thickening agent, confectionary, tortillas, granola bars, snacks and other farinaceous goods. The product may be a beverage such as a high energy drink or smoothie.

In another embodiment, the present invention provides for the use of a grain or flour isolated from a plant or grain as described herein in the production of a food product to increase the level of one or two or more of starch, amylose, amylopectin, β-glucan, fructan, non-starch polysaccharide, dietary fibre or resistant starch in the food product.

In another embodiment, the invention provides a method of identifying a variety of barley grain which has increased levels of one or two or more of starch, amylose, amylopectin, β-glucan, fructan, non-starch polysaccharide, dietary fibre or resistant starch. In some embodiments, the method comprises (i) obtaining barley grain which is altered in starch via synthesis or catabolism, and (ii) determining the amount of one or two or more of starch, amylose, amylopectin, β-glucan, fructan, non-starch polysaccharide, dietary fibre or resistant starch in the grain. In further embodiments, the method comprises (iii) comparing the level in (ii) to that in wild-type grain which is not altered in starch via synthesis or catabolism or a grain of a parental or other control plant. In still further embodiments the method comprises selecting the grain if the level/s in (ii) are increased in the altered grain. In some embodiments, the methods comprise mutagenesis or plant cell transformation prior to step (i). In preferred embodiments, the barley grain comprises a mutation in an amo1 gene and a reduced activity of a starch synthase which may be SSIIa, SSIIIa or GBSS, such as a reduced level of GBSSI. Such grain may be obtained by crossing the barley mutant M292 or other barley comprising the sex6-292 allele or the variety Prowashonupana and a barley containing an amo1 mutant locus such as High Amylose Glacier.

In another aspect, the present invention provides a method of determining the amount of starch, amylose, amylopectin, β-glucan, fructan, non-starch polysaccharide, dietary fibre or resistant starch level(s) in cereal grain such as barley grain, comprising the step of obtaining grain comprising at least 41% starch (w/w) according to the present invention, processing the grain so as to extract the starch, amylose, amylopectin, β-glucan, fructan, non-starch polysaccharide, dietary fibre or resistant starch, and measuring the amount of extracted starch, amylose, amylopectin, β-glucan, fructan, non-starch polysaccharide, dietary fibre or resistant starch so as to determine the amount of starch, amylose, amylopectin, β-glucan, fructan, non-starch polysaccharide, dietary fibre or resistant starch in the grain.

In another embodiment, the invention provides a method for preparing a food or beverage, comprising mixing the barley grain or a product obtained therefrom by the presently disclosed methods with another food or beverage ingredient. Thus the method comprises: (i) obtaining or producing barley grain comprising a reduced level or activity of SSIIa protein and a starch content of at least 41% (w/w); and (ii) processing the grain to produce the product. The product may conveniently be selected from the group consisting of wholemeal, flour, starch, bran, β-glucan, fructan, a non-starch polysaccharide, and cracked, ground, polished, milled, kibbled, rolled or pearled grain. The method further comprising mixing the product with another food or beverage product or a precursor thereof.

The invention further provides a method for providing starch, amylose, amylopectin, β-glucan, fructan, non-starch polysaccharide, dietary fibre or resistant starch to improve one or more indicators of health in a mammal, wherein the method comprises administering, to the mammal, a composition comprising barley grain, wholemeal or flour therefrom or a food or beverage obtained therefrom comprising a reduced level or activity of SSIIa protein and a starch content of at least 41% (w/w) or the food product as described herein. In some embodiment, the grain, flour, starch, amylose, amylopectin, β-glucan, fructan, non-starch polysaccharide, dietary fibre or resistant starch is in the form of a food product, a beverage or a pharmaceutical composition. In some embodiments, the grain or flour is in the form of a fructan product. In some embodiment, the one or more indicators of health is an increased number of beneficial intestinal bacteria, reduced number of aberrant crypt foci, increased mineral absorption, reduced level of insulin, reduced glycaemic index, reduced glycaemic load, reduced blood glucose, reduced blood pressure, reduced body weight, reduced blood cholesterol level, increased HDL cholesterol level, increased bone density, increased calcium levels, more frequent bowel movement, or improved blood serum cardiovascular profile.

In a related embodiment, the invention provides a method for ameliorating one or more symptoms of a condition associated with low levels of dietary starch, starch content, amylose, amylopectin, β-glucan, fructan, non-starch polysaccharide, dietary fibre or resistant starch in a subject, said method comprising administering orally to the subject grain as described herein or a processed product comprising one or more of starch, amylose, amylopectin, β-glucan, fructan, non-starch polysaccharide, dietary fibre or resistant starch obtained therefrom for a time and under conditions sufficient to ameliorate one or more symptoms.

In some embodiments of the method the condition is selected from the group consisting of diabetes, obesity, heart disease, hypertension, constipation, osteoporesis and cancer.

Any subject who could benefit from the present methods or compositions is encompassed. The term "subject" includes, without limitation, humans and non-human primates, livestock animals such as cattle, pigs or chickens, or young animals such as calves or piglets, companion animals such as dogs or cats, horses, laboratory test animals, captive wild animals, reptiles and amphibians, fish, and birds. A subject, regardless of whether it is a human or non-human organism may be referred to as a patient, individual, subject, animal, host or recipient. In a particular embodiment the subject is a human.

The above summary is not and should not be seen in any way as an exhaustive recitation of all embodiments of the present invention.

BRIEF DESCRIPTION OF THE TABLES

Table 1 provides RS content and GI level of barley wholemeal

Table 2 provides RS content and GI level of bread produced using 100% barley wholemeal Table 3 provides a statistical analysis of the effects of genotype on RS contents of bread produced with 30% or 100% barley flour Table 4 provides RS content and GI level of breads produced with 30% barley flour Table 5 provides a statistical analysis of the effects of genotype on RS content (mg RS per g starch) of bread produced with 100% barley flour Table 6 provides a statistical analysis of the effects of genotype on RS content (mg RS per g starch) of breads produced with 30% barley flour Table 7 provides a statistical analysis of the effects of genotype on GI level of the 10 g breads produced with 30% or 100% barley flour Table 8 provides a description of the SEQ ID NOs provided herein.

Table 9 provides an amino acid sub-classification.

Table 10 provides exemplary amino acid substitutions.

DETAILED DESCRIPTION

Figure 2:
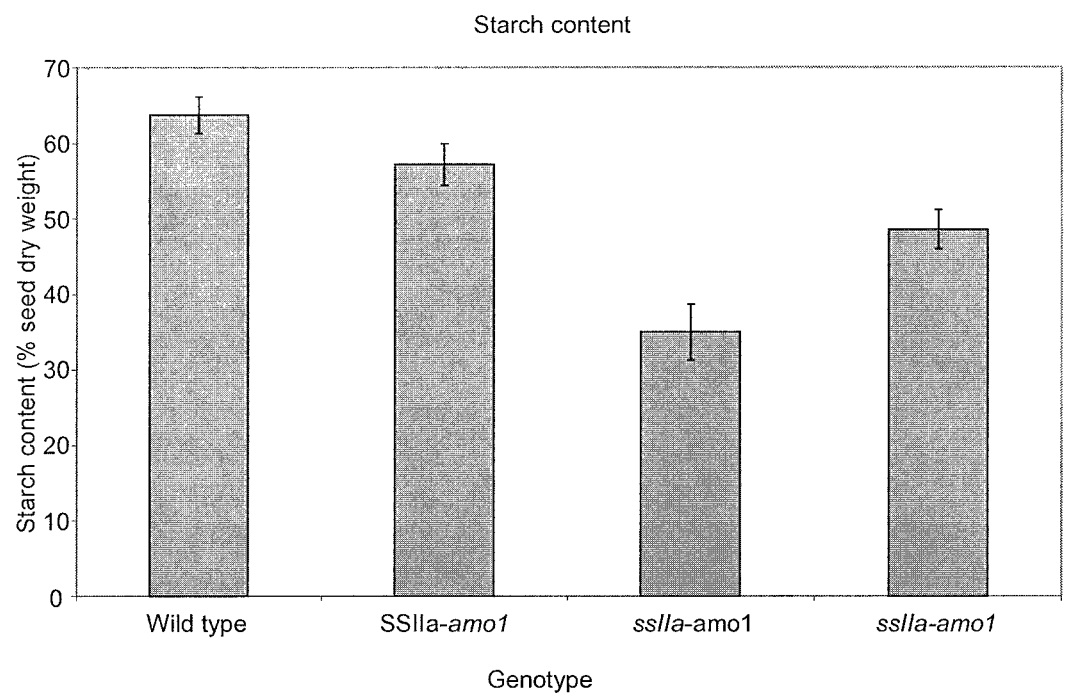
FIG. 2 is a bar graph illustrating starch content as a percentage of seed dry weight for the four genotypes; wild type, SSIIa-amo1, ssIIa-amo1 and ssIIa-amo1.

The present invention is predicated upon the surprising discovery that the agronomic advantages of SSIIa mutant barley, that of inter alia high amylose and fructan could be further enhanced in a variety comprising a loss of function mutation in the SSIIa gene together with a genetic variation which reduces the activity of an amo1 gene. In particular, as shown in FIG. 2, double barley mutants showed enhanced levels of starch over single SSIIa mutants.

Accordingly, in one embodiment the present invention provides barley grain comprising a reduced level or activity of SSIIa protein and a starch content of at least 41% (w/w). In a related embodiment, the grain comprises an amylose content of at least 50% or at least 60% as a proportion of the total starch in the grain. Further, in some embodiments, the grain comprises a R-glucan content of 5-9% (w/w), or greater than 9% (w/w). In another embodiment, the grain comprises a fructan content of 3-11% (w/w), or 4-11%. In another embodiment, the lysine content in the grain is at least 4 g per 100 g protein.

Starch is composed only of glucosidic residues and is found as two types of molecules, amylose and amylopectin, which can be distinguished on the basis of molecular size or other properties. Amylose molecules are essentially linear polymers composed of α-1,4 linked glucosidic units, while amylopectin is a highly branched molecule with α-1,6 glucosidic bonds linking many linear chains of α-1,4 linked glucosidic units. Amylopectin is made of large molecules ranging in size between several tens of thousands to hundreds of thousands of glucose units with around 5 percent α-1,6 branches. Amylose on the other hand is composed of molecules ranging in size between several hundreds to several thousand glucosidic residues with less than one percent branches (for review see Buléon et al., *International Journal of Biological Macromolecules*, 23: 85-112, 1998). Wild-type cereal starches typically contain 20-30% amylose while the remainder is amylopectin.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and ATP. Secondly, the activated glucosyl donor, ADP-glucose, is transferred to the non-reducing end of a pre-existing α1-4 linkage by starch synthases. Thirdly, starch branching enzymes introduce branch points through the cleavage of a region of α-1,4 linked glucan followed by transfer of the cleaved chain to an acceptor chain, forming a new α-1,6 linkage. Starch branching enzymes are the only enzymes that can introduce the α-1,6 linkages into α-polyglucans and therefore play an essential role in the formation of amylopectin. Finally, starch debranching enzymes remove some of the branch linkages although the mechanism through which they act is unresolved.

While it is clear that at least these four activities are required for normal starch granule synthesis in higher plants, multiple isoforms of each of the four activities are found in the endosperm of higher plants and specific roles have been proposed for individual isoforms on the basis of mutational analysis or through the modification of gene expression levels using transgenic approaches. In the cereal endosperm, four classes of starch synthase are found in the cereal endosperm, an isoform exclusively localised within the starch granule, granule-bound starch synthase (GBSS) which is essential for amylose synthesis, two forms that are partitioned between the granule and the soluble fraction (SSI, Li et al., *Plant Physiology*, 120: 1147-1155, 1999a, SSII, Li et al., *Theoretical and Applied Genetics*, 98: 1208-1216, 1999b) and a fourth form that is entirely located in the soluble fraction, SSIII (Cao et al., *Archives of Biochemistry and Biophysics*, 373: 135-146, 2000; Li et al., 1999b (supra); Li et al., 2000 (supra)). Mutations in SSII and SSIII have been shown to alter amylopectin structure (Gao et al., *Plant Cell*, 10: 399-412, 1998; Craig et al., *Plant Cell* 10: 413-426, 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, *Biochemical Genetics*, 20: 483-492, 1982; Boyer and Preiss, *Carbohydrate Research*, 61: 321-334, 1978; Mizuno et al., *Journal of Biochemistry*, 112: 643-651, 1992; Sun et al., *The New Phytologist*, 137: 215-215, 1997). Alignment of SBE sequences has revealed a high degree of sequence similarity at both the nucleotide and amino acid levels and allows the grouping into the SBEI, SBEIIa and SBEIIb classes.

Two types of debranching enzymes are present in higher plants and are defined on the basis of their substrate specificities, isoamylase type debranching enzymes, and pullulanase type debranching enzymes (Myers et al., *Plant Physiology*, 122: 989-997, 2000). Sugary-1 mutations in maize and rice are associated with deficiency of both debranching enzymes (James et al., *Plant Cell*, 7: 417-429, 1995; Kubo et al., *Plant Physiology*, 121: 399-409, 1999) however the causal mutation maps to the same location as the isoamylase-type debranching enzyme gene.

A mutant form of barley, designated M292 or M342, has been shown to have an elevated amylose starch phenotype and a reduced amylopectin starch phenotype. This phenotype has suspected benefits for human health (Morell et al., *Plant J.* 34: 173-185, 2003b; Topping et al., *Starch/Stärke* 55: 539-545, 2003; Bird et al., *J. Nutr.* 134: 831-835, 2004a; Bird et al. *Br. J. Nutr.* 92: 607-615, 2004b). It is caused by a mutation in the starch synthase IIa gene (SSIIa) located on chromosome 7H of barley, as described in International patent application PCT/AU01/01452 (Publication No. WO 02/37955) the disclosure of which is incorporated herein by reference.

The barley sex6 mutation resulted from the presence of a stop codon within the starch synthase IIa (SSIIa) gene. The stop codon lead to premature termination of translation of the transcript. The SSIIa protein was not detectable in the endosperm of this mutant (Morell et al. 2003 (supra)). The loss of SSIIa activity lead to an 80% decrease in amylopectin synthesis, and the remaining amylopectin polymers in general have altered chain length distribution, and consequently an altered amylose: amylopectin ratio so that the starch of the grain contained about 70% amylose.

In some embodiments, the present invention provides for improvements in barley plant utility by increasing the yield of starch and non-starch components in grain. The modification may be limited to grain or alternatively, the modification may be throughout the plant in various of its tissues and parts. As used herein, "modifying" or "modified" means a change in the plant or grain, which may be an increase or decrease in amount, activity, rate of production, rate of inactivation, rate of breakdown, delay of onset, earlier onset, addition or removal of material, mutation, or any combination of these, so long as there is a reduced level or activity of starch synthase II. The terms include either an increase or decrease in the functional level of a gene or protein of interest. "Functional level" should be understood to refer to the level of active protein. The functional level is a combination of the actual level of protein present in the host cell and the specific activity of the protein. Accordingly, the functional level may e.g. be modified by increasing or decreasing the actual protein concentration in the host cell, which may readily be achieved by altering expression of a gene encoding the protein. The functional level may also be modified by modulating the specific activity of the protein. Such increase or decrease of the specific activity may be achieved by expressing a variant protein with higher or lower specific activity or by replacing the endogenous gene encoding the relevant protein with an allele encoding such a variant. Increase or decrease of the specific activity may also be achieved by modifying expression of an effector molecule. In certain embodiments, the expression level of an appropriate coding sequence or activity or amount of an enzyme is chosen such that it is at least about 10%, at least 20%, at least 30%, at least 40%, at least 50%, at least 60%, at least 80% or even at least about 100%, at least 200%, at least 500%, or at least 1000% higher, or at least about 10%, at least 20%, at least 30%, at least 40%, at least 50%, at least 60%, at least 70%, at least 80%, at least 90%, at least 92%, at least 94%, at least 96%, at least 97%, at least 98% or at least 99% lower than a reference expression level, or reduced to an undetectable level.

Another way of distinguishing the required reduction in SSII level or activity is by quantifying the increased level or the increase in various forms of fructan in a modified plant or grain therefrom.

As used herein, the terms "modifying", "altering", "increasing", "increased", "reducing", "reduced", "inhibited", "mutant" or the like are considered relative terms, i.e. in comparison with the wild-type or unaltered or control state. In some embodiments, a wild-type plant is an appropriate "control plant" however in many situations the control plant must be determined by the skilled addressee using their ordinary skill in the art.

The "level of a protein" refers to the amount of a particular protein, for example SSII, which may be measured by any means known in the art such as, for example, Western blot analysis or other immunological means.

The "level of an enzyme activity" refers to the amount of a particular enzyme measured in an enzyme assay.

The "activity of SSIIa protein" refers to the amount of a particular enzyme measured in an enzyme assay.

It would be appreciated that the level of activity of an enzyme might be altered in a mutant if a more or less active protein is produced, but not the expression level (amount) of the protein itself. Conversely, the amount of protein might be altered but the activity (per unit protein) remain the same. Reductions in both amount and activity are also possible such as, for example, when the expression of a gene encoding the enzyme is reduced transcriptionally or post-transcriptionally. In certain embodiments, the reduction in the level of protein or activity of SSII is by at least 40% or by at least 60% compared to the level of protein or activity in the grain of unmodified barley, or by at least 75%, at least 90% or at least 95%. The reduction in the level of the protein or enzyme activity or gene expression may occur at any stage in the development of the leaf, seed or grain, particularly during the daytime when photosynthesis is occurring, or during the grain filling stage while starch is being synthesized in the developing endosperm, or at all stages of grain development through to maturity. The term "wild-type" as used herein has its normal meaning in the field of genetics and includes barley, cultivars or genotypes which are not modified as taught herein. Some preferred "wild-type" barley varieties are described herein, such as, for example, the cultivar Himalaya The modified phenotype may be achieved by partial or full inhibition of the expression of an SSIIa gene. Techniques well known in the art such as SDS-PAGE and immunoblotting are carried out on hydrolysed and unhydrolysed grains and fractions thereof to identify the plants or grain where modifications have occurred to starch forming enzymes These methods include analysis of plants by methods described herein or further by methods such as such as microarray analysis, electrophoresis, chromatography (including paper chromatography, thin layer chromatography, gas chromatography, gas-liquid chromatography and high-performance liquid chromatography) techniques. Separated components are typically identified by comparison of separation profiles with standards of known identity, or by analytical techniques such as mass spectrometry and nuclear magnetic resonance spectroscopy. For example, reference may be made to Example 9, Robinson, *The Organic Constituents of Higher Plants*, Cordus Press, North Amherst, USA, 1980; Adams et al., *Anal. Biochem.*, 266: 77-84, 1999; Veronese et al., *Enz. Microbial Tech.*, 24: 263-269, 1999; Hendrix et al., *J. Insect Physiol.*, 47: 423-432, 2001; Thompson et al., *Carbohydrate Res.*, 331: 149-161, 2001; and references cited therein. Carbohydrates can be assayed using standard protocols known to persons skilled in the art.

Alteration in SSIIa level or activity may be achieved by the introduction of one or more genetic variations into the barley plant. That is, the genetic variations lead, directly or indirectly, to the alteration in enzyme activity or level in the plant part during growth or development and consequently to the enzyme, starch and fructan modifications described herein. The genetic variation may be a heterologous polynucleotide which is introduced into the plant or a progenitor cell, for example by transformation or mutagenesis. The genetic variation may subsequently be introduced into different genetic backgrounds by crossing, as known in the art of plant breeding. In some embodiments, the level or functional activity of SSIIa is down regulated to a level less than about 80%, less than 70%, less than 60%, less than 50%, less than 40%, less than 30%, less than 20% or less than 15%, and suitably less than about 10%, less than 9%, less than 8%, less than 7%, less than 6%, less than 5%, less than 4%, less than 3%, less than 2% or less than 1% relative to a corresponding control plant to achieve elevated levels of starch or non-starch components, preferably in the proportion of amylose in the starch content of the grain. In a preferred embodiment, elevated levels are at least twice that of controls. Preferably, in this embodiment, this reduction results in a substantial enhancement of non-starch polysaccharide such as fructan levels which is generally at least about 50% or 55% and more especially at least about 60%, at least 65%, at least 70%, at least 75%, at least 80%, at least 85%, at least 90%, at least 95% or greater increase in fructan level relative to a corresponding control plant grown under the same environmental conditions. The amount of reduced SSIIa level or activity required may depend upon other factors such as the plant species or strain environmental factors. However, it is considered that any optimisation, which may be required in such an event is achievable using routine methods including those described herein.

Reduced SSIIa levels may be accomplished in tissues throughout the plant, for example using a constitutive promoter to drive expression of a heterologous polynucleotide that down regulates SSIIa. Preferably, it may be accomplished in sink tissues, more preferably in developing endosperm, using a tissue-specific or developmentally regulated promoter. "Sink cell" and "sink tissue" as used herein, refer to cells, tissues or organs which comprise a net inflow of organic carbon that has entered the cells in a form other than fixation of carbon dioxide i.e. as sugars or other carbohydrates. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

Genes

In some embodiments, the present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The "starch synthase II gene" "SSII" or the like as used herein refers to a nucleotide sequence encoding starch synthase II (SSII) in barley, which can readily be distinguished from other starch synthases or other proteins by those skilled in the art. In a preferred embodiment, a barley SSII gene refers to a nucleic acid molecule, which may be present in or isolated from barley or derived therefrom, comprising nucleotides having a sequence having at least 80% identity to the cDNA sequence shown in SEQ ID NO: 1. In a preferred embodiment, the SSII gene is an SSIIa gene, or the SSII protein is an SSIIa protein, each of which may be applied to any or all of the aspects of the invention disclosed herein. The nucleotide sequence of cDNA of the SSIIa gene from M292 is set out in SEQ ID NO: 9.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Polynucleotides

The present invention including the description, tables and sequence listing, refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention refers to use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Polynucleotides used as a probe are typically conjugated with a detectable label such as a radioisotope, hapten, an enzyme, biotin, a fluorescent molecule or a chemiluminescent molecule. Oligonucleotides of the invention are useful in methods of detecting an allele of an SSII or other gene linked to a trait of interest, for example modified starch or fructan levels. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridising, for example, to the cereal genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without negatively influencing the ability of the oligonucleotide to hybridise to the target region. In addition, variants may readily be designed which hybridise close to, for example to within 50 nucleotides, the region of the plant genome where the specific oligonucleotides defined herein hybridise. Probes, oligonucleotides and the like are based upon the herein described sequences or corrected versions thereof or variants thereof or functional homologs from other cereal plants.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

By "corresponds to" or "corresponding to" is meant a polynucleotide (a) having a nucleotide sequence that is substantially identical or complementary to all or most of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, lie, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, *J. Mol. Biol.* 48: 443-453, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, at least 500 or at least 600 nucleotides in each case. Reference also may be made to the BLAST family of programs as for example disclosed by Altschul et al., *Nucleic Acids Res.* 25: 3389, 1997. A detailed discussion of sequence analysis can be found in Unit 19.3 of Ausubel et al., *"Current Protocols in Molecular Biology"*, John Wiley & Sons Inc, 1994-1998, Chapter 15.

Nucleotide or amino acid sequences are indicated as "essentially similar" when such sequences have a sequence identity of at least 80%, particularly at least 85%, quite particularly at least 90%, especially at least 95%, more especially are identical. It is clear that when RNA sequences are described as essentially similar to, correspond to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO., such as SEQ ID NO: 1 or 3 to 6.

Preferably, a polynucleotide of the invention which encodes a polypeptide with SSII activity is greater than 800, preferably greater than 900, and even more preferably greater than 1,000 or 2000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization and washing. The higher the stringency, the higher will be the degree of complementarity between a target nucleotide sequence and the labelled polynucleotide sequence (probe). "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Ausubel et al., (eds.), Current Protocols in Molecular Biology, John Wiley & Sons, NY, 6.3.1-6.3.6., 1989. Aqueous and non-aqueous methods are described in that reference and either can be used. Specific hybridization conditions referred to herein are as follows: 1) low stringency hybridization conditions are for hybridization in 6× sodium chloride/sodium citrate (SSC) at 45° C., followed by two washes in 0.2×SSC, 0.1% SDS at 50-55° C.; 2) medium stringency hybridization conditions are for hybridization in 6×SSC at about 45° C., followed by one or more washes in 0.2×SSC, 0.1% SDS at 60° C.; 3) high stringency hybridization conditions are for hybridization in 6×SSC at 45° C., followed by one or more washes in 0.2×SSC, 0.1% SDS at 65° C.; and 4) very high stringency hybridization conditions are for hybridization in 0.5 M sodium phosphate buffer, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogs and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

Illustrative polypeptides having SSII activity are set out in the sequence listing and described in Table 8. Accordingly, the present invention proposes without limitation the modification of SSII polypeptides having the amino acid sequences set forth in SEQ ID NO: 2 and naturally occurring variants, corrected versions thereof and variants as described herein such as variants having about 80% sequence identity.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO. 2.

The % identity of a polypeptide relative to another polypeptide can be determined by GAP (Needleman and Wunsch, 1970 (supra)) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment of a polypeptide is a portion of a polypeptide of the invention, less than full length, which maintains a defined activity of the full-length polypeptide. In a particularly preferred embodiment, the biologically active fragment is able to synthesize starch to produce amylose chains having a DP of at least 15. Biologically active fragments can be any size as long as they maintain the defined activity, but are preferably at least 200 or at least 250 amino acid residues long.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama, Trends Biotechnol. 16: 76-82, 1998. These DNA shuffling techniques may include genes related to those of the present invention, such as SSII genes from plant species other than wheat or barley, and/or include different genes from the same plant encoding similar proteins, such as the wheat or barley starch synthase I or III genes. Products derived from mutated/altered DNA can readily be screened using techniques described herein to determine if they possess, for example, starch synthase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 10 under the heading of "exemplary substitutions".

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In one embodiment, a promoter is expressed in all photosynthetic tissue, which may correspond to all aerial parts of the plant, for example a promoter that is involved in expressing a gene required for photosynthesis such as rubisco small subunit promoters. The term may also refer to expression at specific developmental stages in an organ, such as in early or late embryogenesis or different stages of maturity; or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the endosperm, cytosol, vacuole, or apoplastic space may be achieved by the inclusion in the structure of the gene product of appropriate signals for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter for high molecular weight (HMW) glutenin gene, Bx17 which is expressed preferentially in the developing endosperm of cereal plants. Further endosperm specific promoters include the high molecular weight glutenin promoter, the wheat SSI promoter, and the wheat BEII promoter. Other endosperm-specific promoters may readily be obtained from genes which encode starch biosynthetic enzymes or storage proteins in the developing grain.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters; promoters from plants, such as ubiquitin promoters such as the Ubi promoter from the maize ubi-1 gene, Christensen et al., (1996) (see, e.g., U.S. Pat. No. 4,962,028) or actin promoters; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.*, 1: 499-511, 1983; Salomon et al., *EMBO J.*, 3: 141-146, 1984; Garfinkel et al., *Cell*, 27: 143-153, 1983; Barker et al., *Plant Mol. Biol.*, 2: 235-350, 1983; including various promoters isolated from plants and viruses such as the cauliflower mosaic virus promoter (CaMV 35S, 19S). Many tissue specific promoter regions are known. Other transcriptional initiation regions which preferentially provide for transcription in certain tissues or under certain growth conditions, include those from genes encoding napin, seed ACP, zein, or other seed storage proteins. Fruit specific promoters are also known, one such promoter is the E8 promoter, described by Deikman et al., *EMBO J.*, 2: 3315-3320, 1998 and DellaPenna et al., *Plant Cell*, 1: 53-63, 1989. Non-limiting methods for assessing promoter activity are disclosed by Medberry et al., *Plant Cell*, 4: 185-192, 1992; Medberry et al., *Plant J.* 3: 619-626, 1993, Sambrook et al., *Molecular Cloning: A Laboratory Manual* (2nd ed.). Cold Spring Harbour Laboratory, Cold Spring Harbour, N Y, 1989, and McPherson et al. (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. Other cis-acting sequences which may be employed include transcriptional and/or translational enhancers. Enhancer regions are well known to persons skilled in the art, and can include an ATG translational initiation codon and adjacent sequences. The initiation codon must be in phase with the reading frame of the coding sequence relating to the foreign or exogenous polynucleotide to ensure translation of the entire sequence. The translation control signals and initiation codons can be of a variety of origins, both natural and synthetic. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention typically comprises a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from the nopaline synthase (nos) gene of *Agrobacterium tumefaciens* (Bevan et al., *Nucl. Acid Res.*, 11: 369, 1983) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the small subunit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An, *Methods in Enzymology*, 153: 292, 1987, which is incorporated herein by reference.

As the DNA sequence inserted between the transcription initiation site and the start of the coding sequence, i.e., the untranslated 5' leader sequence (5'UTR), can influence gene expression, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi, *Nucl. Acid Res.* 15: 6643, 1987.

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide.

Vectors

The present invention includes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (npt) gene conferring resistance to kanamycin, paromomycin, G418 and the like as, for example, described by Potrykus et al., *Mol. Gen. Genet.* 199: 183, 1985; a glutathione-S-transferase gene from rat liver conferring resistance to glutathione derived herbicides as, for example, described in EP-A 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP-A 275957, a gene encoding a 5-enolshikimate-3-phosphate synthase (EPSPS) conferring tolerance to N-phosphonomethylglycine as, for example, described by Hinchee et al., *Biotech.* 6: 915, 1988, a bar gene conferring resistance against bialaphos as, for example, described in WO 91/02071; a nitrilase gene such as bxn from *Klebsiella ozaenae* which confers resistance to bromoxynil (Stalker et al., *Science,* 242: 419, 1988); a dihydrofolate reductase (DHFR) gene conferring resistance to methotrexate (Thillet et al., *J. Biol. Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., *Biochem. Biophys. Res. Comm.* 126: 1259-68, 1985), which may be employed in calcium-sensitive bioluminescence detection; a green fluorescent protein gene (Niedz et al., *Plant Cell Reports,* 14: 403, 1995); a luciferase (luc) gene (Ow et al., *Science,* 234: 856, 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

The level of a protein, for example, an enzyme involved in starch synthesis in developing endosperm of a barley plant, may be modulated by increasing the level of expression of a nucleotide sequence that codes for the protein in a plant cell, or decreasing the level of expression of a gene encoding the protein in the plant, leading to altered fructan accumulation in grain. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial increase in fructan levels. This may be detected by simple testing of grain from the transformants. Alternatively, a population of mutagenized grain or a population of plants from a breeding program may be screened for individual lines with altered fructan accumulation.

Reducing gene expression may be achieved through introduction and transcription of a "gene-silencing chimeric gene" introduced into the plant cell. The gene-silencing chimeric gene may be introduced stably into the plant cell's genome, preferably nuclear genome, or it may be introduced transiently, for example on a viral vector. As used herein "gene-silencing effect" refers to the reduction of expression of a target nucleic acid in a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing includes an abolishing of the expression of the target nucleic acid or gene and a partial effect in either extent or duration. It is sufficient that the level of expression of the target nucleic acid in the presence of the silencing RNA is lower that in the absence thereof. The level of expression may be reduced by at least about 40%, or at least about 50%, or at least about 60%, or at least about 70%, or at least about 80%, or at least about 90%, or at least about 95%, or at least about 99%. The target nucleic acid may be a gene involved in starch synthesis or metabolism, for example starch degradation, but may also include any other endogenous genes, transgenes or exogenous genes such as viral genes which may not be present in the plant cell at the time of introduction of the transgene.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, *Manual of Antisense Methodology*, Kluwer, 1999). The use of antisense techniques in plants has been reviewed by Bourque, *Plant Sci.* 105: 125-149, 1995 and Senior, *Biotech. Genet. Engin. Revs.* 15: 79-119, 1998. Bourque, 1995 (supra) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 (supra) states that antisense methods are now a very well established technique for manipulating gene expression.

As used herein, the term "an antisense polynucleotide which hybridises under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the coding region of the targeted gene, or the 5'-untranslated region (UTR) or the 3'-UTR or combination of these. It may be complementary in part to intron sequences, which may be spliced out during or after transcription, but is preferably complementary only to exon sequences of the target gene. In view of the generally greater divergence of the UTRs, targeting these regions provides greater specificity of gene inhibition.

The length of the antisense sequence should be at least 19 contiguous nucleotides, preferably at least 25 or 30 or 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Accordingly, also provided by this invention is a nucleic acid molecule such as a chimeric DNA coding for an antisense RNA of the invention, including cells, tissues, organs, plants, grain and the like comprising the nucleic acid molecule.

Ribozymes

The term "ribozyme" as used herein refers to an RNA molecule which specifically recognizes a distinct substrate RNA and catalyzes its cleavage. Typically, the ribozyme contains a region of nucleotides which are complementary to a region of the target RNA, enabling the ribozyme to specifically hybridize to the target RNA under physiological conditions, for example in the cell in which the ribozyme acts, and an enzymatic region referred to herein as the "catalytic domain". The types of ribozymes that are particularly useful in this invention are the hammerhead ribozyme (Haseloff and Gerlach, *Nature* 334: 585-591, 1988; Perriman et al., *Gene,* 113: 157-163, 1992) and the hairpin ribozyme (Shippy et al., *Mol. Biotech.* 12: 117-129, 1999). DNA encoding the ribozymes can be synthesized using methods well known in the art and may be incorporated into a genetic construct or expression vector for expression in the cell of interest. Accordingly, also provided by this invention is a nucleic acid molecule such as a chimeric DNA coding for a ribozyme of the invention, including cells, tissues, organs, plants, grain and the like comprising the nucleic acid molecule. Typically, the DNA encoding the ribozyme is inserted into an expression cassette under control of a promoter and a transcription termination signal that function in the cell. Specific ribozyme cleavage sites within any potential RNA target may be identified by scanning the target molecule for ribozyme cleavage sites which include the trinucleotide sequences GUA, GUU and GUC. Once identified, short RNA sequences of between about 5 and 20 ribonucleotides corresponding to the region of the target gene 5' and 3' of the cleavage site may be evaluated for predicted structural features such as secondary structure that may render the oligonucleotide sequence less suitable. When employed, ribozymes may be selected from the group consisting of hammerhead ribozymes, hairpin ribozymes, axehead ribozymes, newt satellite ribozymes, Tetrahymena ribozymes and RNAse P ribozymes, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should be capable of hybridizing to a target nucleic acid molecule (for example an mRNA encoding a polypeptide provided as SEQ ID NO:2) under "physiological conditions", namely those conditions within a cell, especially conditions in a plant cell such as a wheat or barley cell.

RNA Interference/Duplex RNA

As used herein, "artificially introduced dsRNA molecule" refers to the introduction of dsRNA molecule, which may e.g. occur endogenously by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al., *Proc. Natl. Acad. Sci. U.S.A.* 95: 13959-13964, 1998 have provided a model for the mechanism by which dsRNA can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with an intervening sequence or spacer region forming a loop structure, so the hairpin RNA comprises a stem-loop structure. The design and production of suitable dsRNA molecules for the present invention is well within the capacity of a person skilled in the art, particularly considering Waterhouse et al., 1998 (supra), Smith et al., *Nature,* 407: 319-320, 2000, WO 99/53050, WO 99/49029, and WO 01/34815. Accordingly, also provided by this invention is a nucleic acid molecule such as a chimeric DNA coding for a duplex RNA such as a hairpin RNA of the invention, including cells, tissues, organs, plants, grain and the like comprising the nucleic acid molecule.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing (Smith et al., 2000 (supra)). The double-stranded region may comprise one or two RNA molecules, transcribed from either one DNA region or two. The dsRNA may be classified as long hpRNA, having long, sense and antisense regions which can be largely complementary, but need not be entirely complementary (typically forming a basepaired region larger than about 100 bp, preferably ranging between 200-1000 bp). hpRNA can also be smaller with the double-stranded portion ranging in size from about 30 to about 50 bp, or from 30 to about 100 bp (see WO 04/073390, herein incorporated by reference). The presence of the double stranded RNA region is thought to trigger a response from an endogenous plant system that processes the double stranded RNA to oligonucleotides of 21-24 nucleotides long, and also uses these oligonucleotides for sequence-specific cleavage of the homologous RNA transcript from the target plant gene, efficiently reducing or eliminating the activity of the target gene.

The length of the sense and antisense sequences that hybridise should each be at least 19 contiguous nucleotides, preferably at least 27 or 30 or 50 nucleotides, and more preferably at least 100, 200, or 500 nucleotides, up to the full-length sequence corresponding to the entire gene transcript. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The RNA molecule may be a hybrid between different sequences targeting different target RNAs, allowing reduction in expression of more than one target gene, or it may be one sequence which corresponds to a family of related target genes such as a multigene family. The sequences used in the dsRNA preferably correspond to exon sequences of the target gene and may correspond to 5' and/or 3' untranslated sequences or protein coding sequences or any combination thereof.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Other silencing RNA may be "unpolyadenylated RNA" comprising at least 20 consecutive nucleotides having at least 95% sequence identity to the complement of a nucleotide sequence of an RNA transcript of the target gene, such as described in WO 01/12824 or U.S. Pat. No. 6,423,885 (both documents herein incorporated by reference). Yet another type of silencing RNA is an RNA molecule as described in WO 03/076619 (herein incorporated by reference) comprising at least 20 consecutive nucleotides having at least 95% sequence identity to the sequence of the target nucleic acid or the complement thereof, and further comprising a largely-double stranded region as described in WO 03/076619.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic partial inverted repeat. When transcribed, microRNA genes give rise to partially basepaired stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, *Funct Integr Genomics,* 5: 129-135, 2005; Pasquinelli et al., *Curr Opin Genet Develop* 15: 200-205, 2005; Almeida and Allshire, *Trends Cell Biol.* 15: 251-258, 2005, herein incorporated by reference).

Cosuppression

Another molecular biological approach that may be used for specifically reducing gene expression is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the integration, or stable maintenance in a replicable non-integrated form, of an introduced foreign or exogenous gene or sequence. By "transgene" is meant a foreign or exogenous gene or sequence that is introduced into the genome of a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, from an embryo, scutellum, protoplast, callus, or other tissue, but not including growth of a plant from a seed.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch, *Ann Rev Plant Physiol Plant Mol Biol.* 48: 297-326, 1997.

Introduction and expression of foreign or exogenous polynucleotides may be performed using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond, *Biotechnology,* 1: 262, 1983 and Hoekema et al., *Nature,* 303: 179, 1983. Such a binary system is preferred inter alia because it does not require integration into the Ti plasmid in *Agrobacterium.*

Methods involving the use of *Agrobacterium* include, but are not limited to: (a) co-cultivation of *Agrobacterium* with cultured isolated protoplasts; (b) transformation of plant cells or tissues with *Agrobacterium*; (c) transformation of seeds, apices or meristems with *Agrobacterium*, or (d) inoculation in planta such as the floral-dip method as described by Bechtold et al., *C. R. Acad. Sci. Paris,* 316: 1194, 1993 or in wheat (as described in WO 00/63398, herein incorporated by reference). This approach is based on the infiltration of a suspension of *Agrobacterium* cells.

Alternatively, the chimeric construct may be introduced using root-inducing (Ri) plasmids of *Agrobacterium* as vectors.

Methods for transformation of cereal plants such as wheat and barley for introducing genetic variation into the plant by introduction of an exogenous nucleic acid and for regeneration of plants from protoplasts or immature plant embryos are well known in the art, see for example, Wan and Lemaux, *Plant Physiol.* 104: 37-48, 1994, Tingay et al., *Plant J.* 11: 1369-1376, 1997, Canadian Patent Application No. 2,092,588, Australian Patent Application No 61781/94, Australian Patent No 667939, U.S. Pat. No. 6,100,447, International Patent Application PCT/US97/10621, U.S. Pat. Nos. 5,589,617, 6,541,257. Preferably, transgenic plants are produced by *Agrobacterium tumefaciens* mediated transformation procedures. Vectors carrying the desired nucleic acid construct may be introduced into regenerable cereal cells of tissue cultured plants or explants. The regenerable cells are preferably from the scutellum of immature embryos, mature embryos, callus derived from these, or the meristematic tissue. Immature embryos are preferably those from inflorescences about 10-15 days after anthesis.

The genetic construct can also be introduced into plant cells by electroporation as, for example, described by Fromm et al., *Proc. Natl. Acad. Sci. U.S.A.* 82: 5824, 1985 and Shimamoto et al., *Nature,* 338: 274-276, 1989. In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus.

Another method for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al., *Nature,* 327: 70, 1987.

Alternatively, the nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

Mutagenesis

The plants of the invention can be produced and identified after mutagenesis. This may provide a plant which is non-transgenic, which is desirable in some markets.

Mutants can be either naturally occurring (that is to say, isolated from a natural source) or synthetic (for example, by performing mutagenesis on the nucleic acid) or induced. Generally, a progenitor plant cell, tissue, seed or plant may be subjected to mutagenesis to produce single or multiple mutations, such as nucleotide substitutions, deletions, additions and/or codon modification. In the context of this application, an "induced mutation" is an artificially induced genetic variation which may be the result of chemical, radiation or biologically-based mutagenesis, for example transposon or T-DNA insertion. Preferred mutations are null mutations such as nonsense mutations, frameshift mutations, insertional mutations or splice-site variants which completely inactivate the gene. Nucleotide insertional derivatives include 5' and 3' terminal fusions as well as intra-sequence insertions of single or multiple nucleotides. Insertional nucleotide sequence variants are those in which one or more nucleotides are introduced into the nucleotide sequence, which may be obtained by random insertion with suitable screening of the resulting products. Deletional variants are characterised by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or only one nucleotide. Such a substitution may be "silent" in that the substitution does not change the amino acid defined by the codon. Alternatively, conservative substituents are designed to alter one amino acid for another similar acting amino acid. Typical conservative substitutions are those made in accordance with Table 10 "Exemplary substitutions".

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

In a preferred embodiment, the plant comprises a deletion of at least part of a SSII gene or a frameshift or splice site variation in such gene.

In another preferred embodiment, the plant comprises a mutation in an amo1 gene, such as the AC38 allele known in the art.

Mutagenesis can be achieved by chemical or radiation means, for example EMS or sodium azide (Zwar and Chandler, *Planta* 197: 39-48, 1995) treatment of seed, or gamma irradiation, well know in the art.

Chemical mutagenesis tends to favour nucleotide substitutions rather than deletions. Heavy ion beam (HIB) irradiation is known as an effective technique for mutation breeding to produce new plant cultivars, see for example Hayashi et al., *Effects of ion beam irradiation on mutation induction in rice. Cyclotrons and Their Applications* 2007, Eighteenth International Conference 237-239, 2007 and Kazama et al., *Plant Biotechnology* 25: 113-117, 2008. Ion beam irradiation has two physical factors, the dose (gy) and LET (linear energy transfer, keV/um) for biological effects that determine the amount of DNA damage and the size of DNA deletion, and these can be adjusted according to the desired extent of mutagenesis. HIB generates a collection of mutants, many of them comprising deletions, that may be screened for mutations in specific SSIIa or Amo1 genes. Mutants which are identified may be backcrossed with non-mutated wheat plants as recurrent parents in order to remove and therefore reduce the effect of unlinked mutations in the mutagenised genome.

Biological agents useful in producing site-specific mutants include enzymes that include double stranded breaks in DNA that stimulate endogenous repair mechanisms. These include endonucleases, zinc finger nucleases, transposases and site-specific recombinases. Zinc finger nucleases (ZFNs), for example, facilitate site-specific cleavage within a genome allowing endogenous or other end-joining repair mechanisms to introduce deletions or insertions to repair the gap. Zinc finger nuclease technology is reviewed in Le Provost et al., *Trends in Biotechnology* 28(3): 134-141, 2009, See also Durai et al., *Nucleic Acids Research*

33(18): 5978-5990, 2005 and Liu et al., *Biotechnology and Bioengineering,* 106: 97-105, 2010.

Isolation of mutants may be achieved by screening mutagenised plants or seed. For example, a mutagenized population of barley plants may be screened for low SSIIa activity in the leaf or grain starch, mutation of the SSIIa or amo1 gene by a PCR or heteroduplex based assay, or loss of the SSII protein by ELISA. In a polyploid plant, screening is preferably done in a genotype that already lacks one or two of the SSII activities, for example in a wheat plant already mutant in the SSII genes on two of the three genomes, so that a mutant entirely lacking the functional activity is sought. Alternatively, the mutation may be identified using techniques such as "tilling" in a population mutagenised with an agent such as EMS (Slade and Knauf, *Transgenic Res.* 14: 109-115, 2005). Such mutations may then be introduced into desirable genetic backgrounds by crossing the mutant with a plant of the desired genetic background and performing a suitable number of backcrosses to cross out the originally undesired parent background.

The mutation may have been introduced into the plant directly by mutagenesis or indirectly by crossing of two parental plants, one of which comprised the introduced mutation. The modified plants such as cereal plants may be transgenic or non-transgenic. Using mutagenesis, a non-transgenic plant lacking the function of interest may be produced. The invention also extends to the grain or other plant parts produced from the plants and any propagating material of the plants that can be used to produce the plants with the desired characteristics, such as cultured tissue or cells. The invention clearly extends to methods of producing or identifying such plants or the grain produced by such plants.

Plants of the invention can be produced using the process known as TILLING (Targeting Induced Local Lesions IN Genomes). In a first step, introduced mutations such as novel single base pair changes are induced in a population of plants by treating cells, seeds, pollen or other plant parts with a chemical mutagen or radiation, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel1, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf, 2005 (supra), and Henikoff et al., *Plant Physiol.* 135: 630-636, 2004, herein incorporated by reference.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., *Plant J.* 37: 778-786, 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Genetic Linkage

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cereal plant such as wheat or barley. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like.

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene.

By extracting DNA from, for example, young shoots and testing with a specific marker for the introgressed desirable trait, early selection of plants for further backcrossing is made whilst energy and resources are concentrated on fewer plants.

Any molecular biological technique known in the art which is capable of detecting alleles of an SSII or other gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, *Current Genomics*, 1: 301-311, 2000; Langridge et al., *Aust J Agric Res* 52: 1043-1077, 2001). The invention also includes the use of molecular marker techniques to detect polymorphisms linked to alleles of (for example) an SSII gene which confers altered fructan accumulation. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., 2001 (supra).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (McPherson and Moller (Ed), BIOS Scientific Publishers Ltd, Oxford, 2000). PCR can be performed on cDNA obtained from reverse transcribing mRNA isolated from plant cells expressing an SSII gene or on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Plants

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, pollen, tumor tissue, such as crown galls, and various forms of aggregations of plant cells in culture, such as calli. Exemplary plant tissues in or from seeds are endosperm, scutellum, aleurone layer and embryo. The invention accordingly includes plants and plant parts and products comprising these, particularly grain comprising fructan.

As used herein, the term "grain" refers to mature seed of a plant, such as is typically harvested commercially in the field. Thus, the term includes harvested seed and seed on a plant that is ready for harvesting. Mature cereal grain such as wheat or barley commonly has a moisture content of less than about 18-20%.

A "transgenic plant" as used herein refers to a plant that contains a gene construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of altered fructan content of the grain of the plant, or related phenotype such as altered starch synthase activity.

As used herein, "germination" refers to the emergence of the root tip from the seed coat after imbibition. "Germination rate" refers to the percentage of seeds in a population which have germinated over a period of time, for example 7 or 10 days, after imbibition. A population of seeds can be assessed daily over several days to determine the germination percentage over time. With regard to seeds of the present invention, as used herein the term "germination rate which is substantially the same" means that the germination rate of the transgenic seeds is at least 90%, that of isogenic wild-type seeds.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Food Production

In another aspect, the invention provides barley plants and grain, and products obtained therefrom, that is useful for food or feed production, the grain having increased levels of starch compared to corresponding SSIIa mutant grains, and increased levels of non-starch components compared to corresponding wild-type grains. Preferably the plant from which the grain is obtained has a reduced level of SSIIa activity in the endosperm during development. The plant of the present invention is useful for food production and in particular for commercial food production. Such food production might include the making of flour, dough or other products that might be an ingredient in commercial food production. In an embodiment which is desirable for use in food production, the seed or grain of the plant has a fructan content that is increased relative to the wild-type plant. The grain may have a level of activity of degradative enzymes, particularly of one or more amylases such as α-amylase or β-amylase, which is reduced by the presence of a transgene or an introduced mutation which reduces expression of a gene encoding such a degradative enzyme in the grain. Flour or dough from such grain has desirable properties for baking or other food production.

The desired genetic background of the plant will include considerations of agronomic yield and other characteristics. Such characteristics might include whether it is desired to have a winter or spring types, agronomic performance, disease resistance and abiotic stress resistance. Other varieties will be suited for other growing regions. It is preferred that the plant variety of the invention provide a yield not less than 80% of the corresponding wild-type variety in at least some growing regions, more preferably not less than 85% and even more preferably not less than 90%. The yield can readily be measured in controlled field trials.

In further embodiments, the starch content of the grain is at least about 42%, at least about 43%, at least about 45%, at least about 47%, at least about 50%, or at least about 55% (w/w), up to 65%, and more preferably not decreased relative to the wild-type. Wild-type barley grain grown commercially usually has a starch content in the range 55-65%, depending somewhat on the cultivar grown. Alternatively, the seed or grain of the invention has a starch content of at least 90% relative to that of grain from a wild-type plant, and preferably at least 95%. Other desirable characteristics include the capacity to mill the grain, in particular the grain hardness. Another aspect that might make a plant of higher value is the degree of fructan or starch extraction from the grain, the higher extraction rates being more useful, or the protein content, the ration of amylose to amylopectin, or the content of other non-starch polysaccharides such as β-glucan which also contribute to the dietary fibre content of the grain products. Grain shape is also another feature that can impact on the commercial usefulness of a plant, thus grain shape can have an impact on the ease or otherwise with which the grain can be milled.

Starch is readily isolated from grain of the invention using standard methods, for example the method of Schulman and Kammiovirta, *Starch*, 43: 387-389, 1991. On an industrial scale, wet or dry milling can be used. Starch granule size is important in the starch processing industry where there is separation of the larger A granules from the smaller B granules.

Food Products

The invention also encompasses foods, beverages or pharmaceutical preparations produced with products, preferably those comprising increased resistant starch, dietary fibre, amylose, β-glucan, fructan, or other components obtained from the plants or grain of the invention. Such food production might include the making of processed grain, wholemeal, flour, dough or other products that might be an ingredient in commercial food production. The grain of the invention or products derived therefrom containing resistant starch, dietary fibre, amylose, β-glucan or fructan may be used in a variety of food applications for human consumption. As used herein, "humans" refers to *Homo sapiens*. The grain can be used readily in food processing procedures and therefore the invention includes milled, ground, kibbled, pearled or rolled grain or products obtained from the processed or whole grain of the plants of the invention, including flour. These products may be then used in various food products, for example farinaceous products such as breakfast cereals, breads, cakes, biscuits and the like or food additives such as thickeners or binding agents or to make drinks, noodles, pasta or quick soups. The grain or products derived from the grain of the invention are particularly desired in breakfast cereals or as extruded products. The starch or other components may be incorporated into fat or oil products such as margarine or shortening, salad dressing, egg products such as mayonnaise, dairy products such as ice cream, yogurt or cheese, cereal products such as wheat flour, fruit juices, other foods or food materials, or the starch or other components may be processed into beverages or foods such as bread, cake, biscuits, breakfast cereals, pasta, noodles or sauces. Fructan is also useful as a low calorie sweetening product.

In bread, the ingredients comprising fructan which may be in the form of flour or wholemeal may substitute for 10% (w/w) or more of unaltered flour or wholemeal, preferably substituting at least 30% and even more preferably at least 50% of the unaltered flour or wholemeal. The formulation might therefore be, for example, flour 70 parts, high-fructan starch 30 parts, fat 2 parts, salt 2 parts, improver 1 part, yeast 2.5 parts. The production of the bread may be by a rapid dough technique or other techniques as is known by those skilled in the art.

Alternatively, the product of the invention may be incorporated into a farinaceous based pasta product. The amount of fructan of the invention employed in the pasta composition may be in the range of 5-20% (w/w) based on the total weight of farinaceous material more particularly in the range of 10 to 20%. Suitable other farinaceous materials will readily be chosen by a person skilled in the art. Other material may also be added to the composition for example dry or liquid eggs (yolks, whites, or both) or high protein substances such as milk protein or fish protein. Vitamins, minerals, calcium salts, amino acids, buffering agents such as disodium hydrogen phosphate, seasoning, gum, gluten or glyceryl monostearate may also be added.

Other parts of the plants of the invention that are edible may be used as foods for human consumption or as feed for animal use. For example, leaves, stems, or extracts or parts of these comprising cells of the invention from any of these may be used for human or animal consumption. Increased resistant starch, dietary fibre, amylose, β-glucan or fructan content of the plants of the invention and parts thereof may provide advantages for use of these materials as animal feed such as, for example, as feed for pigs, cattle, horses, poultry such as chickens and other animals.

Methods

The products or compounds of the present invention can be formulated in pharmaceutic compositions which are prepared according to conventional pharmaceutical compounding techniques. See, for example, Remington's Pharmaceutical Sciences, 18$^{th}$ Ed., Mack Publishing, Company, Easton, Pa., U.S.A. 1990). The composition may contain the active agent or pharmaceutically acceptable derivative active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

The active agent is preferably administered in a therapeutically effective amount. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, (supra).

The food or beverage or pharmaceutical preparation may be packaged ready for sale or in bulk form. The invention also provides methods of preparing the food, beverage or pharmaceutical preparation of the invention, and recipes or instructions for preparing such foods or beverages. The methods may comprise the steps of harvesting the plant or plant part, separating grain from other plant parts, crushing, extracting, milling, cooking, canning, packaging or other processing steps known in the art. The methods or recipes or instructions may include the steps of processing the plant product of the invention and/or admixing it with other food ingredients, such as heating or baking the mixture or the product to, for example, at least 100° C. The method may include the step of packaging the product so that it is ready for sale.

Industrial Use

The plant products, preferably grain, may be used in production of industrial products such as, for example, ethanol.

The present invention is further described by the following non-limiting Examples.

Example 1: Illustrative Methods and Materials

Plant Material

Barley (*Hordeum vulgare*) lines used were from a back crossed population starting with a cross between parental varieties Himalaya292 (M292 (SEQ ID NOs: 9 to 11), Morell et al. 2003b (supra)) which contained the SSIIa mutation designated herein as the sex6-292 allele, and the variety High Amylose Glacier (HAG, also named AC38). Suitable parental varieties are available in the art. The HAG variety, for example (High Amylose Glacier, also named AC38) is available from CSIRO or from the Australian Winter Cereals Collection, Tamworth, NSW. Crossing of barley plants was carried out in the greenhouse by standard methods. The back cross populations were generated through 3 back crosses from Himalaya292 (male) to HAG (female), and then 3 generations of single seed descent (SSD). The seeds from the $3^{rd}$ back cross were named as BC3F1 and from the $3^{rd}$ SSD were named as BC3F4. To increase the quantity of seeds for each line, 2 or 3 further generations were grown. These were designated as the BC3F6 or BC3F7 generations and used for this study.

Seventy BC3F6 barley lines were grown at CSIRO Plant Industry, Canberra in pots under otherwise natural conditions in 2005. To confirm the selected seed compositions and parameters, a subset of the BC3F7 barley lines which were selected by seed weight, amylose content, and the presence of SSIIa and amo1 mutations were grown either at CSIRO Plant Industry, Canberra in a glasshouse, with natural light and at the temperatures 18° C. (night) and 24° C. (day), or in the field at Yanco, New South Wales, Australia in 2007.

Barley spikes were labelled as at anthesis 2 days after the awns first appeared through the top of the flag leaf containing the enclosed spike. Developing seeds were harvested at 20 days post anthesis (DPA) and after removal of the embryo the developing endosperm was extruded through the cut surface and stored at −80° C.

Other varieties as described herein were obtained commercially or from the Australian Winter Cereals Collection, Tamworth, NSW, Australia.

Genotyping of the BC3F6 Population by PCR Amplification

Young wheat leaves from the BC3F6 generation of the back crossed population were collected and freeze-dried (freezer FTS systems, Stone Ridge, N.Y.). Genomic DNA was isolated with a fast DNA$^R$ kit according to the suppliers instructions (Q-BIOgene).

For genotyping of the SSIIa mutation, primers SSIIaF (5'-CCTGGAACACTTCAGACTGTACG-3' (SEQ ID NO: 3)) starting at nucleotide 1616 and SSIIaR (5'-AGCAT-CACCAGCTGCACGTCCT-3' (SEQ ID NO: 4)) starting at nucleotide 2044 of the SSIIIa cDNA (GenBank no: AY133249) were used for the PCR amplification of a 451 bp product spanning the SSIIa mutation site at nucleotide 1829 of Himalaya292, as described by Morell et al. 2003b (supra) (see also SEQ ID NO: 9). The microsatellite PCR marker EBmac0501 was used for the detection of the amo1 mutation as it located at 68.0 cM on chromosome 1H and was closely linked to the amo1 locus also at 68.0 cM. Primers HHac0501F (5' CACGACGTTGTAAAACGACACT-TAAGTGCCATGCAAAG 3' (SEQ ID NO: 5) and HHac0501R (5' AGGGACAAAAATGGCTAAG 3' (SEQ ID NO: 6)) (GrainGenes Database) were used for the amplification of a PCR fragment from the amo1 locus.

For each PCR reaction of 20 µl, 50 ng genomic DNA, 1.5 mM MgCl$_2$, 0.125 mM each dNTP, 10 pmol primers, 0.5 M glycine betaine, 1 µl DMSO and 1.5 U of Hotstar Taq polymerase (QIAGEN) were used. The PCR reactions were conducted using a HYBAID PCR Express machine (Intergrated Sciences) with 1 cycle of 95° C. for 5 minutes, 35 cycles of 94° C. for 45 seconds, 58° C. for 30 seconds, and 72° C. for 1 minute, 1 cycle of 72° C. for 10 minutes and 1 cycle of 25° C. for 1 minute. The PCR products for the detection of the SSIIa mutation were digested with the restriction enzyme NlaIV at 37° C. overnight. Both digested (for SSIIa mutation) and non-digested (for amo1 mutation) PCR fragments were separated on 2% agarose gels and visualized with gel documentary (UVitec) after GelRed (Biotium) staining.

For genotyping of barley lines from the back crossed barley population between Himalaya292×HAG, primers SSIIaF and SSIIaR were used as described above for the detection of the SSIIa mutation from parental line Himalaya292, and the microsatellite marker EBmac0501 was used for the detection of the amo1 locus from parental line HAG. For the SSIIa mutation, three types of PCR fragment patterns were evident after digestion of the PCR product with NlaIV followed by gel electrophoresis, that differentiated the mutated and wildtype SSIIa alleles. A single DNA fragment of 347 bp indicated the presence of the mutated SSIIa gene, a single 236 bp DNA fragment indicated the presence of the wildtype SSIIa gene, and the presence of both the 347 bp and 236 bp fragments indicated the heterozygous genotype lines. For the amo1 mutation from HAG, the EBmac0501 microsatellite marker also gave three PCR fragmentation patterns. A 167 bp fragment was detected from the amo1 mutant, a 141 bp fragment was detected from wildtype lines, and both 167 bp and 141 bp fragments were detected in the heterozygous lines.

Grain Characteristics

Grain was harvested from plants at maturity. Unless otherwise indicated, average seed weight was determined by weighing 100 seeds with 3 replicates. The seed weight for selected lines was also determined as average seed weight of 500 seeds for 3 replicates for BC3F7 field grown materials at Yanco, NSW. Seed moisture content of grain was measured by standard nuclear magnetic resonance (NMR) methods using an Oxford 4000 NMR Magnet (Oxford analytical instruments Limited). Grain texture was measured using the Single-Kernel Characterization system 4100 (Perten Instruments Inc. Springfield, Ill. 62707 USA) using the RACI Cereal Chemistry Official testing method 12-01. Seed plumpness was grouped as three categories: shrunken, semi-plumped and plumped.

Microscopic Examination of Barley Seed Cross Sections and Scanning Electronic Microscopy Transverse sections approximately 1 mm thick of the middle part of the barley seeds were produced by cutting sections with razor blades, and photographed. They were also coated with gold particles and examined with a JSM-6400 Scanning Electron Microscope (SEM) operating at 15 KV.

Milling of Grain

Grain was ground to wholemeal that would pass through a 0.5 mm sieve, using a cyclonic mill (Cyclotec 1093, Tecator, Sweden). The wholemeal was then used for the analysis below.

β-glucan and Pentosan Analysis

β-glucan content was assayed as described in Megazyme Method (AACC32.23), using 20 mg of wholemeal for each of three replicate samples. Pentosan content was measured using the method from Bell (1985) using 20 mg of wholemeal for each of three replicate samples.

Starch Extraction

Starch was isolated from wholemeal by a protease extraction method (Morrison et al., *J Cereal Sci*, 2: 257-271, 1984) followed by water washing and removal of the tailings. Starch was then washed with acetone and air dried at room temperature (Konik-Rose et al., 2007 (supra)).

Total Starch Analysis

Total starch content of grain was assayed as described in Megazyme Method (AACC76.13) using 20 mg of wholemeal for each of three replicate samples.

Analysis of Starch Composition and Characteristics

Amylose and amylopectin contents in the starch of the grain, or the ratio of amylose to amylopectin, was determined by Sepharose CL-2B gel filtration as follows (Gel filtration method). Approximately 10 mg of total starch was dissolved in 3.0 ml of IM NaOH and fractionated on the basis of molecular weight by chromatography on a Sepharose CL-2B column (Regina et al., *Proc Natl Acad Sci USA*, 103: 3546-3551, 2006). The amount of starch in each of the fractions from the column were measured using the Starch Assay Kit (Sigma) according to the suppliers instructions. The total amount of amylopectin (first peak, higher molecular weight) and amylose (second peak, lower molecular weight) was calculated and the ratio or contents determined.

Alternatively, amylose content was measured using a small scale (2 mg starch) iodine adsorption method (Morrison and Laignelet, *J Cereal Sci*, 1: 9-20, 1983) with some modifications as described by Konik-Rose et al., 2007 (supra).

Chain Length Distribution

Amylopectin chain length distribution was measured, after debranching of the starch samples, by the method of O'Shea et al., *Carbohydr Res*, 307: 1-12, 1998 using a P/ACE 5510 capillary electrophoresis system (Beckman Coulter, NSW Australia) with argon laser-induced fluorescence (LIF) detection. Molar difference plots were generated by subtracting the normalized chain length distribution for modified starch from the normalized distribution for starch from an isogenic non modified control.

The gelatinisation temperature profiles of starch samples may be measured using a Pyris 1 differential scanning calorimeter (Perkin Elmer, Norwalk Conn., USA). The viscosity of starch solutions may be measured on a Rapid-Visco-Analyser (RVA, Newport Scientific Pty Ltd, Warriewood, Sydney), using conditions as reported by Batey et al., *Starch* 48: 338-344, 1997. The parameters that may be measured include peak viscosity (the maximum hot paste viscosity), holding strength, final viscosity and pasting temperature. Pasting properties may be measured using the Rapid Visco Analyser as follows. Starch (3.0 g) is added to distilled water (25.0 ml) in the DSC pan and the RVA run profile is: 2 mins at 50° C., heat for 6 mins to 95° C., hold at 95° C. for 4 mins, cool for 4 mins to 50° C., hold at 50° C. for 4 mins. The measured parameters are: Peak viscosity at 95° C., Holding strength at end of 95° C. holding period, Breakdown=Peak Viscosity−Holding strength, Final viscosity at end of 50° C. holding period, Setback=Final Viscosity−Holding strength. The software Thermocline for Windows version 2.2 (Newport Scientific Pty Ltd, NSW Australia) may be used for collection and analysis of data.

The swelling volume of flour or starch may be determined according to the method of Konik-Rose et al., *Starch-Stärke*, 53: 14-20, 2001. The uptake of water is measured by weighing the sample prior to and after mixing the flour or starch sample in water at defined temperatures (for example, 90° C.) and following collection of the gelatinized material.

Starch Granule Morphology, Birefringence and Granule Size Distribution

Granule morphology was examined by SEM (JSM-6400) and light microscopy with polarized light. The shapes and birefringence of the starch granules were examined as described (Yamamori et al., 2000 (supra)). Granule size distribution (by volume) of the starch slurries was determined using a laser diffraction particle size analyser (Mastersizer 2000, Malvern Instruments, Malvern, England). The percentage of small B-type starch granules was determined using a cut-off diameter of 7 μm.

Lipid Analysis

Total lipid content may be assayed by NMR using an Oxford 4000 NMR Magnet, Oxford Analytical Instruments Limited, UK. For each sample, 1 g of seeds is dried at 38.8° C. for 64 hours. The dried seeds are then measured using NMR and compared against a pure barley oil controls extracted from cv. Himalaya or M292 grain.

Protein Content, Lipid Content, Moisture Content and Ash Content

Protein content was determined by measurement of nitrogen content using Mass Spectrometer Method using a Europa 20-20 isotope ratio mass spectrometer with an automated nitrogen and carbon analyzer preparation system. Three to 8 mg of wholemeal of barley was used. A nitrogen to protein conversion factor of 6.25 was used for the calculation of the protein content in barley seeds (Mosse 1990). Lipid content, moisture content and ash content were measured using the AOAC 983.23 method, AACC Method 44-19 and AACC Method 08-01.

Total Dietary Fibre Assay

The gravimetric method of Prosky et al. (1985; AOAC 985.29) was used to determine total dietary fibre (TDF) of the wholemeal. Duplicate samples were assayed.

Non Starch Polysaccharide Assay

Total neutral non-starch polysaccharides (NSP) were measured by a modification of the gas chromatographic procedure of Theander et al., *J AOAC Int* 78: 1030-1044, 1995. The modification involved a 2-hour hydrolysis with 1 M sulphuric acid followed by centrifugation to remove insoluble NSP and a further hydrolysis of the supernatant using 2 M trifluoroacetic acid for soluble NSP.

Resistant Starch Assay

An in vitro procedure was used to determine resistant starch (RS) content. The method has two sections: firstly, starch in each sample was hydrolysed under simulated physiological conditions; secondly, by-products were removed through washing and the residual starch determined after homogenization and drying of the sample. Starch quantitated at the end of the digestion treatment represented the resistant starch content of the sample. Typically, triplicate samples of whole meal along with appropriate standards were mixed with artificial saliva and the resultant bolus incubated with pancreatic and gastric enzymes at physiological pH and temperature. The amount of residual starch in the digesta was determined using conventional enzymatic techniques and spectrophotometry and the resistant starch content of the sample expressed as a percentage of sample weight or total starch content.

On day 1, an amount of sample representing up to 500 mg of carbohydrate was weighed into a 125 mL Erlenmeyer flask. A carbonate buffer was prepared by dissolving 121 mg of $NaHCO_3$ and 157 mg of KCl in approximately 90 mL purified water, adding 159 μL of 1 M $CaCl_2.6H_2O$ solution and 41 μL of 0.49 M $MgCl_2.6H_2O$, adjusting the pH to 7 to 7.1 with 0.32 M HCl, and adjusting the volume to 100 mL. This buffer was stored at 4° C. for up to five days. An artificial saliva solution containing 250 units of α-amylase (Sigma A-3176 Type VI-B from porcine pancreas) per mL of the carbonate buffer was prepared. An amount of the artificial saliva solution, approximately equal to the weight of food, was added to the flask. About 15-20 sec after adding the saliva, 5 mL of pepsin solution in HCl (1 mg/mL pepsin (Sigma) in 0.02 M HCl, pH 2.0, made up on day of use) was added to each flask. The mixing of the amylase and then pepsin mimicked a human chewing the sample before swallowing it. The mixture was incubated at 37° C. for 30 min with shaking at 85 rpm. The mixture was then neutralised with 5 mL of 0.02M NaOH. 25 mL of acetate buffer (0.2 M, pH 6) and 5 mL of pancreatin enzyme mixture containing 2 mg/mL pancreatin (Sigma, porcine pancreas at 4×USP activity) and 28U of amyloglucosidase (AMG, Sigma) from *Aspergillus niger* in acetate buffer, pH6, were added per flask. Each flask was capped with aluminium foil and incubated at 37° C. for 16 hours in a reciprocating water bath set to 85 rpm.

On day 2, the contents of each flask was transferred quantitatively to a 50 mL polypropylene tube and centrifuged at 2000×g for 10 min at room temperature. The supernatants were discarded and each pellet washed three times with 20 mL of water, gently vortexing the tube with each wash to break up the pellet, followed by centrifugation. 50 uL of the last water wash was tested with Glucose Trinder reagent for the absence of free glucose. Each pellet was then resuspended in approximately 6 mL of purified water and homogenised three times for 10 seconds using an Ultra Turrax TP18/10 with an S25N-8G dispersing tool. The contents were quantitatively transferred to a 25 mL volumetric flask and made to volume. The contents were mixed thoroughly and returned to the polypropylene tube. A 5 mL sample of each suspension was transferred to a 25 mL culture tube and immediately shell frozen in liquid nitrogen and freeze dried.

On day 3, total starch in each sample was measured using reagents supplied in the Megazyme Total Starch Procedure kit. Starch standards (Regular Maize Starch, Sigma S-5296) and an assay reagent blank were prepared. Samples, controls and reagent blanks were wet with 0.4 mL of 80% ethanol to aid dispersion, followed by vortexing. Immediately, 2 mL of DMSO was added and solutions mixed by vortexing. The tubes were placed in a boiling water bath for 5 min, and 3 mL of thermostable α-amylase (100 U/ml) in MOPS buffer (pH 7, containing 5 mM $CaCl_2$ and 0.02% sodium azide added immediately. Solutions were incubated in the boiling water bath for a further 12 min, with vortex mixing at 3 min intervals. Tubes were then placed in a 50° C. water bath and 4 mL of sodium acetate buffer (200 mM, pH 4.5, containing 0.02% sodium azide) and 0.1 mL of amyloglucosidase at 300 U/ml added. The mixtures were incubated at 50° C. for 30 min with gentle mixing at 10 min intervals. The volumes were made up to 25 mL in a volumetric flask and mixed well. Aliquots were centrifuged at 2000×g for 10 min. The amount of glucose in 50 µL of supernatant was determined with 1.0 mL of Glucose Trinder reagent and measuring the absorbance at 505 nm after incubation of the tubes at room temperature in the dark for a minimum of 18 min and a maximum of 45 min.

Quantification of Water-Soluble Carbohydrate Contents

Total water soluble carbohydrates (WSC) were extracted from wholemeal following the method of Lunn and Hatch, *Planta* 197: 385-391, 1995 with the following modifications. Wholemeal is defined herein as the product obtained by milling mature grain, without subsequent fractionation (e.g. sieving) to remove the bran. Therefore wholemeal contains all of the components in the grain.

Barley wholemeal (100 mg) was extracted three times with 10 ml of 80% ethanol (v/v) in a boiling water bath for 10 minutes. The supernatants from each extraction were pooled, freeze dried and re-suspended in 2 ml milliQ water. The quantities of sucrose, glucose, and fructose were measured using a colorimetric microtiter plate enzymatic assay as described (Campbell et al., *J Sci Food Agric* 79: 232-236, 1999; Ruuska et al., *Funct Plant Biol* 33: 799-809, 2006). Sugars, maltose and fructo-oligosaccharides (fructans) were also analysed by high performance anion exchange chromatography (HPAEC) as described in Ruuska et al., 2006 (supra). Both methods resulted in comparable values.

To determine maltose levels, total sugars extracted from barley whole meal were assayed essentially as described by Bernfeld, Amylases alpha and beta. In: Colowick and Kaplan (eds), Methods in enzymology, Academic, NY, p. 149, 1955, using maltose standard solutions for comparison, as follows. Total sugars were diluted 10 to 100-fold. Maltose standards (10 tubes) were prepared as 0.3 to 5 micromoles per ml. One ml of each dilution of maltose (in total sugars or maltose dilutions) was mixed with 1 ml of dinitrosalicylic acid colour reagent. The sugar solution was then incubated at 100° C. for 5 minutes and cooled to room temperature. Ten ml reagent grade water was added to each tube and mixed well. The samples were measured at $A_{540}$ with a spectrophotometer. Maltose was also determined by HPAEC as described above.

Enzyme Assays

Total starch synthase activity in samples such as developing endosperm of cereals may be measured by extraction of proteins and assay by the methods described in Libessart et al. *Plant Cell.* 7(8): 1117-1127, 1995 or Cao et al., *Plant Physiol.* 120(1): 205-16, 1999. The assays use $^{14}C$ labeled ADPG substrate and measure incorporation of the monomer into starch polymers. Individual isoforms of starch synthase in extracts may be separated by gel electrophoresis and assayed in-gel (zymogram) as follows. Extracts from samples such as developing seeds may be prepared using 50 mM potassium phosphate buffer, pH7.5, 5 mM EDTA, 20% glycerol, 10M Pefabloc and 0.05 mM dithiothreitol (DTT). After grinding the seeds to a pulp in the buffer or homogenizing the sample, the mixture is centrifuged at 14,000 g for 15 min at 4° C. and the supernatant drawn off. The protein concentration in the supernatant may be measured using Coomassie Protein Reagent or other standard means. Extracts may be stored at −80° C. if the protein extracts are to be run on native gels. For denaturing gel electrophoresis, 100 µl of extract is mixed with SDS and β-mercaptoethanol and the mixtures are incubated in boiling water for 4 min to denature the proteins. Electrophoresis is carried out in standard denaturing polyacrylamide gels using 8% polyacrylamide separating gels overlaid with 4.5% polyacrylamide stacking gels. After electrophoresis, the proteins may be renatured by soaking the gels in 40 mM Tris-HCl buffers for a minimum of 2 hr, changing the buffer every 30 min and using at least 100 mL of buffer for each buffer change. For non-denaturing gels, the denaturing step with SDS and β-mercaptoethanol is omitted and SDS omitted from the gels. A starch synthase assay buffer including Tris-glycine (25 mM Tris, 0.19M glycine), 0.133M ammonium sulphate, 10 mM $MgCl_2$, 670 µg/mL BSA and 1 mM ADPG substrate may be used to detect starch synthase bands, followed by staining with 2% KI, 0.2% $I_2$ iodine solution to detect the starch product.

Alternatively, starch synthase or other starch biosynthetic enzymes may be detected in samples using specific antibodies (ELISA).

Statistical Analyses of the Relationship Between Genotypes and Seed Components or Starch Properties Statistical analyses were performed using Genstat version 9. Analysis of variance was performed for seed weight, total starch content, amylase content, beta-glucan content, sugar content, starch granule size and amylopectin chain length distribution to obtain the least significant difference (LSD, P<0.05), looking at variation between the genotypes.

Example 2: Genotyping Plants

A population of lines segregating for the presence or absence of mutations at the SSIIa and amo1 loci was generated by performing three backcrosses from a sex6-292 donor line (Himalaya292) into an amo1-AC38 recurrent parent. Three generations of single seed descent were performed from the BC3F2 lines in order to generate sufficient fixed genotypes to investigate the relative impact of the sex6 and amo1 loci, alone and in combination, on starch synthesis and grain composition. A marker for the causal mutation in the SSIIa gene was used to genotype the sex6 locus in BC3F6 lines (Morell et al. 2003b (supra)), while the tightly linked microsatellite marker EBmac0501 was used as a surrogate marker of amo1-38 status as described in Example 1.

Among the 70 BC3F6 lines genotyped, 14 lines were homozygous for both sex6-292 and amo1-AC38 alleles (sex6-292/amo1-AC38) and were therefore considered as SSIIa-amo1 double mutants, 17 lines were homozygous for the sex6-292 and wild type amo1-alleles (sex6-292/amo1-wt) and therefore designated as SSIIa single mutants, 10 lines were homozygous for wild type sex6 and mutant amo1-AC38 alleles (sex6-wt/amo1-AC38) and were therefore designated as amo1 single mutants, while 15 lines were wild type for both sex6 and amo1 (sex6-wt/amo1-wt) and designated as wild type. The remaining lines were heterozygous for either the sex6 mutation (7 lines) or for the EBmac0501 marker.

The DNA marker for the SSIIa gene which was polymorphic between the HAG and Himalaya292 parental lines (Example 3) was also used to genotype the 56 homozygous lines. This analysis showed the presence of the SSIIa gene from HAG in 26 lines, and the SSIIIa gene from Himalaya292 in 30 lines. Among the 56 lines genotyped with the EBmac0501 and SSIIIa gene markers, 5 lines showed recombinant genotypes. When the genotypes and phenotypes including the plumpness of seeds and the starch contents were correlated, 4 lines genotyped with EBmac0501 and 1 line genotyped with the SSIIIa gene marker gave recombinant phenotypes. This indicated that there was some recombination between the markers and the amo1 locus providing the starch phenotypes, and also indicated that the amo1 gene and SSIIIa genes were genetically distinct even if closely linked in barley.

The parental varieties were also different in the hulled or hulless phenotypes-HAG is a hulled variety of barley while Himalaya292 was hulless. The SSIIa-amo1 double mutants were segregating for this characteristic, and therefore they could be classed in two subgroups—hulled or hulless. Therefore, the four genotypes of barley lines distinguished as described above were categorized into five groups, namely: wildtype lines, SSIIa single mutants, amo1 single mutants, hulless double mutants and hulled double mutants. Four lines were used from each of the five groups for the analysis of starch granule distribution, WSC, CE and seed morphology. One line from each genotype was used for endosperm structure and starch granule morphology. Eleven wildtype lines, 9 lines of amo1 mutants, 13 lines of SSIIa mutants, 4 lines of hulless double mutants and 6 lines of hulled double mutants were used for the analysis of grain composition, amylose content and seed weight as follows.

Seed Weight

Average seed weight (average of 100 seed weight) was measured for homozygous lines from the BC3F6 population. Average seed weight was 52.7±5.0 mg for 11 wildtype lines, 52.8±2.8 mg for 9 amo1 lines, 38.7±2.5 mg for 13 SSIIa mutant lines, and 47.6±4.5 mg for the 6 hulled double mutant lines and 44.7±1.0 mg for the 4 hulless double mutant lines. There were no statistically significant differences between seed weights of the amo1 mutant lines and the wildtype lines ($P<0.05$), showing that the amo1 mutation did not affect seed weight. However, there were statistically significant differences ($P<0.05$) between each of the SSIIa single mutants and double mutant (hulled and hulless) and each of the three respective other genotypes. Similar observations on the seed weights of the 4 genotypes were also obtained for BC3F7 populations in separate glasshouse and field trials of the lines in 2007. The surprising and unexpected result was that the reduced seed weight caused by the presence of the SSIIa mutation, known to be due to the reduced amylopectin synthesis in the absence of SSIIa activity, was partly offset by the combination with the amo1 mutation.

Seed Morphology

Intact seeds from four representative lines for each genotype were examined by stereoscopic microscope on both dorsal and crease sides. The SSIIa single mutant lines produced shrunken seeds while the wildtype and amo1 single mutant lines produced plump well filled seeds. The double mutant seeds, both hulled and hulless, were observed to have an intermediate phenotype, plumper than SSIIa mutant seeds, yet not as well filled as amo1 and wildtype seeds. These observations were consistent with the seed-weights.

Figure 1:
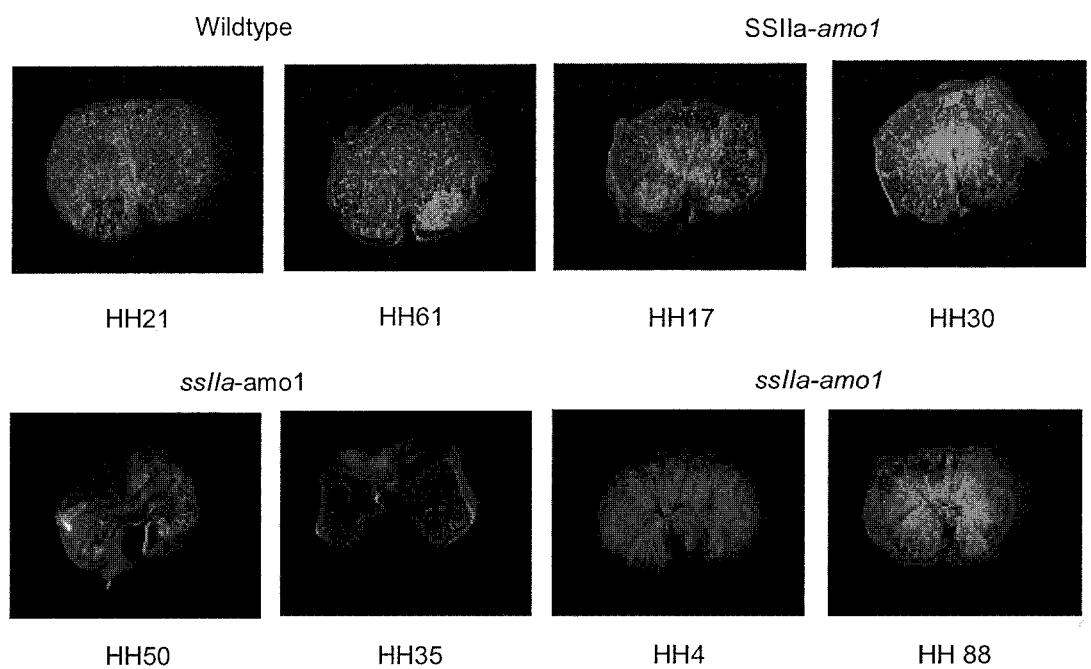
FIG. 1 is a photographic representation of seeds showing seed morphology. Lines used were wildtype lines (HH21 and HH61), amo1 mutants (HH17 and HH30), SSIIa mutants (HH35 and HH 50), SSIIa-amo1 double mutants (HH4 and HH88) derived from the BC3F6 population between Himalaya292 and HAG. Two parental lines and two control lines were also used.

To further illustrate the nature of plumpness of the seeds from these genotypes, transverse sections of the middle part of seeds across the largest diameter were examined (FIG. 1). Transverse sections from wildtype and amo1 mutant lines showed fully filled endosperms while SSIIa mutant lines showed incompletely filled (shrunken) seeds with a considerable reduction in endosperm packing density. The SSIIa-amo1 double mutant lines showed an intermediate phenotype with an endosperm that was more filled than the SSIIa mutant endosperm and yet less filled than wildtype or amo1 mutant lines.

For higher magnification examination, transverse sections of the barley seeds from all genotypes were examined by scanning electronic microscopy (SEM). On the surface of the sections at the dorsal side, the wildtype barley grains showed square shaped aleuronic cells of approximately 20-25 µm×20-25 µm size, with differentiated sub-aleuronic cell layers, and the endosperm was filled with flat-round cells with clear cell boundaries of approximate size 210 µm×130 µm. For the sex6-wt/amo1-AC38 mutant, the aleurone cells were rectangular in shape with dimensions of approximately 20-25 µm×10-15 µm. Sub-aleuronic cells were clearly differentiated and the endosperm contained flat cells with clear cell boundaries which were longer and narrower than those from the wildtype line, with approximate size 230 µm×30 µm. The sex6-292/amo1-wt mutant displayed irregular rectangular shaped aleurone cells of 45-50 µm×5-10 µm size, the sub-aleurone cells were not clearly differentiated, and the endosperm contained irregular cells of 90-95 µm×25-30 µm size. For the sex6-292/amo1-AC38 double mutant genotype, the aleuronic cells were nearly square-shaped and approximately 20 µm×20 µm size, the sub-aleuronic cells were so poorly differentiated they could not be identified, and the endosperm contained flat-round cells with clear boundaries of approximately 110 µm×90 µm.

Total Starch Content.

Total starch content was measured as described in Example 1 on BC3F6 seed for the four genotypes. Starch content averaged 64.3±2.4% for wildtype lines, 57.2±2.8% for amo1 mutant lines, 34.9±4.0% for SSIIa mutant lines, 50.8±2.8% for hulless double mutant lines and 47.6±2.3% for hulled double mutant lines (FIG. 2). Compared to the wildtype lines, amo1 mutants, hulless double mutants, hulled double mutants and SSIIa mutant lines contained 7.1%, 13.5%, 16.7% and 29.4% respectively less total starch. These values were statistically different among the five groups (P<0.05) except that the values for the hulless and hulled groups were not significantly different. Consistent relationships between the seed weights of the five groups were also obtained (P<0.05) for BC3F7 grain from separate glasshouse and field trials in 2007. These data showed that the increased seed weights observed for the SSIIa-amo1 double mutant seeds compared to the SSIIa single mutant seeds were due to increased starch content.

Amylose Content

Amylose content was measured for all lines from the four genotypes. Amylose content ranged from 32.0±3.2% for wildtype lines, 49.5±2.7% for amo1 mutants, 57.6±10.0% for SSIIa mutant lines, 62.2±4.1% for hulless double mutants and 59.8±2.3% for hulled double mutants. Statistical analysis showed that the SSIIa mutant lines and double mutant lines contained significantly higher amylose contents in the seed than those from amo1 mutants and wildtype lines, however the amylose contents of SSIIa mutant and double mutants were not significantly different (P<0.05), showing that the SSIIa mutation was increasing the proportion of amylose in the total starch of the grain but addition of the amo1 mutation did not further significantly increase the proportion of amylose. These differences in amylose content between genotypes were consistent in BC3F7 lines grown in 2007.

Starch Chain Length Distribution

To examine the effects of genotypes on starch chain length distribution, starch was isolated from four lines from each group of the BC3F6 cross population and analysed by Fluorophore Assisted Carbohydrate Electrophoresis (FACE). The percentage of chains were pooled into bins consisting of DP 6-8, DP 9-14, DP 15-24, DP 35-34, DP 35-44, and DP>45. There were no statistically significant differences (P<0.05) among the bins for SSIIa mutants, hulless double mutants and hulled double mutants. However, there was a major difference (P<0.05) between groups containing the wild type SSIIa allele compared to groups containing the mutant SSIIa allele. Those genotypes with the SSIIa mutant allele contained an increased proportion of chains of DP6-8, with greater than 10% of chains of this size, and also an increased proportion of chains of DP 9-14. They also exhibited a decreased proportion of chains with DPI 5-24. The wildtype lines had less than 5% DP6-8 chain lengths. The amo1 mutants contained a statistically significantly decreased amount of DP 9-14 and an increased amount of DP 15-24.

Starch Granule Size Distribution

To investigate the effects of sex6 and amo1 genotype on starch granule size in endosperm starch, the starch granule size distribution was examined for four selected lines from each group of the BC3F6 backcross population. The results showed that B starch granule (defined as <7 μm diameter) contents in the wildtype, amo1 mutants, SSIIa mutants, hulless double mutants and hulled double mutants were 20.2±6.4%, 30.7±3.6%, 17.5±1.8%, 19.7±3.6% and 18.3±7.2% of total starch in each line, respectively. The amo1 mutant seeds contained significantly more B starch granules than seeds from the other four groups.

The mean granule sizes of the distribution peaks larger than 10 μm in diameter (A starch granules) were also evaluated. The mean size of A starch granules was 18.9±0.5 μm for wildtype lines, 10.9±0.3 μm for amo1 mutants, 16.4±2.6 μm for SSIIa mutants, 18.7±0 μm for hulless double mutants and 17.5±0.6 μm for hulled double mutants. Statistical analysis showed that amo1 mutant seeds contained significantly smaller A starch granules than seeds from each of other four groups of barley (P<0.05). There were no statistically significant differences (P<0.05) among the A granules in seeds of wildtype, SSIIa mutants, hulless double mutants and hulled double mutants.

Starch Granule Morphology

Purified barley starches from lines from the five groups were stained with iodine and examined under normal light microscopy. Consistent with their amylose content, starch granules from all genotypes gave a purple color after staining with iodine. Under polarized light microscopy, more than 90% of the starch granules from wildtype seeds and amo1 seeds showed the "maltose cross" birefringence signature of crystalline starch granules. However, less than 10% of the starch granules from SSIIa mutant or double mutant seeds exhibited such birefringence.

When observed under SEM, grain from the wildtype lines exhibited normal spherical starch granules, while the amo1 mutant genotype gave smaller spherical A starch granules that matched the results from the analysis described above. Starches from the SSIIa and double mutant seeds showed predominantly smaller deformed starch granules. Of the two mutants giving deformed starch granules, the SSIIa mutant line produced tubular, elongated A granules (26 μm×12 μm) while the hulless double mutant seeds exhibited more pronounced tubular elongations of the A granules (28 μm×21 μm).

The location of starch granules in the endosperm matrix was examined in transverse sections of the barley seeds. Wildtype lines contained multiple flat spherical starch A granules surrounding multiple small B starch granules while the amo1 mutant line contained multiple loosely packed starch granules surrounding smaller B starch granules. Starch granules could not be clearly identified for the SSIIa mutant seeds in transverse sections. Hulless double mutant lines contained lenticular shaped starch A granules tightly packed in the endosperm cells.

Beta-Glucan Content

Beta-glucan content was measured for all lines from the BC3F6 population. β-glucan content was 6.0±0.5% (ranging from 5.3% to 7.0%) for wildtype lines, 8.2±0.5% (ranging from 7.6% to 8.4%) for amo1 mutant lines, 7.6±1.4% (ranging from 5.9% to 11.3%) for SSIIa mutants, 7.1±0.4% for hulless double mutants and 6.5 f 0.8% (ranging from 5.5% to 7.7%) for hulled double mutants. Statistical analysis showed that amo1 mutant, SSIIa mutant and hulless double mutant seeds contained significantly more β-glucan than seeds from wildtype lines and hulled double mutant lines (P<0.05), but there was no statistically significant difference among amo1 mutants, SSIIa mutants and hulless double mutants, or between wildtype and hulled double mutants seeds in β-glucan content, respectively.

The statistical analysis for these selected F7 lines from five groups grown under glasshouse or field conditions showed that for each trial, seed from amo1 mutant lines contained more β-glucan than seed from double mutant lines. There were no significant differences in β-glucan content between SSIIa mutant or double mutant seeds.

Pentosan Content

Pentosan content was measured for lines from the five groups. Pentosen content was 4.9±0.6% for wildtype lines, 4.9±1.1% for amo1 mutant lines, 7.3±1.4% for SSIIa mutants, 5.0±0.3% for hulless double mutants and 6.5±1.0% for hulled double mutants. Statistical analysis showed that both SSIIa mutant lines and hulled double mutants significantly contained more pentosan than that from wildtype lines, amo1 mutant and hulless double mutant lines (P<0.05), but, there was no significant difference between SSIIa mutant lines and hulled double mutants or among wildtype lines, amo1 mutant and hulless double mutants in pentosan content, respectively.

Ash Content

Ash content was measured for seeds of the five groups. Ash content was 2.5±0.1% for wildtype seed, 2.6±0.2% for amo1 mutant seed, 3.1±0.3% for SSIIa mutant seed, 2.1±0.1% for hulless double mutant seed and 2.7±0.1% for hulled double mutant seed. The SSIIa mutant seeds contained significantly more and hulless double mutant seeds contained significantly less ash than wildtype, amo1 mutant or hulled double mutant seeds, but, there was no significant difference among wildtype lines, amo1 mutant lines and hulled double mutants in ash content, respectively.

Water Soluble Carbohydrates

To determine the effect of the mutations singly or in combination on water soluble carbohydrate contents in barley seeds, four lines were analysed from each group. Compared to the water soluble carbohydrate composition in wildtype seeds, amo1 seeds did not contain significantly different levels of total WSC, free glucose, sucrose or maltose, or fructan. However, SSIIa mutant and double mutant seeds contained significantly greater amounts of each of these carbohydrates (P<0.05). The seeds of the SSIIa single mutants contained significantly more fructose, sucrose and total WSC.

Protein Content

Protein content was measured in seeds of the five groups. Protein content was 10.3±0.8% for wildtype seeds, 10.4±1.1% for amo1 mutant seeds, 12.6±0.9% for SSIIa mutant seeds, 14.6±0.6% for hulless double mutant seeds and 13.8±1.4% for hulled double mutant seeds. Both hulless and hulled double mutant seeds contained significantly more protein than SSIIa mutant seeds, wildtype seeds or amo1 mutant seeds, but there were no significant differences between hulless and hulled double mutant seeds or between amo1 mutants and wildtype seeds in protein content.

Lipid Content

Lipid content was measured for seeds of the five groups. Total lipid content was 2.9±0.2% for wildtype seeds, 3.5±0.3% for amo1 mutant seeds, 6.4±0.9% for SSIIa mutant seeds, 4.9±0.3% for hulless double mutant seeds and 5.0±0.3% for hulled double mutant seeds. SSIIa mutant seeds contained significantly more lipid than hulless and hulled double mutant seeds, wildtype seeds and amo1 mutant seeds, but there were no significant differences between hulless and hulled double mutant seeds or between amo1 mutant and wildtype seeds.

Discussion

The objective of the current study was to examine the interaction between recessive mutations at the sex6 and amo1 loci. Each of these mutations results in an elevated amylose phenotype relative to wildtype, with amylose contents typically 60-70% in the starch of SSIIa mutant seeds and 35-45% in amo1-AC38 seeds. Determination of the 4 possible genotypes for the sex6 (sex6-wt and sex6-292) and amo1 (amo1-wt and amo1-AC38) loci was an important aspect of this study. The mutant and wildtype alleles of the Sex6 locus were able to be unambiguously distinguished using a marker based on the causal mutation in the starch synthase IIa gene. The precise nature of the mutation at the amo1 locus remains unknown, therefore a closely linked marker (Bmac0501, concensus map location 58.0 cM) was used to assay for the presence of the chromosome region containing the amo1 locus.

One objective of the current study was to examine the impact of combining these mutations on amylose content. The data showed that there was no statistically significant difference in the proportion of amylose when the SSIIa mutant and amo1-AC38 loci were combined relative to lines carrying the SSIIa mutant locus alone. However, the combination of the SSIIa and amo1-AC38 mutations did have unexpected consequences on starch synthesis and grain weight; increasing starch content and seed weight relative to the SSIIa mutation alone.

Barley SSIIa mutants contained starch with a high percentage of amylose. The data showed that SSIIa mutant grain on average contained only 40% as much starch as the wildtype grain on a per grain basis. The high amylose phenotype of SSIIa mutant seed was thus due to a preferential reduction of amylopectin, which was decreased by 75%, compared to amylose which was only decreased by 25%. In the case of the SSIIa-amo1 double mutant grain, there was also a decrease in amylopectin synthesis compared to wildtype (31% reduction) but an increase in amylose content (increased by 37%) per seed. These results were intriguing, suggesting that the amo1 gene product not only participated in amylopectin synthesis but also repressed amylose synthesis.

Previous studies of the role of the starch synthase III gene in transient starch synthesis in *Arabidopsis* led Zhang et al., *Plant Physiol.* 138: 663-674, 2005 to conclude that starch synthase III was a negative regulator of starch synthesis in leaves. In rice, two starch synthase III genes are known, SSIIIa and SSIIIb. Of these genes, SSIIIa is expressed in the endosperm during starch synthesis whereas SSIIIb is expressed early in endosperm development but not during periods of highly active starch synthesis later in grain filling (Ohdan et al., *J Exp Bo* 56: 3229-3244, 2005). Mutations in SSIIIa in rice did not decrease starch content, however there was an increase in amylose content from about 15% to 20% suggesting that a decrease in amylopectin synthesis and a concomitant increase in amylose synthesis had occurred (Fujita et al., 2007 (supra)). Consistent with this observation was an increase in GBSSI and SSI activity (Fujita et al., 2007 (supra)). Li et al., 2000 (supra) located the SSIII gene (now designated SSIIIa) to the short arm of wheat chromosome 1, a location not inconsistent with the location of the amo1 locus in barley. The SSIIIa gene was therefore a candidate gene for the causal gene disrupted at the amo1 locus. However, experiments demonstrated that the SSIIIa protein was expressed in amo1 mutants and had starch synthase activity, and that there was a recombination event between SSIIIa and amo1 genes, indicating they are distinct genes.

The impact of the amo1 mutant allele on starch chain length distribution was subtle. In a wildtype background, the presence of the amo1 mutant allele caused a slight decrease in short chain lengths (DP 9-14) and an increase in the DP 15-24 fraction. In SSIIa mutant backgrounds, the impact of the amo1 mutant locus on chain length distribution was negligible. In contrast, the SSIIa mutant allele had a major affect on amylopectin structure and thus chain length distribution, increasing the proportion of short chains (DP 6-8 and DP 9-14) and decreasing chains with DP15-25.

The combination of the SSIIa and amo1 mutant alleles provided an unexpected phenotype in which starch content and seed weight were partially restored compared to the properties of lines containing only the SSIIa mutant allele.

Example 3: Genetic Markers Linked to the Barley Amo1 Locus

The amo1 mutation locus has been mapped at approximately 56.5 cM on chromosome 1H of barley (Barley- BinMap 2005, GrainGene database). In order to test for genetic markers linked closely to the amo1 locus, 11 SSR (Simple Sequence Repeat) markers (Ramsay et al., Genetics. 156(4): 1997-2005, 2000) located between 56.00 cM and 64.60 cM on chromosome 1H of barley were selected and tested for the amplification of PCR products from two parental lines, High Amylose Glacier (HAG) and Himalaya292. These SSR markers were EBmac0405, Bmag0105, Bmac0063, HVM20F, EBmac0560a, EBmac0501, Bmac0044, Bmac0032, Bmag0113, Bmag0211, and Bmag0350. The primers for these SSR markers were synthesized according to the sequences listed in the GrainGenes Database.

For each PCR reaction (20 µl), 50 ng genomic DNA, 1.5 mM $MgCl_2$, 0.125 mM each dNTP, 10 pmol primers, 0.5 M glycine betaine, 1 µl DMSO and 1.5 U of Hotstar Taq polymerase (QIAGEN, Australia) were used. The PCR conditions for the amplifications for the SSR markers were: 1 cycle of 95° C. for 4 minutes, 15 cycles of 94° C. for 30 seconds, 65° C. to 50° C. with decreasing 1° C. each cycle for 30 seconds, and 72° C. for 1 minute 20 seconds, 30 cycles of 94° C. for 15 seconds, 50° C. for 15 seconds, and 72° C. for 45 seconds, and 1 cycle of 25° C. for 1 minute. The PCR products were separated by electrophoresis on 2% agarose gels and visualized with gel documentary (UVitec) after GelRed (Biotium) staining.

When the 11 SSR markers were tested, 2 of 11 markers, namely Bmac0032 located at 64.6 cM and EBmac0501 located at 58.0 cM, gave different sized PCR products for DNA from the HAG and Himalaya292 parental plants. That is, these markers showed polymorphism between the two parental varieties. The size of the amplification products were 175 bp and 189 bp fragments for HAG, and 230 bp and 150 bp for Himalaya292, with the Bmac0032 and EBmac0501 markers, respectively. Both SSR markers were then used for the genotyping of the 70 BC3F6 lines. All of the lines genotyped with the Bmac0032 marker gave the same sized fragments as HAG, which showed that all of the lines had recombined between the Bmac0032 and amo1 loci and the SSR marker Bmac0032 was not tightly linked with the amo1 locus. In contrast, of the 70 BC3F6 lines genotyped with the EBmac0501 marker, 56 were homozygous for one or the other of the fragment patterns. Of the 56 homozygous lines, 25 displayed the EBmac0501 marker from HAG and 31 exhibited the EBmac0501 marker from Himalaya292. These results showed that the EBmac0501 marker did not have a high frequency of genetic recombination with amo1 locus. Therefore, the SSR marker EBmac0501 was a tightly linked microsatellite marker for amo11-AC38 locus.

Markers Based on the SSIIIa Gene of Barley

It was thought that the amo1 locus might be near to the SSIIa gene of barley. To test this possibility and to develop a DNA marker based on the SSIIIa gene in barley, portions of the SSIIa gene were first isolated from the two parental varieties. DNAs from HAG and Himalaya292 were used for the amplification of PCR fragments using primers based on the wheat SSIIIa genomic DNA sequence (Li et al., 2000 (supra)). The oligonucleotide primers SSIIIaF (5'-GGAGGTCTCGGGGATGT-3' (SEQ ID NO: 7)) locating in exon 7 and SSIIaR (5'-GCTCCAG-GAAGTAAACGGTCAGG-3' (SEQ ID NO: 8)) locating in exon 8 of the wheat SSIIIa gene were used for the PCR amplification of a 464 bp product. For each PCR reaction (20 µl), 50 ng genomic DNA, 1.5 mM $MgCl_2$, 0.125 mM each dNTP, 10 pmol primers, 0.5 M glycine betaine, 1 µl DMSO and 1.5 U of Hotstar Taq polymerase were used. The PCR reactions were conducted using 1 cycle of 95° C. for 5 minutes, 35 cycles of 94° C. for 45 seconds, 58° C. for 30 seconds, and 72° C. for 1 minute, 1 cycle of 72° C. for 10 minutes and 1 cycle of 25° C. for 1 minute. A 464 bp fragment was produced in each amplification. The PCR fragments were treated with 0.5 units of Shrimp Alkaline Phosphatase (USB Corporation, USA), 2.5 units of Exonuclease I and 1×PCR buffer (QIAGEN, Australia) according to the protocol from USB Corporation and sequenced using the automated ABI system with dye terminators as described by the manufacturers.

The 464 bp fragments had a sequence difference which provided an NlaIV restriction site in one fragment but not the other. Therefore, treatment of the PCR products with this enzyme followed by electrophoresis on 2% agarose gels provided a convenient way to distinguish the SSIIIa genes from the two parental varieties. The production of only the 464 bp DNA fragment indicated the presence of the SSIIIa gene from Himalaya292, and the production of both 303 bp and 161 bp DNA fragments indicated the presence of the SSIIIa gene from HAG.

Example 4: Field Trials for SSIIa-Amo1 Double Mutants

To evaluate the yield performance of the SSIIa-amo1 double mutants when growing in the field, 3 hulless double mutant lines, 2 hulled double mutant lines, 4 hulless SSIIa mutants, 1 hulled SSIIa mutant line, 1 hulless wildtype barley line (cultivar Torrens), 2 hulled wildtype barley lines (cultivars Tantangara, Sloop) were grown at Narrandera and Moree, NSW, Australia in 2008. Each of the barley lines was grown under both irrigated and non-irrigated (dryland) conditions at both sites. Two plots for each line were grown under each condition at both sites in a randomized pattern. Barley seeds (120 g) were sown in each plot (19 $m^2$).

The grain weight obtained after harvesting each plot in December 2008 was measured. At Narrandera, under irrigation, the double mutant, SSIIa mutant and hulless wildtype lines produced 2.23±0.16 kg, 1.14±0.57 kg and 1.65±0.79 kg of grain, respectively, per plot. Under dryland conditions, the double mutant, SSIIa mutant and hulless wildtype lines produced 0.55±0.34 kg, 0.11±0.12 kg and 0.41±0.16 kg of grain, respectively, per plot.

At Moree, under irrigation, the double mutant, SSIIa mutant and hulless wildtype lines produced 1.62±0.72 kg, 0.54±0.40 kg and 2.11±0.08 kg of grain, respectively. Under dryland conditions, the double mutant, SSIIa mutant and hulless wildtype lines produced 0.88±0.33 kg, 0.38±0.27 kg and 1.14±0.34 kg of barley grains, respectively.

Therefore, under both irrigated and non-irrigated conditions at both sites, hulless double mutant and hulless wildtype lines produced similar yields of grain, that were significantly greater than the yield from hulless SSIIa mutants.

Grain Yield of Hulled Barley Lines:

At Narrandera, under irrigation, the double mutant, SSIIa mutant and hulled wildtype lines produced 2.77±0.37 kg, 2.09±0.76 kg and 4.39±2.59 kg of grain, respectively, per plot. Under dryland conditions, the double mutant, SSIIa mutant and hulled wildtype line produced 0.60±0.06 kg, 0.35±0.14 kg and 0.59±0.46 kg of grain, respectively.

At Moree, under irrigation condition, the double mutants, SSIIa mutants and hulled wildtype lines produced 2.15±0.81 kg, 1.24±0.12 kg and 2.73±0.96 kg of grain, respectively, per plot. Under dryland conditions, the double mutants, SSIIa mutants and hulled wildtype lines produced 1.19±0.40 kg, 0.76±0.60 kg and 2.13±0.23 kg of grain, respectively, per plot.

Therefore, under both irrigated and non-irrigated conditions at both sites, hulled wildtype lines yielded more grain than hulled double mutant and hulled SSIIa mutant lines, and hulled double mutants produced more grain than hulled SSIIa mutants.

Example 5. Production of Food Products

Grain was harvested from eleven barley lines grown in the field at Yanco, NSW, Australia in 2008, and milled to produce flour. The lines were 3 hulless double mutants, 2 hulled double mutants, 3 SSIIa mutants including Himalaya292, 2 wildtype (cultivars Tantangara and Himalaya) and 1 amo1 mutant (HAG). The grain harvested from these lines was milled using a Quadrumat Jnr. mill (Brabender Quadrumat Jnr. Mill, Cyrulla's Instruments, Sydney, NSW Australia) to produce flour that was then sieved to 300 μm diameter. No tempering regime was applied before Quadrumat milling.

Two types of small-scale (10 g) breads were baked for each of 11 barley lines. Small-scale loaves were baked for these test purposes, but the method can be readily scaled up to commercial quantities. One type of bread was made with 100% barley flour as an ingredient, milled as described above, while the other type of bread was made with a blend of 30% flour and 70% commercial wheat flour as the flour ingredient. Flour (13.02 g) and the other ingredients were mixed into a dough, to peak dough development time in a 35-g mixograph. The recipe used, based on the 13.02 g of flour in each case was: flour 100%, salt 2%, dry yeast 1.5%, vegetable oil 2%, and improver 1.5%. The water addition level was based on the micro Z-arm water absorption values that were adjusted for the full formula. The moulding and panning were done in two-stage proofing steps at 40° C. and 85% room humidity. Baking was done in a Rotel oven for 14 min at 190° C.

After baking, the 10 g bread loaves were stored at −80° C. for three weeks for the batch of 100% barley breads, or for 1 week for the batch of 30% barley breads, and then analysed for RS content as described in Example 1, and GI levels. For the RS content, the in vitro procedure determined resistant starch content. Duplicated samples from the 10 g bread loaves, along with appropriate standards, were mixed with artificial saliva, and the resultant bolus was incubated with pancreatic and gastric enzymes at physiological pH and temperature. The amount of residual starch in the digesta was determined using conventional enzymatic and spectrophotometric techniques, and the resistant starch content of the sample was expressed as a percentage of sample weight.

For the determination of GI levels, an in vitro procedure was used.

RS Content of Barley Wholemeals

RS content and GI levels were first determined for the wholemeal milled from each of the groups of barley genotypes. The RS contents were 0.9%, 3.5±0.3%, 3.4±0.1%, 1.9% and 0.5±0.1% for the amo1 mutant, hulless double mutant, hulled double mutant, SSIIa mutant and wildtype wholemeal, respectively (Table 1). Unexpectedly, both the hulless and hulled double mutant wholemeal contained approximately 3.5-, 2.3- and 10-fold higher RS content than the amo1 mutant, SSIIa mutant and wildtype wholemeal, respectively. Importantly, wholemeals from both hulless and hulled double mutants contained significantly more RS than wholemeal from the SSIIa mutant. There were no statistically significant differences in RS content between hulless double mutant and hulled double mutant wholemeal, or between amo1 mutant and wildtype wholemeal. Although GI levels differed among wholemeals from 5 groups of barley, there were not statistically significantly different.

RS Content of Breads Containing 100% Barley Flour

The RS contents for breads that contained 100% barley flour were determined and are given in Table 2. The analyses showed that the RS contents in breads made with 100% barley wholemeal as the flour ingredient were 2.2±0.3%, 5.5±0.1%, 5.6±0.3%, 2.1±0.4% and 0.8±0.3% for amo1 mutant, hulless double mutant, hulled double mutant, SSIIa mutant and wildtype grain (Table 3). The statistical analysis indicated that breads made from wholemeal from both hulless and hulled double mutant barley yielded significantly higher RS contents than that from SSIIa mutants, amo1 mutant and normal barley lines (Table 3). There were no significant differences in RS content from breads containing 100% flour of hulless and hulled double mutants. The breads from hulless and hulled double mutants produced 2.5-fold, 2.5-fold and 6.7-fold higher RS content than bread made from SSIIa mutant, amo1 mutant and normal barley, respectively (Table 3).

RS Content of Breads Containing 30% Barley Flour

The RS contents of breads that contained 30% barley flour were determined and are given in Table 4. RS contents of breads made from amo1 mutant, hulless double mutant, hulled double mutant, SSIIa mutant and wildtype wholemeal were 1.9±0.3%, 3.1±0.2%, 3.0±0.1%, 2.0±0.3%, 0.9±0.1%, respectively (Table 3). Breads from both hulless and hulled double mutant barley yielded significantly higher RS contents than bread from SSIIa mutant, amo1 mutant and normal barley grain (Table 3). There were no significantly differences in RS content between breads containing 30% flour of hulless and hulled double mutants. The breads from hulless and hulled double mutants produced 1.6-, 1.6- and 3.3-fold higher RS content than bread from SSIIa mutants, amo1 mutant and normal barley lines, respectively (Table 3).

The calculation of RS content as mg RS per gram of starch was performed to analyse the nature of the increase of RS in breads made from the double mutants. These data were analysed to see whether the increase of RS content was due to the increase of total starch or due to the changes of starch structure. The results showed that bread produced with 100% barley flour from amo1 mutant, hulless double mutant, hulled double mutant, SSIIa mutant and wildtype grain had 41.7, 105.1±2.8, 106.9±3.3, 75.0±8.1 and 16.3±4.5 mg RS per g of starch of breads (Table 5). Both hulless double mutants and hulled double mutant breads yielded approximately 2.5-, 1.4- and 6.5-fold higher RS than breads from amo1 mutant, SSIIa mutant and wildtype grain. The statistical analysis showed that although breads from all 4 groups of barley contained more RS than that from the wildtype lines, the RS content (mg RS per g of starch) of breads from both double mutants were statistically significantly higher than that from amo1 mutants, SSIIa mutants (P<0.05). Bread from SSIIa mutant grain contained statistically significantly more RS than that from amo1 mutants.

GI Level of 100% Barley Breads

The GI level of breads that contained 100% barley flour from all barley lines were determined and are given in Table 2. GI levels of breads from amo1 mutant, hulless double mutant, hulled double mutant, SSIIa mutant and wildtype grain were 68.5±2.1, 63.5±4.5, 60.8±4.1, 63.9±10.3, 80.3±2.9, respectively (Table 7). The statistical analysis indicated that breads from both hulless and hulled double mutant, and SSIIa mutant grain produced significantly lower values of GI than that from amo1 mutant and normal barley lines (Table 7). There were no significant differences for GI values for breads containing 100% flour of hulless and hulled double mutant, and SSIIa mutant grain. The breads from hulless and hulled double mutant, and SSIIa mutant grain yielded approximately 80% of GI level as that from amo1 mutant and normal barley lines, respectively (Table 7).

GI Level of 30% Barley Breads

The GI level of breads that contained 30% barley flour from all barley lines were determined and are given in Table 4. GI levels of breads from amo1 mutants, hulless double mutants, hulled double mutants, SSIIa mutants and wildtype lines were 84.5±3.5, 83.2±2.1, 83.5±0.8, 82.3±3.9, 87.8±4.5, respectively (Table 7). The GI values for breads made from the 5 groups of barley were not statistically significantly different.

effective relative to existing methods of fructan production, for example, involving the extraction of inulins from chicory.

Large scale extraction of fructan can be achieved by milling the grain to wholemeal flour and then extracting the total sugars including fructans from the flour into water. This may be done at ambient temperature and the mixture then centrifuged or filtered. The supernatant is then heated to about 80° C. and centrifuged to remove proteins, then dried down. Alternatively, the extraction of flour can be done using 80% ethanol, with subsequent phase separation using water/chloroform mixtures, and the aqueous phase containing sugars and fructan dried and redissolved in water. Sucrose in the extract prepared either way may be removed enzymatically by the addition of α-glucosidase, and then hexoses (monosaccharides) removed by gel filtration to produce fructan fractions of various sizes. This would produce a fructan enriched fraction of at least 80% fructan.

TABLE 1

RS content and GI level of barley wholemeal

| Genotype | Line name | GI | GI average | SD | RS wholemeal (g/100 g) | RS average | SD |
|---|---|---|---|---|---|---|---|
| amo1 mutant | HAG | 64.6 | 64.6 [a] | | 0.9 | 0.9 [c] | |
| Hulled double mutant | HHF7-88 | 81.0 | 79.0 [a] | 2.8 | 3.5 | 3.4 [a] | 0.1 |
| Hulled double mutant | HHF7-122 | 77.0 | | | 3.3 | | |
| Hulless double mutant | HHF7-4 | 77.3 | 78.0 [a] | 0.9 | 3.3 | 3.5 [a] | 0.3 |
| Hulless double mutant | HHF7-7 | 79.1 | | | 3.4 | | |
| Hulless double mutant | HHF7-29 | 77.8 | | | 3.8 | | |
| SSIIa mutant | 292.0 | 68.2 | 68.2 [a] | | 1.9 | 1.9 [b] | |
| wildtype barley | Himalaya | 76.6 | 70.8 [a] | 9.6 | 0.6 | 0.5 [c] | 0.1 |
| wildtype barley | Glacier | 76.0 | | | 0.4 | | |
| wildtype barley | Tantangara | 59.7 | | | 0.4 | | |
| LSD (5%) | | | 22.6 | | | 0.7 | |

L.S.D.: it is the least significant difference; differences greater than this are significant (P < 0.05).
[a], [b] and [c] based on LSD, mean values with the same letter are not significantly different, and with the different letter are significantly different at significant difference (P < 0.05).

Conclusions

Wholemeal from both hulless and hulled double mutant barley grain contained significantly higher RS contents than wholemeal from amo1 mutant, SSIIa mutant and wildtype grain. Wholemeal from both double mutants contained approximately 3.5-, 1.8- and 7.0-fold higher RS content comparing to wholemeal from amo1 mutants, SSIIa mutants and wildtype lines. In a similar pattern, bread made from the double mutant barley grain contained significantly higher RS content than bread made from SSIIa mutants, amo1 mutant and wildtype barley. The increase of RS content was not only due to the increase of amount of high amylose starch, but also the changes of starch structure as the increase of RS content was observed per g of starch.

Breads from both double mutant and SSIIa mutant grain yielded significantly lower GI values than that from both amo1 mutant and wildtype grain. The GI values of breads containing SSIIa-amo1 double mutant grain and SSIIIa mutant grain were approximately 7% and 20% lower than of breads containing amo1 mutant and wildtype grain when the breads were made from 100% barley flour.

Example 6: Large Scale Production of Fructan

Having about 10% fructan, the barley grain mutant in SSIIa and amo1 can be used for the isolation and purification of fructan as well as other products such as high amylose starch and β-glucan. Such production from grain which can be readily produced in broadacre agriculture will be cost-

TABLE 2

RS content and GI level of bread produced using 100% barley wholemeal

| Sample ID | Genotype | Line name | RS content (g/100 g) | GI level |
|---|---|---|---|---|
| ZL2.9.1 | amo1 mutant | HAG | 2.39 | 70 |
| ZL2.9.1 | amo1 mutant | HAG | 2.01 | 67 |
| 10.1 | Hulless double mutant | HHF7_29 | 5.46 | 57 |
| 10.1 | Hulless double mutant | HHF7_29 | 5.6 | 62 |
| 6.1 | Hulless double mutant | HHF7_4 | 5.53 | 66 |
| 6.1 | Hulless double mutant | HHF7_4 | 5.32 | 61 |
| 2.1 | Hulless double mutant | HHF7_7 | 5.61 | 70 |
| 2.1 | Hulless double mutant | HHF7_7 | 5.65 | 65 |
| 11.1 | hulled double mutant | HHF7_88 | 5.76 | 66 |
| 11.1 | hulled double mutant | HHF7_88 | 5.96 | 62 |
| 1.1 | hulled double mutant | HHF7_122 | 5.29 | 57 |
| 1.1 | hulled double mutant | HHF7_122 | 5.2 | 58 |
| ZL1.8.1 | SSIIa mutant | 871 | 1.96 | 49 |
| ZL1.8.1 | SSIIa mutant | 871 | 2.08 | 53 |
| ZL1.1.1 | SSIIa mutant | Himalaya292 | 1.49 | 57 |
| ZL1.1.1 | SSIIa mutant | Himalaya292 | 1.58 | 60 |
| 4.1 | SSIIa mutant | HHF7_50 | 2.22 | 74 |
| 4.1 | SSIIa mutant | HHF7_50 | 2.26 | 74 |
| 3.1 | wildtype | Himalaya | 0.65 | 82 |
| 3.1 | wildtype | Himalaya | 0.52 | 82 |
| 9.1 | wildtype | Tantangara | 1.04 | 76 |
| 9.1 | wildtype | Tantangara | 1.05 | 81 |

TABLE 3

Statistical analysis of the effects of genotype on RS contents of bread produced with 30% or 100% barley flour

| Genotype | No Sample | RS content 100% (g/100 g) | SD | RS content 30% (g/100 g) | SD |
|---|---|---|---|---|---|
| amo1 mutant | 2 | 2.2[b] | 0.3 | 1.9[b] | 0.3 |
| hulless double mutant | 6 | 5.5[a] | 0.1 | 3.1[a] | 0.2 |
| hulled double mutant | 4 | 5.4[a] | 0.4 | 3.0[a] | 0.1 |
| SSIIa mutant | 6 | 1.9[b] | 0.4 | 1.8[b] | 0.3 |
| Wildtype | 4 | 0.7[c] | 0.3 | 1.0[c] | 0.1 |
| L.S.D. ($P < 0.05$) | | 0.5 | | 0.3 | |

Note:
RS content 30%: RS content of the breads that contained 30% barley flour.
RS content 100%: RS content of the breads that contained 100% barley flour.
L.S.D.: it is the least significant difference; differences greater than this are significant ($P < 0.05$).
[a,b] and [c] based on LSD, mean values with the same letter are not significantly different, and with the different letter are significantly different at significant difference ($P < 0.05$).

TABLE 4

RS content and GI level of breads produced with 30% barley flour

| Sample ID | Genotype | Line name | RS (g/100 g) | GI level |
|---|---|---|---|---|
| ZL1.4.1 | amo1 mutant | HAG | 2.15 | 82 |
| ZL1.4.1 | amo1 mutant | HAG | 1.72 | 87 |
| ZL1.5.1 | Hulless double mutant | HHF7_29 | 3.01 | 83 |
| ZL1.5.1 | Hulless double mutant | HHF7_29 | 3.07 | 82 |
| ZL2.7.1 | Hulless double mutant | HHF7_4 | 3.03 | 83 |
| ZL2.7.1 | Hulless double mutant | HHF7_4 | 3.27 | 83 |
| ZL2.6.1 | Hulless double mutant | HHF7_7 | 3.15 | 84 |
| 212.6.1 | Hulless double mutant | HHF7_7 | 3.03 | 84 |
| ZL1.3.1 | Hulled double mutant | HHF7_88 | 3.04 | 83 |
| ZL1.3.1 | Hulled double mutant | HHF7_88 | 3.09 | 86 |
| ZL1.10.1 | Hulled double mutant | HHF7_122 | 3.01 | 81 |
| ZL1.10.1 | Hulled double mutant | HHF7_122 | 2.71 | 84 |
| ZL2.1.1 | SSIIa mutant | 871 | 1.87 | 77 |
| ZL2.1.1 | SSIIa mutant | 871 | 1.82 | 81 |
| ZL2.3.1 | SSIIa mutant | Himalaya292 | 1.7 | 80 |
| ZL2.3.1 | SSIIa mutant | Himalaya292 | 1.87 | 82 |
| ZL2.2.1 | SSIIa mutant | HHF7_50 | 2.15 | 86 |
| ZL2.2.1 | SSIIa mutant | HHF7_50 | 1.69 | 84 |
| ZL1.2.1 | wildtype | Himalaya | 0.96 | 93 |
| ZL1.2.1 | wildtype | Himalaya | 1.02 | 94 |
| ZL2.8.1 | wildtype | Tantangara | 0.84 | 83 |
| ZL2.8.1 | wildtype | Tantangara | 0.89 | 85 |

TABLE 5

Statistical analysis of the effects of genotype on RS content (mg RS per g starch) of bread produced with 100% barley flour

| Genotype | No of samples | RS content 100% (g/100 g) | SD | Total starch in breads (%) | SD | mg RS per g starch | SD |
|---|---|---|---|---|---|---|---|
| amo1 mutant | 1 | 2.2[b] | 0.3 | 57.4[a] | — | 41.7[c] | |
| hulless double mutant | 3 | 5.5[a] | 0.1 | 52.7[a] | 1.8 | 105.1[a] | 2.8 |
| hulled double mutant | 2 | 5.4[a] | 0.4 | 51.8[a] | 4.7 | 106.9[a] | 3.3 |
| SSIIa mutant | 3 | 1.9[b] | 0.4 | 25.1[b] | 3.0 | 75.0[b] | 8.1 |
| Wildtype | 2 | 0.7[c] | 0.3 | 51.6[a] | 2.6 | 16.3[d] | 4.5 |
| L.S.D. ($P < 0.05$) | | 0.5 | | 8.9 | | 16.3 | |

TABLE 6

Statistical analysis of the effects of genotype on RS content (mg RS per g starch) of breads produced with 30% barley flour

| Genotype | No Sample | S content 30% (g/100 g) | SD | Total starch in breads (%) | SD | mg RS per g starch | SD |
|---|---|---|---|---|---|---|---|
| amo1 mutant | 1 | 1.9[b] | 0.3 | 61.9[a] | — | 30.7[b] | |
| hulless double mutant | 3 | 3.1[a] | 0.2 | 65.3[a] | 2.2 | 47.5[a] | 0.8 |
| hulled double mutant | 2 | 3.0[a] | 0.1 | 63.7[a] | 1.1 | 47.1[a] | 3.0 |
| SSIIa mutant | 3 | 1.8[b] | 0.3 | 58.0[b] | 2.3 | 31.6[b] | 0.3 |
| Wildtype | 2 | 1.0[c] | 0.1 | 65.1[a] | 0.1 | 14.6[c] | 1.1 |
| L.S.D. ($P < 0.05$) | | 0.3 | | 5.6 | | 4.2 | |

TABLE 7

Statistical analysis of the effects of genotype on GI level of the 10 g breads produced with 30% or 100% barley flour

| Genotype | No Sample | GI level 100% | SD | GI level 30% | SD |
|---|---|---|---|---|---|
| amo1 mutant | 2 | 68.5[a] | 2.1 | 84.5[a] | 3.5 |
| hulless double mutant | 6 | 63.5[b] | 4.5 | 83.2[a] | 2.1 |
| hulled double mutant | 4 | 60.8[b] | 4.1 | 83.5[a] | 0.8 |
| SSIIa mutant | 6 | 63.9[b] | 10.3 | 82.3[a] | 3.9 |
| Wildtype | 4 | 80.3[a] | 2.9 | 87.8[a] | 4.5 |
| L.S.D. (P < 0.05) | | 12.1 | | 5.8 | |

GI level 30%: GI level of the breads that contained 30% barley flour.

GI level 100%: GI level of the breads that contained 100% barley flour.

L.S.D.: it is the least significant difference; differences greater than this are significant (P < 0.05).

[a] and [b] based on LSD, mean values with the same letter are not significantly different, and with the different letter are significantly different at significant difference (P < 0.05).

TABLE 8

Summary of sequence identifiers

| SEQUENCE ID NO: | DESCRIPTION |
|---|---|
| 1 | *Hordeum vulgare* subsp. *vulgare* starch synthase II mRNA, complete cDNA sequence. Accession No. AY133249, 2972 nucleotides, protein coding region: nucleotides 114-2522, on chromosome 7 of barley. |
| 2 | Amino acid sequence of starch synthase II encoded by SEQ ID NO: 1; 802 amino acids |
| 3 | oligonucleotide primer starting at nucleotide 1616 of SSIIa cDNA (SSIIaF) GenBank No. AY133249 |
| 4 | oligonucleotide primer starting at nucleotide 2044 of the SSIIa cDNA (SSIIaR) GenBank No. AY133249 |
| 5 | oligonucleotide primer for amo1 locus HHac0501F |
| 6 | oligonucleotide primer for amo1 locus HHac0501R |
| 7 | oligonucleotide primer for SSIIIaF |
| 8 | oligonucleotide primer for SSIIIaR |
| 9 | nucleotide sequence of SSIIa of M292 (cDNA) |
| 10 | amino acid sequence encoded by nucleotides 1-1852 of SEQ ID NO: 9 |
| 11 | amino acid sequence encoded by nucleotides 1856-2946 of SEQ ID NO: 9 |

TABLE 9

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 10

Exemplary and Preferred Amino Acid Substitutions

| Original Residue | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Adams et al., *Anal. Biochem.*, 266: 77-84, 1999

Almeida and Allshire, *Trends Cell Biol.* 15: 251-258, 2005

Altschul et al., *Nucleic Acids Res.* 25: 3389, 1997

An, *Methods in Enzymology*, 153: 292, 1987

Andersson et al., *J. Cereal Sci* 30: 183-191, 1999

Ausubel et al., "*Current Protocols in Molecular Biology*", John Wiley & Sons Inc, Unit 19.3 and Chapter 15, 1994-1998

Ausubel et al., (eds.), *Current Protocols in Molecular Biology*, John Wiley & Sons, NY, 6.3.1-6.3.6., 1989

Ball and Morell, *Annu Rev Plant Biol*, 54: 207-233, 2003

Ball et al., *Cell* 86(3): 349-52, 1996

Barker et al., *Plant Mol. Biol.*, 2: 235-350, 1983

Batey et al., *Starch* 48: 338-344, 1997

Bechtold et al., *C. R. Acad. Sci. Paris*, 316: 1194, 1993

Bernfeld, Amylases alpha and beta. In: Colowick and Kaplan (eds), Methods in enzymology, Academic, NY, p. 149, 1955

Bevan et al., *Nucl. Acid Res.*, 11: 369, 1983

Birch, *Ann Rev Plant Physiol Plant Mol Biol.* 48: 297-326, 1997

Bird et al. *Br. J. Nutr.* 92: 607-615, 2004b

Bird et al., *J Nutr*, 134: 831-835, 2004a

Bourque, *Plant Sci.* 105: 125-149, 1995

Boyer and Preiss, *Carbohydrate Research*, 61: 321-334, 1978

Buléon et al., *International Journal of Biological Macromolecules*, 23: 85-112, 1998

Campbell et al., *J Sci Food Agric* 79: 232-236, 1999

Cao et al., *Archives of Biochemistry and Biophysics*, 373: 135-146, 2000

Cao et al., *Plant Physiol.* 120(1): 205-16, 1999

Comai et al., *Plant J.* 37: 778-786, 2004

Craig et al., *Plant Cell*, 10: 413-426, 1998

De Framond, *Biotechnology*, 1: 262, 1983

Deikman et al., *EMBO J.*, 2: 3315-3320, 1998

DellaPenna et al., *Plant Cell*, 1: 53-63, 1989

Delvalle et al., *Plant J.* 43(3): 398-412, 2005

Denyer et al., *Plant Physiol.* 112(2):779-85, 1996

Durai et al., *Nucleic Acids Research* 33(18): 5978-5990, 2005
Fromm et al., *Proc. Natl. Acad. Sci. U.S.A.* 82: 5824, 1985
Fujita et al., *Plant Physiol*, 144: 2009-2023, 2007
Fujita et al., *Plant Physiol.* 140: 1070-1084, 2006
Gao et al, *Plant Cell*, 10: 399-412, 1998
Garfinkel et al, *Cell*, 27: 143-153, 1983
Greve, *J. Mol. Appl. Genet.*, 1: 499-511, 1983
Harayama, *Trends Biotechnol.* 16: 76-82, 1998
Hartmann and Endres, *Manual of Antisense Methodology*, Kluwer, 1999
Haseloff and Gerlach, *Nature* 334: 585-591, 1988
Hayashi et al., Effects of ion beam irradiation on mutation induction in rice. Cyclotrons and Their Applications 2007, Eighteenth International Conference 237-239, 2007
Hedman and Boyer, *Biochemical Genetics*, 20: 483-492, 1982
Hendrix et al., *J. Insect Physiol.*, 47: 423-432, 2001
Henikoff et al., *Plant Physiol.* 135: 630-636, 2004
Hinchee et al., *Biotech.* 6: 915, 1988
Hirose and Terao, *Planta*, 220: 9-16, 2004
Hoekema et al., *Nature*, 303: 179, 1983
James et al., *Curr Opin Plant Biol*, 6: 215-222, 2003
James et al., *Plant Cell*, 7: 417-429, 1995
Jane et al., *Cereal Chem.* 76: 629-637, 1999
Joshi, *Nucl. Acid Res.* 15: 6643, 1987
Kazama et al, *Plant Biotechnology* 25: 113-117, 2008
Kim et al., *J Cereal Sci*, 37: 195-204, 2003
Klein et al., *Nature*, 327: 70, 1987
Konik-Rose et al., *Starch-Stärke*, 53: 14-20, 2001
Konik-Rose et al., *Theor Appl Genet*, 115: 1053-1065, 2007
Kossmann and Lloyd, *Crit Rev Plant Sci*, 19: 171-226, 2000
Kubo et al., *Plant Physiology*, 121: 399-409, 1999
Langridge et al., *Aust J Agric Res* 52: 1043-1077, 2001
Le Provost et al., *Trends in Biotechnology* 28(3): 134-141, 2009
Lemieux, *Current Genomics*, 1: 301-311, 2000
Li et al., *Funct Integr Genomics*, 3: 76-85, 2003
Li et al., *Plant Physiol*, 120: 1147-1156, 1999a
Li et al., *Plant Physiology*, 123: 613-624, 2000
Li et al., *Theoretical and Applied Genetics*, 98: 1208-1216, 1999b
Libessart et al. *Plant Cell.* 7(8): 1117-1127, 1995
Liu et al., *Biotechnology and Bioengineering*, 106: 97-105, 2010
Lunn and Hatch, *Planta* 197: 385-391, 1995
Maddelein et al., *J Biol Chem.* 269(40): 25150-7, 1994
McPherson and Moller (Ed), BIOS Scientific Publishers Ltd, Oxford, 2000
Medberry et al., *Plant Cell*, 4: 185-192, 1992
Medberry et al., *Plant J.* 3: 619-626, 1993
Millar and Waterhouse, *Funct Integr Genomics*, 5: 129-135, 2005
Miura et al., *Euphytica*, 108: 91-95, 1999
Miura et al., *Euphytica*, 123: 353-359, 2002
Mizuno et al., *Journal of Biochemistry*, 112: 643-651, 1992
Morell et al., Control of starch biosynthesis in vascular plants and algae. In: Plaxton W C, McManus M T (eds) Control of primary metabolism in plants. Annual plant reviews, vol 22, Blackwell, Oxford, pp 258-289, 2006
Morell et al., *Euphytica*, 119: 55-58, 2001
Morell et al., *J Appl Glycosci*, 50: 217-224, 2003a
Morell et al., *Plant, J* 34: 173-185, 2003b
Morrison and Laignelet, *J Cereal Sci*, 1: 9-20, 1983
Morrison et al., *J Cereal Sci*, 2: 257-271, 1984
Myers et al., *Plant Physiology*, 122: 989-997, 2000
Needleman and Wunsch, *J. Mol. Biol.* 48: 443-453, 1970
Niedz et al., *Plant Cell Reports*, 14: 403, 1995
O'Shea et al., *Carbohydr Res*, 307: 1-12, 1998
Ohdan et al., *J Exp Bo* 56: 3229-3244, 2005
Ow et al., *Science*, 234: 856, 1986
Pasquinelli et al., *Curr Opin Genet Develop* 15: 200-205, 2005
Perriman et al., *Gene*, 113: 157-163, 1992
Potrykus et al., *Mol. Gen. Genet.* 199: 183, 1985
Prasher et al., *Biochem. Biophys. Res. Comm.* 126: 1259-68, 1985
Rahman et al., *J Cereal Sci*, 31: 91-110, 2000
Ramsay et al., *Genetics.* 156(4): 1997-2005, 2000
Regina et al., *Proc Natl Acad Sci USA*, 103: 3546-3551, 2006
Remington's Pharmaceutical Sciences, 18th Ed., Mack Publishing, Company, Easton, Pa., U.S.A. 1990
Robinson, *The Organic Constituents of Higher Plants*, Cordus Press, North Amherst, USA, Example 9, 1980
Roldan et al, *Plant J.* 49: 492-504, 2007
Ruuska et al., *Funct Plant Biol* 33: 799-809, 2006
Salomon et al, *EMBO J.*, 3: 141-146, 1984
Sambrook et al., *Molecular Cloning: A Laboratory Manual* (2nd ed.). Cold Spring Harbour Laboratory, Cold Spring Harbour, N.Y., 1989
Schondelmaier et al., *Plant Breeding*, 109: 274-281, 1992
Senior, *Biotech. Genet. Engin. Revs.* 15: 79-119, 1998
Shimamoto et al., *Nature*, 338: 274-276, 1989
Shippy et al., *Mol. Biotech.* 12: 117-129, 1999
Slade and Knauf, *Transgenic Res.* 14: 109-115, 2005
Smith et al., *Nature*, 407: 319-320, 2000
Smith, *Biomacromolecules*, 2: 335-341, 2001
Stalker et al., *Science*, 242: 419, 1988
Sun et al., *The New Phytologist*, 137: 215-215, 1997
Tetlow et al., *J Exp Bot*, 55: 2131-2145, 2004
Theander et al., *J AOAC Int* 78: 1030-1044, 1995
Thillet et al., *J. Biol. Chem.* 263: 12500, 1988
Thompson et al., *Carbohydrate Res.*, 331: 149-161, 2001
Tingay et al., *Plant J.* 11: 1369-1376, 1997
Topping et al., *Starch-Stärke*, 55: 539-545, 2003
Veronese et al., *Enz. Microbial Tech.*, 24: 263-269, 1999
Wan and Lemaux, *Plant Physiol.* 104: 37-48, 1994
Waterhouse et al., *Proc. Natl. Acad. Sci. U.S.A.* 95: 13959-13964, 1998
Yamamori and Quynh, *Theor Appl Genet*, 100: 32-38, 2000
Yamamori et al., *Theor Appl Genet*, 101: 21-29, 2000
Yasui et al., *J Cereal Sci*, 24: 131-137, 1996
Zhang et al., *Plant Physiol.* 138: 663-674, 2005
Zwar and Chandler, *Planta* 197: 39-48, 1995

The claims defining the invention are as follows:

1. A method for providing starch to improve one or more indicators of health in a human, wherein the method comprises administering, to the human, a composition comprising barley grain, or wholemeal or flour obtained from barley grain, wherein the barley grain comprises (i) a loss of function mutation in an endogenous gene encoding starch synthase IIa (SSIIa), and (ii) an amo1-AC38 allele, wherein the barley grain is homozygous for the loss of function mutation in the endogenous gene encoding SSIIa and for the amo1-AC38 allele, and the barley grain lacks detectable SSIIa protein in endosperm of the grain.

2. The method of claim 1 wherein the barley grain comprises a starch content of at least 47% (w/w).

3. The method of claim 1 wherein the barley grain comprises a starch content of 41-65% (w/w).

4. The method of claim 1 wherein the barley grain comprises an amylose content of at least 50% as a proportion of the total starch in the grain.

5. The method of claim 1 wherein the barley grain comprises a β-glucan content of 5-9% (w/w).

6. The method of claim 1 wherein the barley grain comprises a β-glucan content of greater than 9% (w/w).

7. The method of claim 1 wherein the barley comprises a fructan content of 3-11% (w/w).

8. The method of claim 7 wherein the fructan comprises a degree of polymerization from about 3 to about 12.

9. The method of claim 1 wherein the loss of function mutation in the endogenous gene encoding SSIIa in the barley grain is the result of the presence of stop codon within the SSIIa gene.

10. The method of claim 1 wherein the loss of function mutation in the endogenous gene encoding SSIIa in the barley grain is comprised in a sex6-292 allele.

11. The method of claim 1 wherein the barley is hulless barley grain.

12. The method of claim 1, wherein the one or more indicators of health in a human comprises reduced blood glucose.

13. The method of claim 12, wherein the barley grain comprises a starch content of at least 47% (w/w).

14. A method for providing starch, amylose, amylopectin, β-glucan, fructan, non-starch polysaccharide, dietary fibre or resistant starch to a mammal, wherein the method comprises administering, to the mammal, a composition comprising barley grain, or wholemeal or flour obtained from the barley grain, wherein the barley grain comprises (i) a loss of function mutation in an endogenous gene encoding starch synthase IIa (SSIIa), and (ii) an amo1-AC38 allele, wherein the barley grain is homozygous for the loss of function mutation in the endogenous gene encoding SSIIa and for the amo1-AC38 allele, and the barley grain lacks detectable SSIIa protein in endosperm of the grain, wherein the composition has a reduced glycaemic index relative to a composition comprising wild-type barley grain or wholemeal or flour obtained from wild-type barley grain.

15. The method of claim 14, wherein the barley grain comprises a starch content of at least 47% (w/w).

* * * * *